(12) United States Patent
Marder et al.

(10) Patent No.: US 7,459,106 B2
(45) Date of Patent: Dec. 2, 2008

(54) MATERIALS, METHODS, AND USES FOR PHOTOCHEMICAL GENERATION OF ACIDS AND/OR RADICAL SPECIES

(75) Inventors: Seth Marder, Atlanta, GA (US); Joseph Perry, Atlanta, GA (US); Wenhui Zhou, Tucson, AZ (US); Stephen M. Kuebler, Oviedo, FL (US); J. Kevin Cammack, Oceanside, CA (US)

(73) Assignee: The Arizona Board of Regents on Behalf of the University of Arizona, Tucson, AZ (US)

( * ) Notice: Subject to any disclaimer, the term of this patent is extended or adjusted under 35 U.S.C. 154(b) by 336 days.

(21) Appl. No.: 10/473,365

(22) PCT Filed: Apr. 1, 2002

(86) PCT No.: PCT/US02/08227

§ 371 (c)(1),
(2), (4) Date: Dec. 6, 2004

(87) PCT Pub. No.: WO02/079691

PCT Pub. Date: Oct. 10, 2002

(65) Prior Publication Data

US 2005/0173683 A1    Aug. 11, 2005

Related U.S. Application Data

(60) Provisional application No. 60/280,672, filed on Mar. 30, 2001.

(51) Int. Cl.
  *G03C 1/73*   (2006.01)
  *C09K 9/02*   (2006.01)
  *G03G 5/00*   (2006.01)

(52) U.S. Cl. .................. 252/600; 252/582; 252/583; 252/501.1; 568/77

(58) Field of Classification Search .......... 252/600, 252/582, 501.1, 583; 568/77
  See application file for complete search history.

(56) References Cited

U.S. PATENT DOCUMENTS

| 4,931,371 | A  |   | 6/1990 | Matsumoto et al. |        |
|-----------|----|---|--------|------------------|--------|
| 6,086,794 | A  |   | 7/2000 | Nobutoki et al.  |        |
| 6,267,913 | B1 |   | 7/2001 | Marder et al.    |        |
| 6,529,539 | B1 | * | 3/2003 | Wada ............ | 372/89 |
| 6,852,766 | B1 | * | 2/2005 | DeVoe ........... | 522/25 |

FOREIGN PATENT DOCUMENTS

| JP | 1-136159   | 5/1989  |
| JP | 1-136160   | 5/1989  |
| JP | 11-008068  | 1/1999  |
| JP | 11-040359  | 2/1999  |
| JP | 11-102784  | 4/1999  |
| JP | 11-265786  | 9/1999  |
| WO | WO 98/21521 | 5/1998 |
| WO | WO 99/53242 | 10/1999 |

OTHER PUBLICATIONS

Mariacristina Rumi, et al., "Structure-Property Relationships for Two-Photon Absorbing Chromophores: Bis-Donor Diphenylpolyene and Bis(styryl)benzene Derivatives", J. Am. Chem. Soc, vol. 122, 2000, 9500-9510.

* cited by examiner

*Primary Examiner*—Timothy J Kugel
(74) *Attorney, Agent, or Firm*—Oblon, Spivak, McClelland, Maier & Neustadt, P.C.

(57) ABSTRACT

The present invention provides compounds and compositions, which include: at least one chromophore having strong simultaneous two-photon or multi-photon absorptivity; at least one acid- or radical-generator in close proximity to the chromophore; such that the single- or multi-photon excitation of the chromophore results in the generation of an acid and/or redical that is capable of activating chemistry; and such that compositions of matter based on the componds and compositions of the invention can be photo-patterned by one- or multiphoton excitation.

24 Claims, 8 Drawing Sheets

Figure 1. Two-photon dye covalently attached to a photoacid.
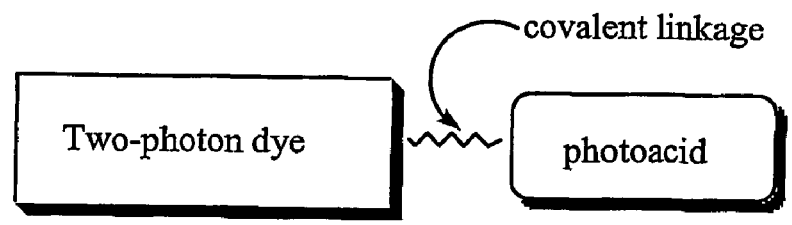
Figure 2. Two-photon dye non-covalently attached to a photoacid.
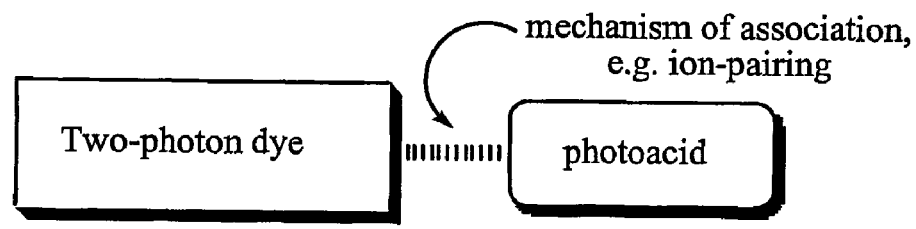

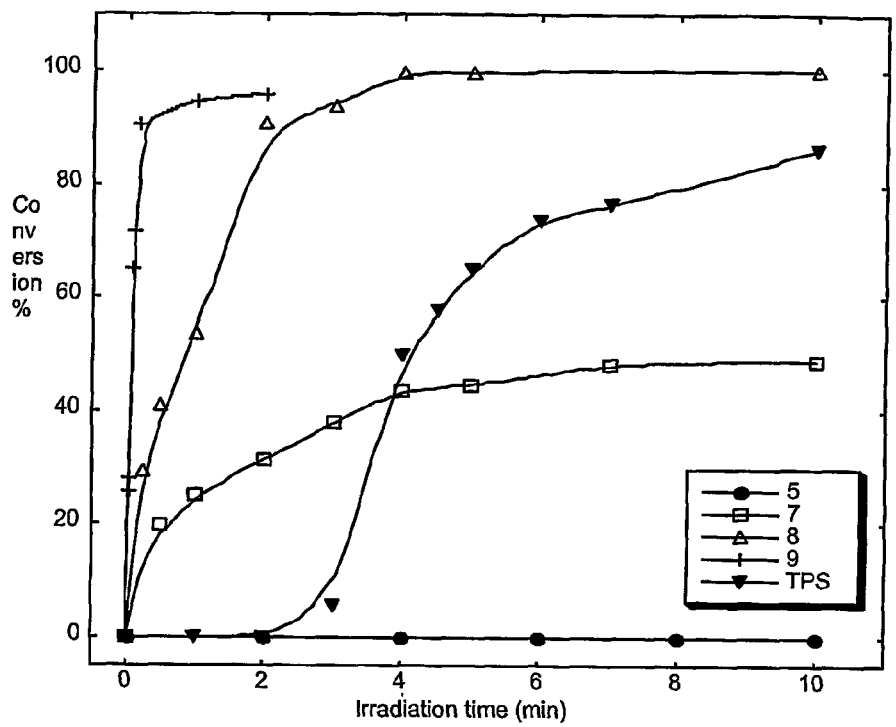
Figure 3. Photopolymerization kinetics of cyclohexene oxide initiated by different triphenylamine sulfonium salts in dichloromethane irradiated at 300 nm. Concentration of monomer: 7.91 mol/L; concentration of initiator: 3.16 x $10^{-3}$ mol/L. Lines are a guide to the eye.

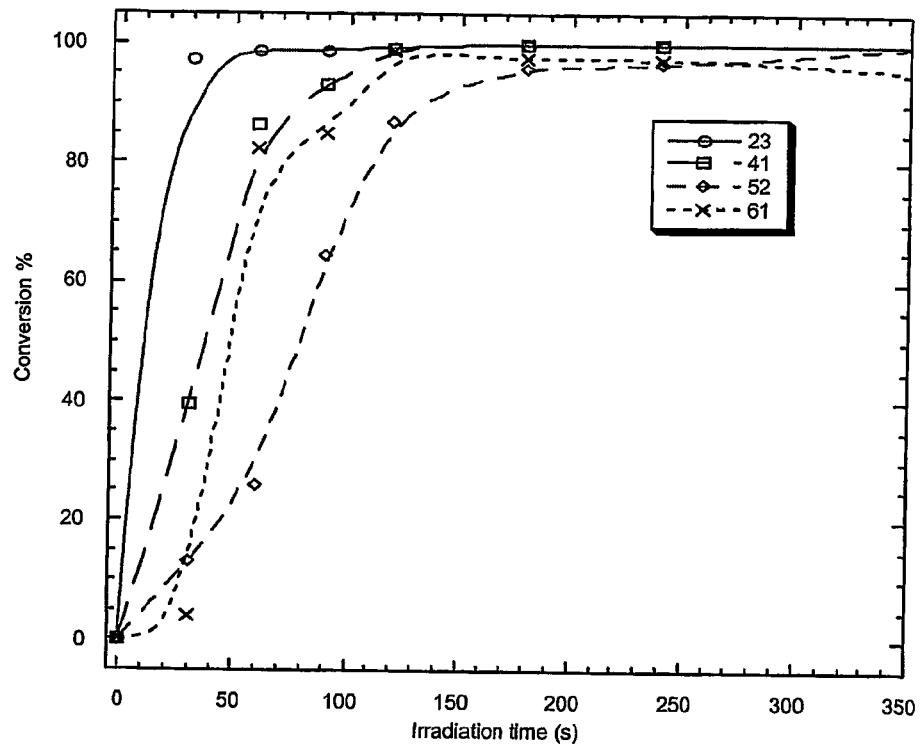
Figure 4. Photopolymerization initiated by different initiators in $CH_2Cl_2$ at 419 nm [Monomer]: 7.906 mol/L; [initiator]: 7.906 x $10^{-3}$ mol/L

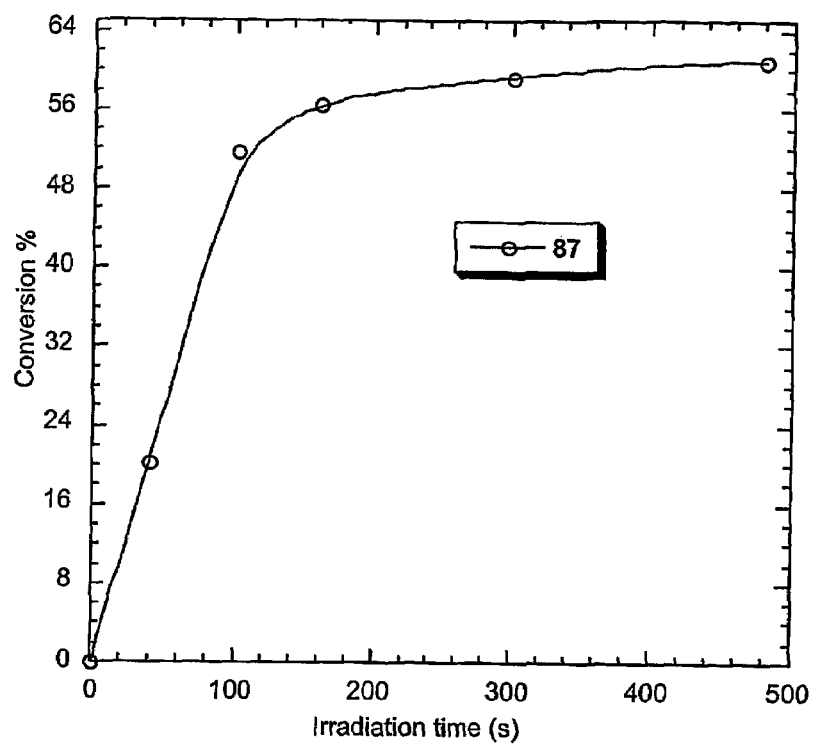
Figure 5. Conversion of epoxy acrylate CN-115 initiated by 87 monitored by IR at 810 cm$^{-1}$. Solvent: MeCN, 20% w.t. of CN115; 2% w.t. of CN115

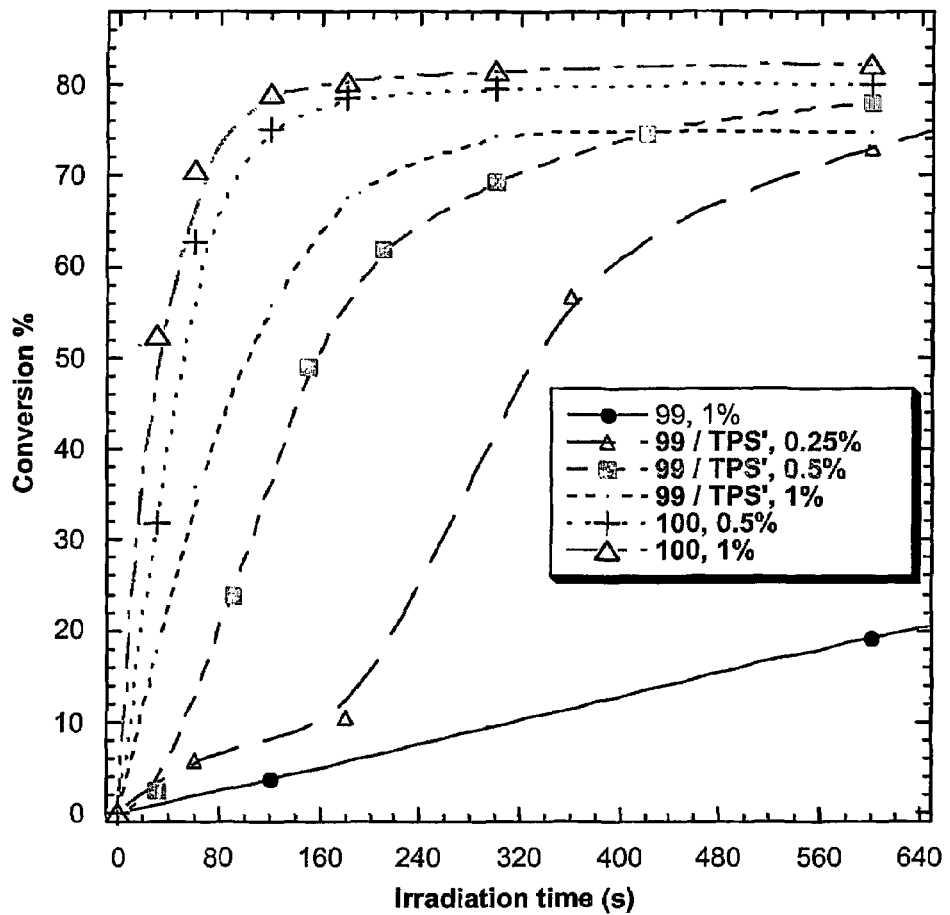
Figure 6a. Conversion of epoxy acrylate CN-115 initiated by different piperazine stilbene systems monitored by IR Solvent: Tetrahydrofuran 20% w.t. of CN115

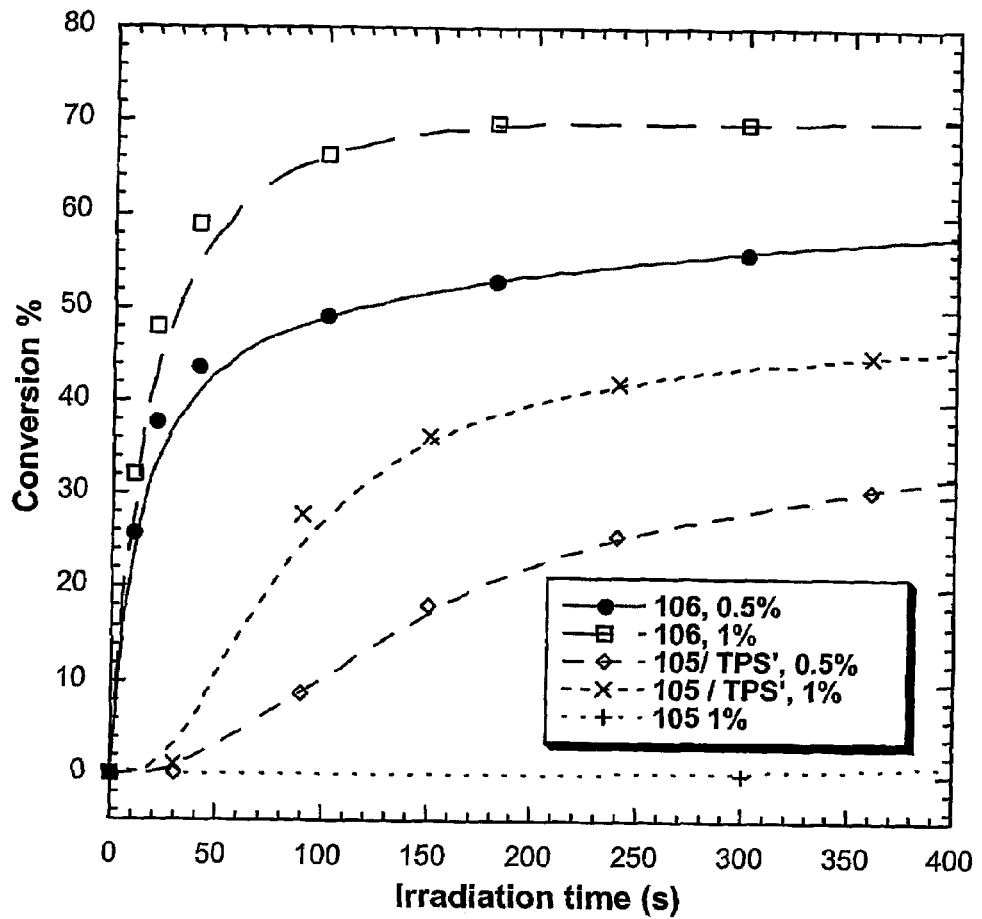
Figure 6b. Conversion of epoxy acrylate CN-115 initiated by different piperazine bistyrylbenzene systems monitored by IR Solvent: Tetrahydrofuran 20% w.t. of CN115

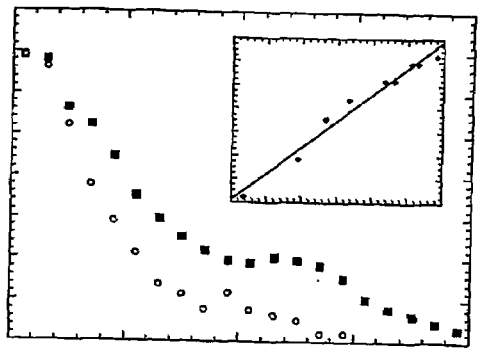

Figure 7. TPE (■) and relative acid-yield efficiency spectrum (○) of 41 in acetonitrile (4.0 × $10^{-4}$ M). $\delta$ is given in units of GM = 1 × $10^{-50}$ $cm^4$ s $photon^{-1}$. The inset is a plot of log[$H^+$] against log[excitation power/mW] at 745 nm. The smooth curve is the best fit of a line to the data and has a slope of 2.3.

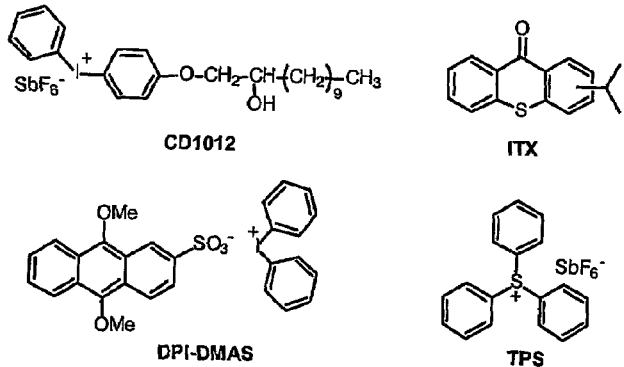

Figure 8. Structures of some conventional photoacid generators. CD1012 = [4-[(2-hydroxytetradecyl)oxy]phenyl]phenyliodonium hexafluoroantimonate (Sartomer), ITX = isopropylthioxanthone, DPI-DMAS = diphenyliodonium 9,10-dimethoxyanthracenesulfonate, TPS = triphenylsulfonium hexafluoroantimonate.

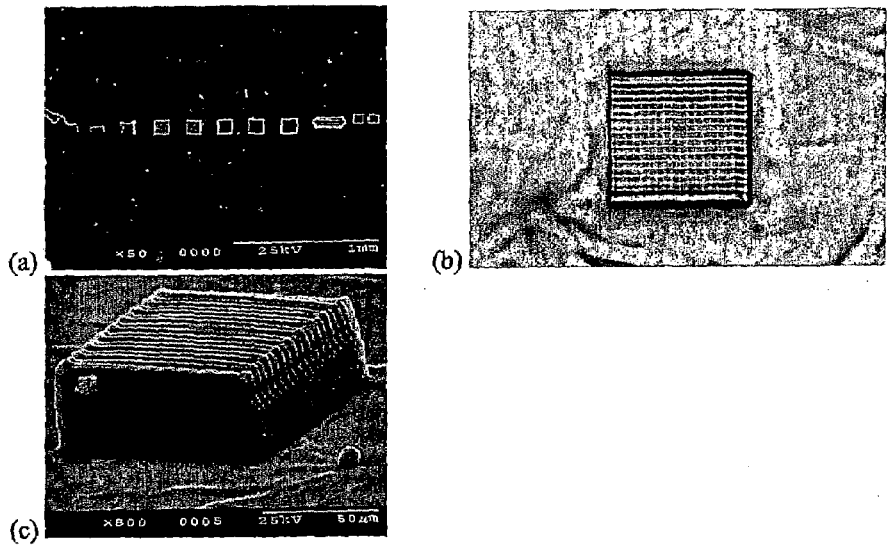

Figure 9. Images of microstructures created by patterned two-photon irradiation of an epoxide resin containing the compound 41. (a). Scanning electron micrograph (SEM) of microstructures created with average exposure powers of 1 - 5 mW. (b). Optical transmission micrograph of a "stack-of-logs" photonic bandgap structure fabricated with an average power of 3.5 mW. (c). SEM of the microstructure shown in (b).

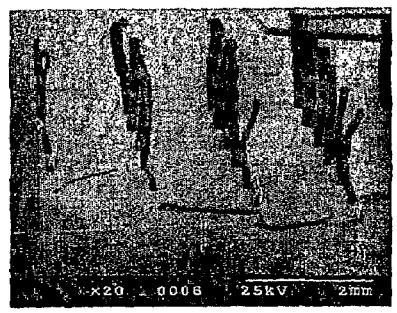

Figure 10. Scanning electron micrograph of free-standing columnar features formed two-photon-induced polymerization of a liquid epoxide resin containing 41.

MATERIALS, METHODS, AND USES FOR PHOTOCHEMICAL GENERATION OF ACIDS AND/OR RADICAL SPECIES

CROSS REFERENCE TO RELATED APPLICATIONS

This application claims the benefit of U.S. Provisional Application No. 60/280,672, filed Mar. 30, 2001, the entire contents of which are hereby incorporated by reference.

STATEMENT REGARDING FEDERALLY SPONSORED RESEARCH

The invention was partially supported by the United States Government through the National Science Foundation (Grant No. CHE9408701) and the Office of Naval Research (ONR Grant No. N00014-95-1-1319).

BACKGROUND OF THE INVENTION

1. Field of the Invention

The invention relates to compositions and compounds that have large two-photon or higher-order absorptivities, which, after excitation, generate Lewis or Brønsted acids, radicals or a combination thereof The invention also relates to methods of making and using the compositions and compounds.

2. Discussion of the Background

Two-photon or higher-order absorption refers to the initial simultaneous absorption of two or more photons (also referred to as multi-photon absorption) without the actual population of an excited state by the absorption of a single photon.

Molecular two-photon absorption was predicted in Göppert-Mayer, M., *Ann. Phys.* 1931, 9, 273. Upon the invention of pulsed ruby lasers in 1960, experimental observation of two-photon absorption became reality. In the years since, multi-photon excitation has found application in biology and optical data storage, as well as in other fields.

Although interest in multi-photon excitation has exploded, there is a paucity of two-photon absorbing dyes with adequately strong two-photon absorption in the correct spectral region for many applications.

There are two key advantages of two-photon (or higher-order) induced processes relative to single-photon induced processes. Whereas single-photon absorption scales linearly with the intensity of the incident radiation, two-photon absorption scales quadratically. Higher-order absorptions will scale with yet a higher power of incident intensity. As a result, it is possible to perform multi-photon induced processes with three dimensional spatial resolution. Further, because these processes involve the simultaneous absorption of two or more photons, the chromophore is excited with a number of photons whose total energy equals the energy of a multi-photon absorption transition, although each photon individually has insufficient energy to excite the chromophore. Because the exciting light is not attenuated by single-photon absorption in this case, it is possible to excite selectively molecules at a greater depth within a material than would be possible via single-photon excitation by use of a beam that is focused to that depth in the material. These two advantages also apply to, for example, excitation within tissue or other biological materials. In multi-photon lithography or stereolithography, the nonlinear scaling of absorption with intensity can lead to the ability to write features of a size below the diffraction limit of light, and the ability to write features in three dimensions, which is also of interest for holography.

The ability to realize many of the possible applications of two-photon or higher-order absorption by molecules rests on the availability of chromophores with large two-photon or higher-order absorption cross sections. We have taught in U.S. Pat. No. 6,267,913, which is incorporated herein by reference, that certain classes of molecules exhibit enhanced two-photon or multi-photon absorptivities. These molecules can be categorized as follows:

a) molecules in which two donors are connected to a conjugated π-electron bridge (abbreviated "D-π-D" motif);

b) molecules in which two donors are connected to a conjugated π-electron bridge which is substituted with one or more electron accepting groups (abbreviated "D-A-D" motif);

c) molecules in which two acceptors are connected to a conjugated π-electron bridge (abbreviated "A-π-A" motif); and d) molecules in which two acceptors are connected to a conjugated π-electron bridge which is substituted with one or more electron donating groups (abbreviated "A-D-A" motif).

Accordingly, molecules from the aforementioned classes can be excited efficiently by simultaneous two-photon (or higher-order) absorption, leading to efficient generation of electronically excited states. These excited state species can be exploited in a great variety of chemical and physical processes, with the advantages enabled by multiphoton excitation. For example, by employing polymerizable resin formulations containing cross-linkable acrylate containing monomers and D-π-D molecules as two-photon initiators of radical polymerization, complex three-dimensional objects can be prepared using patterned two-photon excitation. Most two-photon induced photopolymerization processes involve radical reactions in which there is some volume decrease upon polymerization (Cumpston et al. Nature 398, (1999) 51; Belfield, K. D. et al. J. Am. Chem. Soc. 122, (2000) 1217).

The applications that depend upon two-photon or multi-photon excitation also require that the two-photon or multiphoton excited states cause a chemical or physical change in the exposed region of the materials. Such changes can result from the generation of a Brønsted or Lewis acid and/or radical species and subsequent further reactions of that species with other components in the material, for example, resulting in cleavage of a functional group from a polymer or initiation of a polymerization, as is well known to one skilled in the art of lithography.

Under one photon excitation conditions it has been shown that sulfonium and iodonium salts are effective for the generation of Brønsted acids. Methods for the synthesis of sulfonium salts are well documented in J. L. Dektar and N. P. Hacker, "Photochemistry of Triarylsulfonium Salts", J. Am. Chem. Soc. 112, (1990) 6004-6015 which are incorporated herein by reference. Additional methods for synthesizing onium salts of the the general type described in the invention can be prepared conveniently from aryl aliphatic sulfides and primary aliphatic halides or benzyl halides, by well known methods such as those described in Lowe, P. A., "Synthesis of Sulfonium Salts", The Chemistry of the Sulfonium Group (Part 1), ed. C. J. M. Sterling, John Wiley & Sons, Ltd., (1981), p 267 et seq and as described in U.S. Pat. Nos. 5,302, 757, 5,274,148, 5,446,172, 5,012,001, 4,882,201, 5,591011, and 2,807,648, which are all incorporated herein by reference. Methods for the synthesis of iodonium salts are well documented in C. Herzig and S. Scheiding, DE 4,142,327, CA 119,250,162 and C. Herzig, EP 4,219,376, CA 120,298, 975 and U.S. Pat. Nos. 5,079,378, 4,992,571, 4,450,360, 4,399,071, 4,310,469, 4,151,175, 3,981,897, and 5,144,051 which are incorporated herein by reference.

It is known to those skilled in the art that epoxide-containing monomers exhibit relatively small shrinkage upon polymerization. It is also known that expoxide monomers as well as others, such as vinyl ether monomers, can be photo-polymerized under one photon excitation conditions using iodonium salts and sulfonium salts as photoacid generating initiators as described by: Crivello, J. V.; Lam, J. H. W. Macromolecules, 1977, 10, 1307; DeVoe, R. J.; Sahyn, M. R. V.; Schmidt, E. Can. J. Chem. 1988, 66, 319; Crivello, J. V.; Lee, J. J. Polym. Sci. Polym. Chem. Ed. 1989, 27 3951; Dektar, J.; Hacker, N. P. J. Am. Chem. Soc. 1990, 112, 6004; Crivello, J. V.; Lam, J. H. W.; Volante, C. N. J. Rad. Curing, 1977, 4, 2; Pappas, S. P.; Pappas, B. C.; Gatechair, L. R.; Jilek, J. H. Polym. Photochem. 1984, 5, 1; Welsh, K. M.; Dektar, J. L.; Garcia-Garibay, M. A.; Hacker, N. P.; Turro, N. J. J. Org. Chem. 1992, 57, 4179; Crivello, J. V.; Kong, S. Macromolecules, 2000, 33, 825, which are incorporated herein by reference.

It is known that dialkyl aryl sulfonium ions—as described by Saeva, F. D.; Morgan, B. P. J. Am. Chem. Soc., 1984, 106, 4121; Saeva, F. D. Advances in Electron Transfer Chem. 1994, 4, 1, which are incorporated herein by reference—and iodonium salts can be sensitized through electron transfer by the addition of other molecules. These include Class I and Class II photoacid generating species, as described by Saeva et al. (cited above).

SUMMARY OF THE INVENTION

One object of the invention is to provide compounds and compositions which can be efficiently photoactivated by two- or multi-photon excitation to yield acid and/or radical species and which consequently overcome the limitations associated with conventional compounds and compositions.

This and other objects have been achieved by the present invention, the first embodiment of which provides a compound or composition, which includes:
 at least one chromophore having a simultaneous two-photon or multi-photon absorptivity;
 at least one photoacid or radical generator in close proximity to the chromophore;
 wherein the generator may be a sulfonium, selenonium, or iodonium group, or other acid- or radical generating group. The present invention is not restricted to acid-generators consisting of only sulfonium, selenonium or iodonium groups.

Another embodiment of the present invention provides a method for making an article, which includes contacting the above compound or composition with at least one polymerizable or cross-linkable monomer, oligomer, or prepolymer, or acid-modifiable medium (such as ester-functionalized chemically amplified resins);
 irradiating the compound or composition to cause a simultaneous two-photon or multiphoton absorption in the chomophore; and
 polymerizing the monomer, oligomer, or prepolymer, or affecting a chemical change in an acid-modifiable medium. The invention can be used for the fabrication of articles by scanning of a focused laser beam or by multiple-beam interference.

Another embodiment of the present invention provides an article, produced by the above process.

Another embodiment of the present invention provides a method for generating a Brønsted or Lewis acid and/or radical, which includes irradiating the above compound or composition to cause a simultaneous two-photon or multiphoton absorption in the chomophore.

Another embodiment of the present invention provides a compound or composition, which includes:
 a first means for simultaneously absorbing two or more photons;
 a second means for producing an electronically excited state upon simultaneous absorption of two or more photons;
 a third means for generating a Brønsted or Lewis acid and/or radical upon reaction with the excited state;
 wherein the third means includes at least one sulfonium, selenonium, or iodonium group, or other acid- or radical generating group.

Another embodiment of the present invention provides an apparatus, which includes:
 a compound or composition, which includes:
  a first means for simultaneously absorbing two or more photons;
  a second means for producing an electronically excited state upon simultaneous absorption of two or more photons;
  a third means for generating a Brønsted or Lewis acid and/or radical upon reaction with the excited state;
  wherein the third means includes at least one sulfonium, selenonium, or iodonium group, or other acid- or radical generating group; and
 a means for irradiating the compound or composition.

BRIEF DESCRIPTION OF THE FIGURES

A more complete appreciation of the invention and many of the attendant advantages thereof will be readily obtained as the same becomes better understood by reference to the following detailed description when conisidered in connection with the accompanying drawings.

FIG. 1. Two-photon dye covalently attached to a photoacid.

FIG. 2. Two-photon dye non-covalently attached to a photoacid.

FIG. 3. Photopolymerization kinetics of cyclohexene oxide initiated by different triphenylamine sulfonium salts in dichloromethane irradiated at 300 nm. Concentration of monomer: 7.91 mol/L; concentration of initiator: $3.16 \times 10^{-3}$ mol/L. Lines are a guide to the eye.

FIG. 4. Photopolymerization initiated by different initiators in $CH_2Cl_2$ at 419 nm [monomer]: 7.906 mol/L; [initiator]: $7.906 \times 10^{-3}$ mol/L.

FIG. 5. Conversion of epoxy acrylate CN-115 initiated by 87 monitored by IR at 810 $cm^{-1}$. Resin: MeCN, 20% w.t. of CN115; 87, 2% w.t. of CN115.

FIG. 6a Conversion of epoxy acrylate CN-115 initiated by different piperazine stilbene systems monitored by IR Solvent: Tetrahydrofuran 20% w.t. of CN115.

FIG. 6b. Conversion of epoxy acrylate CN-115 initiated by different piperazine bistyrylbenzene systems monitored by IR Solvent: Tetrahydrofuran 20% w.t. of CN115.

FIG. 7. TPE (■) and relative acid-yield efficiency spectrum (○) of 41 in acetonitrile ($4.0 \times 10^{-4}$ M). δis given in units of $GM = 1 \times 10^{-50}$ $cm^4$ s $photon^{-1}$. The inset is a plot of log [$H^+$] against log [excitation power/mW] at 745 nm. The smooth curve is the best fit of a line to the data and has a slope of 2.3.

FIG. 8. Structures of some conventional PAGs. CD1012= [4-[(2-hydroxytetradecyl)oxy]phenyl]phenyliodonium hexafluoroantimonate (Sartomer), ITX=isopropylthioxanthone, DPI-DMAS diphenyliodonium 9,10-dimethoxyanthracenesulfonate, TPS triphenylsulfonium hexafluoroantimonate.

FIG. 9. Images of microstructures created by patterned two-photon irradiation of an epoxide resin containing the compound 41. (a). Scanning electron micrograph (SEM) of microstructures created with average exposure powers of 1-5 mW. (b). Optical transmission micrograph of a "stack-of-logs" photonic bandgap structure fabricated with an average power of 3.5 mW. (c). SEM of the microstructure shown in (b).

FIG. 10. Scanning electron micrograph of free-standing columnar features formed by two-photon-induced polymerization of a liquid epoxide resin containing 41.

DESCRIPTION OF THE PREFERRED EMBODIMENTS

Various other objects, features and attendant advantages of the present invention will be more fully appreciated as the same becomes better understood from the following detailed description of the preferred embodiments of the invention.

Here we teach that compounds preferably derived from TPA dyes, such as D-π-D, D-A-D and A-D-A as described above, but in which the dye skeleton is fìnctionalized with a group capable of generating a Lewis or Brønsted Acid and/or radical after excitation of the dye moiety, can generate reactive species, and preferably acids or radical species. In particular, dyes containing either a sulfonium group or an iodonium group in a single molecule can be effective at generating Lewis or Brønsted Acids (and/or radicals) under one, two, or higher order photon excitation. These acids or radicals can subsequently react with additional species in a beneficial manner. For example, these materials can be used beneficially as one or two-photon initiators for polymerization of expoxide containing monomers. These compounds exhibit enhanced two-photon or multi-photon absorptivities and allow one to control the position of two-photon or multi-photon absorption bands.

To ensure a more complete understanding of the invention, the following definitions are preferred:

By the term "bridge", it is meant a molecular fragment that connects two or more chemical groups.

By the term "donor", it is meant an atom or group of atoms with a low ionization potential that can be bonded to a π-conjugated bridge. Exemplary donors, in order of increasing strength, are (where R denotes an alkyl, aryl, or alkoxy group as defined below, where X(O) indicates that the element oxygen is double bonded to the element X, and where * indicates the point of attachment to the π-conjugated bridge):

I<Br<Cl<F<OC(O)R<SH<OH<SR<OR<NHC(O)R<NH$_2$<NHR<NR$_2$<S$^-$<O$^-$.

Other donors that have donating strength greater than SR include:

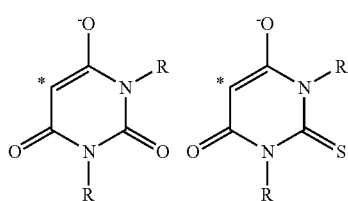

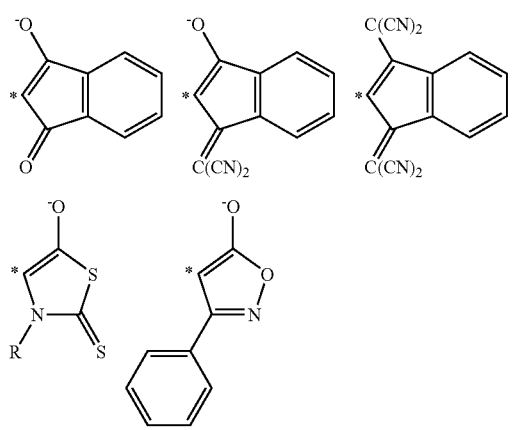

By the term "acceptor", it is meant an atom or group of atoms with a high electron affinity that can be bonded to a π-conjugated bridge. Exemplary acceptors, in order of increasing strength, are (where R denotes an alkyl, aryl, or alkoxy group as defined below, where X(O) indicates that the element oxygen is double bonded to the element X, and where * indicates the point of attachment to the π-conjugated bridge):

C(O)NR$_2$<C(O)NHR<C(O)NH$_2$<C(O)OR<C(O)OH<C(O)R<C(O)H<CN<S(O$_2$)R<NO$_2$.

Other acceptors that have accepting strength greater than C(O)R include (where R denotes an alkyl, aryl, or alkoxy group as defined below):

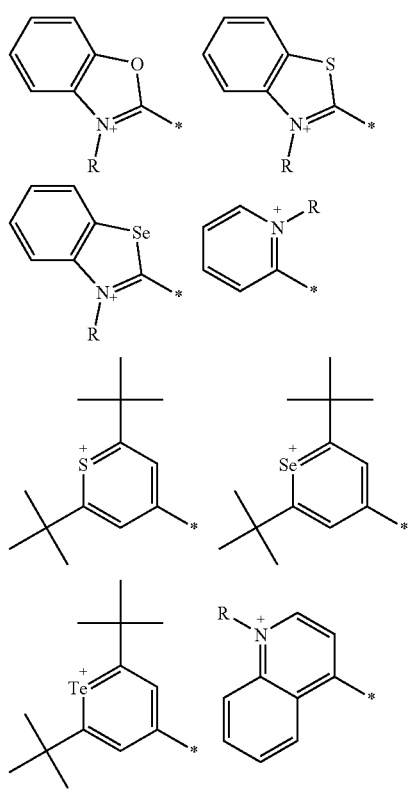

-continued
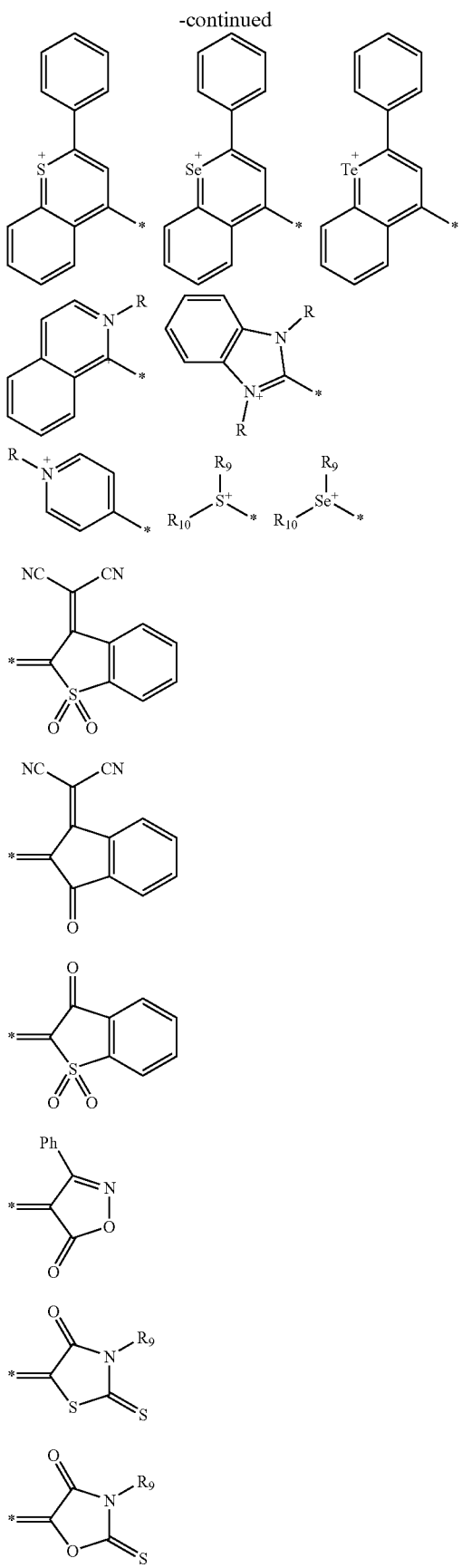
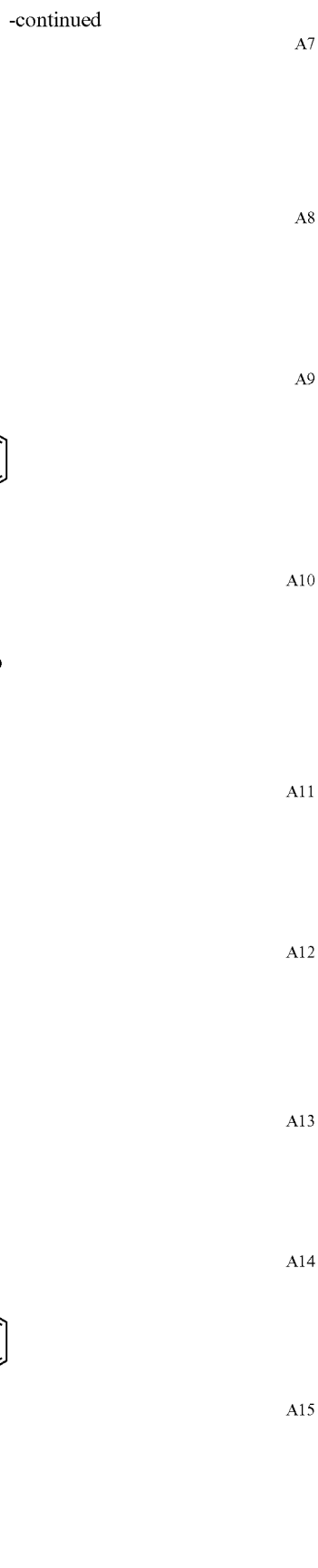

-continued
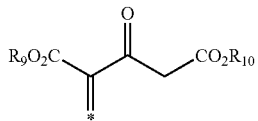
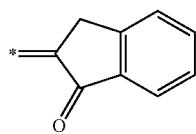
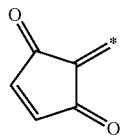
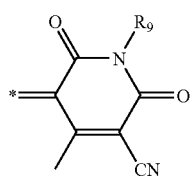
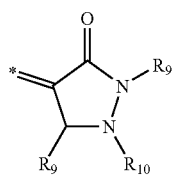
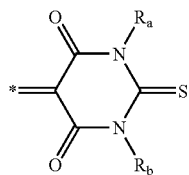
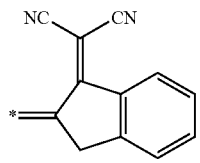
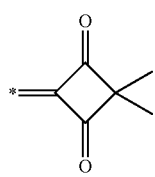
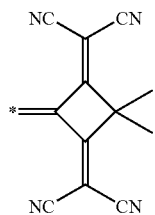
-continued
A16 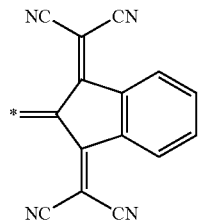
A17
A18 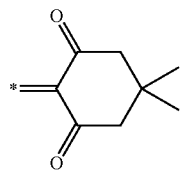
A19 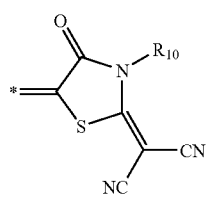
A20 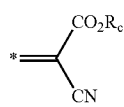
A21 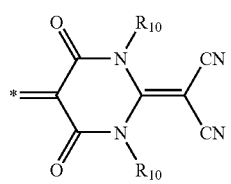
A22 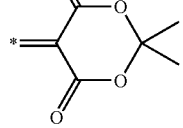
A23
A24
A25
A26
A27
A28
A29
A30 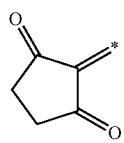
A31 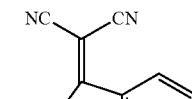
A32 
A33

-continued

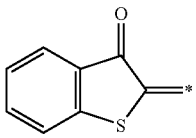 A34

 A35

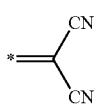 A36

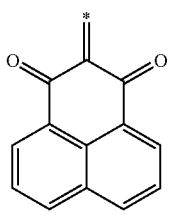 A37

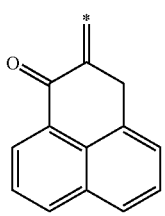 A38

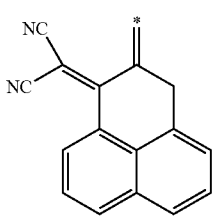 A39

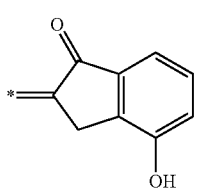 A40

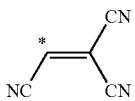 A41

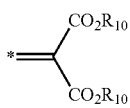 A42

A more complete discussion of what is meant by electron donors or donating groups and electron acceptors or electron accepting groups may be found in J. March, *Advanced Organic Chemistry: Reactions, Mechanisms and Structure,* Fourth edition, Wiley-Interscience, New York, 1992, Chapter 9, which is incorporated herein by reference.

By the phrase "aromatic group", it is meant a carbocyclic group that contains 4n+2 π-electrons where n is an integer (and which may preferably have values of 1, 2, 3, 4, 5, 6, 7, 8, 9, 10, 11, 12, 13, 14, 15, 16, 17, 18, 19, 20, 21, 22, 23, and 24). Exemplary aryl groups include phenyl, naphthyl anthracenyl, and pyrenyl.

By the phrase "heteroaromatic group", it is meant a cyclic group of atoms, with at least one atom within the ring being an element other than carbon, that contains 4n+2 π-electrons where n is an integer (and which may preferably have values of 1, 2, 3, 4, 5, 6, 7, 8, 9, 10, 11, 12, 13, 14, 15, 16, 17, 18, 19, 20, 21, 22, 23, and 24). Exemplary heteroaromatic groups include furanyl, thiophenyl, pyrrolyl, selenophenyl and tellurophenyl. A more complete discussion of aromaticity and heteroaromaticity can be found in J. March, *Advanced Organic Chemistry: Reactions, Mechanisms and Structure,* Fourth edition, Wiley-Interscience, New York, 1992, Chapter 2, which is incorporated herein by reference.

By the term "chromophore", it is meant a molecule or aggregate of molecules that can absorb electromagnetic radiation.

By the term "simultaneous", it is meant that two events that occur within the period of $10^{-14}$ sec or less.

By the phrase "excited state", it is meant an electronic state of a molecule wherein electrons populate an energy state that is higher than another energy state for the molecule.

By the phrase "two-photon absorption", it is meant the process wherein a molecule is promoted to an excited state by the simultaneous absorption of two quanta of electromagnetic radiation.

By the phrase "multi-photon absorption", it is meant a process wherein a molecule absorbs is promoted to an excited state by the simultaneous absorption of two or more quanta of electromagnetic radiation.

A "π-conjugated bridge" contains covalent bonds between atoms that both have σ-(sigma) and π-bonds formed between two atoms by overlap of their atomic orbitals (s+p hybrid atomic orbitals for σ bonds; p atomic orbitals for r bonds) with two orbitals ($sp^3$, $sp^2$, sp) overlapping end-to-end to form a σ bond lying directly between the nuclei.

In particular, when two p orbitals are standing perpendicular to the σ-bonded skeleton and overlapping sideways, a π-bond is formed. When there are adjacent p orbitals on each side of an atom, and they overlap with the p orbital on that atom, a situation is created such that a more extended π-orbital is formed in which the electrons in the orbital are no longer confined between two atoms, but rather are delocalized over a greater number of nuclei. For this to occur, each successive atom bearing a p orbital for overlap must be adjacent to the last. (Sideways overlap of p orbitals is not significant for atoms more than a bond length apart, that is, ~1.5 Å.)

This delocalization of π-electrons is of central importance to the chemical and physical properties of unsaturated molecules. In particular, a π-conjugated bridge is one having a formal structure that contains double or triple bonds alternating with single bonds where the double and triple bonds are capable of further π overlap with each other. Such bridges are said to be π-conjugated and include conjugated double or triple bonds.

By the phrase, "heterolytic cleavage", it is meant the fragmentation of a two-electron chemical bond such that the two electrons that composed the bond both reside on one of the two fragments formed.

A more complete discussion of aromaticity and heteroaromaticity can be found in J. March, *Advanced Organic Chemistry. Reactions, Mechanisms and Structure, Fourth edition,* Wiley-Interscience, New York, 1992. page 205.

By the phrase, "homolytic cleavage", it is meant the fragmentation of a two-electron chemical bond such that each of the two fragments formed is formed with one of the two electrons that composed the bond.

A Brønsted acid is a proton or a proton donor.

A Lewis acid is a species that is electron deficient and behaves as an electron acceptor.

A resin is a mixture of materials and/or compounds at least one of which is capable of undergoing a chemical reaction that can change the physical properties of the mixture. For example, it can render the mixture less soluble or more soluble in a solvent.

A radical is a species that possesses one or more unpaired electrons.

A binder is a material and/or compound, which is a component of a resin, and which can increase the viscosity of the resin to such a point that the resin can be conveniently cast into a film under suitable processing conditions.

Photochemical hardening is a process in which the viscosity of solubility of a material increases upon exposure to electro-magnetic radiation, preferably from wavelengths of 100 nm to 1600 nm.

A negative resist is a resin whose solublity, in a given solvent, decreases upon exposure to electromagnetic radiation, preferably from wavelengths of 100 nm to 1600 nm.

A positve resist is a resin whose solublity, in a given solvent, increases upon exposure to electromagnetic radiation, preferably from wavelengths of 100 nm to 1600 nm.

By the phrase, "photochemically effective amounts", it is meant that the components of the photoinitiator system are present in amounts sufficient for the resin to undergo photochemical hardening upon exposure to light of the desired wavelength.

By radical generator it is meant a species that generates a radical following an activation process. Such activation processes can include, but are not limited to the following: heating; direct photoexcitation of the radical generator; indirect activation of the radical generator by energy transfer from another photoexcited species; transfer of an electron to or from the radical generator.

By photo-activated radical generator it is meant a group that upon exposure to electromagnetic radiation generates a radical. Examples of photo-activated radical generators include, but are not limited to the following species: Some examples of radical generators include: arylborate anions in the presence of a photosensitizer; benzoin; benzophenone; sulfonium ions; iodonium ions; acylphosphine oxides. Further examples of photo-activated radical generators can be found in: R. S. Davidson, J. Photochem. Photobiol. A: Chem. vol. 73 (1993) pp. 81-96; U.S. Pat. Nos. 6,335,144, 6,316, 519, 6,296,986, 6,294,698, 6,287,749, 6,265,458, 6,277,897, 6,090,236; and patents cited therein, which are incorporated herein be reference.

By an acid generator it is meant a species that generates a Brønsted or Lewis acid following an activation process. Such activation processes can include, but are not limited to the following: heating; direct photoexcitation of the acid generator; indirect activation of the acid generator by energy transfer from another photoexcited species; transfer of an electron to or from the acid generator.

By photoacid generator it is meant a group that upon exposure to electromagnetic radiation generates a Brønsted or Lewis acid. Examples of photoacid generators include, but are not limited to the following species: sulfonium, selenonium, and iodinium salts, arene-iron cyclopentadienyl complexes, 4-nitrobenzylsulfonates and perfluorobenzylsulfonates (Shirai, M.; Tsunooka, M. Prog. Polym. Sci. 1996, 21, 1); dialkylphenacylsulfonium salts and 3,5-dialkyl-4-hydroxyphenyl sulfonium salts (Crivello, J. V.; Lee, J. L. Macromol. 1981, 14, 1141).

The present invention provides for compounds and/or compositions that have large two-photon or higher-order absorptivities, and which yield Lewis or Brønsted acids (and/or radicals) after multi-photon excitation. It is preferable in the general design scheme of this invention that a multi-photon-excitable chromophore fragment and an acid-generating group are held in close proximity to one another (at a distance that is less than or equal to 20 Å). This can be achieved by connecting the chromophore and the acid generator using a covalent linkage, as illustrated in FIG. 1. However, the invention is not limited to compositions of matter involving only a covalent linkage of the chromophore and acid generator. Any mechanism that keeps the chromophore and the acid generator in close proximity is suitable, and this generalized design scheme is illustrated in FIG. 2. The association mechanisms for the design scheme of FIG. 2 can include, but are not limited to, ion-pairing effects, hydrogen-bonding, charge-transfer complex formation, perfluoroaryl-aryl electrostatic interactions, π-stacking associations, coordinative-bond formation, and dipole-dipole pairing.

In compositions wherein the chromophore and the acid generator are covalently linked, the molecule may be any two-photon dye skeleton, such as D-π-D, A-π-A, D-A-D or A-D-A, as described in U.S. Pat. No. 6,267,913, that is further derivatized with at least one photoacid generator or radical generator, such as either a sulfonium or an iodonium group. Moreover, and preferably, the molecules of the invention can be described as a two-photon dye skeleton of the form D-π-D, A-π-A, D-A-D or A-D-A, that may have the following substituents:

i. alkyl: a linear or branched saturated hydrocarbon group with up to 25 carbons; $-(CH_2CH_2O)_\alpha-(CH_2)_\beta OR_{a1}$; $-(CH_2CH_2O)_\alpha-(CH_2)_\beta NR_{a2}R_{a3}$; $-(CH_2CH_2O)_\alpha-(CH_2)_\beta CONR_{a2}R_{a3}$; $-(CH_2CH_2O)_\alpha-(CH_2)_\beta CN$; $-(CH_2CH_2O)_\alpha-(CH_2)_\beta Cl$; $-(CH_2CH_2O)_\alpha-(CH_2)_\beta Br$; $-(CH_2CH_2O)_\alpha-(CH_2)_\beta I$; or $-(CH_2CH_2O)_\alpha-(CH_2)_\beta$-Phenyl, where $R_{a1}$, $R_{a2}$, and $R_{a3}$ are independently either H or a linear or branched hydrocarbon group with up to 25 carbons, $\alpha$ is 0-10 and $\beta$ is 1-25 (which ranges include all values and subranges therebetween, including 1, 2, 3, 4, 5, 6, 7, 8, 9, 10, 11, 12, 13, 14, 15, 16, 17, 18, 19, 20, 21, 22, 23, 24 and 25 as appropriate);

ii. alkoxy: $OR_{a4}$, where $R_{a4}$ can be either alkyl, aryl, sulfonium, iodonium, or monomer as described below;

iii. monomer and pre-polymer substituents: such as those which could contain, but are not limited to vinyl; allyl; 4-styryl; acrylate; methacrylate; acrylonitrile; dicyclopentadiene; norbornene; cyclobutene; epoxides (e.g. cyclohexene oxide, propene epoxide; butene epoxide, vinyl cyclohexene diepoxide); vinyl ethers; $-(CH_2)_\delta SiCl_3$; $-(CH_2)_\delta Si(OCH_2CH_3)_3$; or $-(CH_2)_\delta Si(OCH_3)_3$, where $\delta$ is 0-25 (which range includes all values and sub-ranges therebetween, including 0, 1, 2, 3, 4, 5, 6, 7, 8, 9, 10, 11, 12, 13, 14, 15, 16, 17, 18, 19, 20, 21, 22, 23, 24, and 25); (further examples of monomer and pre-polymer functionalities which may be pendant on the two-photon dye skeleton can be found in U.S. Pat. Nos. 5,463,084, 5,639,413, 6,268,403, 4,689,289, 4,069,056, 4,102,687, 4,069,055, 4,069,056, 4,058,401, 4,058,400, 5,086,192, 4,791,045, 4,090,936, 5,102,772, and 5,047, 568, and patents cited therein, which are incorporated herein by reference); or iv. aryl: up to a 20-membered aromatic or heteroaromatic ring system (which range includes all values and subranges therebetween, including 3, 4, 5, 6, 7, 8, 9, 10, 11, 12, 13, 14, 15, 16, 17, 18, 19, and 20 as appropriate), where the rings can be substituted independently further with H, alkyl, monomer or pre-polymer substituents as defined above, sulfonium, selenonium, iodonium, or other acid or radical generating group, as described below;

and the molecules must have at least one of the following:

v. sulfonium: —$(CH_2)_\gamma$—$(C_6H_4)_\delta$—$SR_{a5}R_{a6}$, where $R_{a5}$ and $R_{a6}$ can be independently alkyl, aryl, or monomer or pre-polymer, and $\gamma=0$ to 25, and $\delta=0$ to 5 and the entire group carries an overall positive charge (these ranges include all values and subranges therebetween, including 0, 1, 2, 3, 4, 5, 6, 7, 8, 9, 10, 11, 12, 13, 14, 15, 16, 17, 18, 19, 20, 21, 22, 23, 24, and 25 as appropriate).

vi. selenonium: —$(CH_2)_\gamma$—$(C_6H_4)_\delta$—$SeR_{a5}R_{a6}$, where $R_{a5}$ and $R_{a6}$ can be independently alkyl, aryl, or monomer or pre-polymer, and $\gamma=0$ to 25, and $\delta=0$ to 5 and the entire group carries an overall positive charge (these ranges include all values and subranges therebetween, including 0, 1, 2, 3, 4, 5, 6, 7, 8, 9, 10, 11, 12, 13, 14, 15, 16, 17, 18, 19, 20, 21, 22, 23, 24, and 25 as appropriate).

vii. iodonium: —$(CH_2)_\gamma$—$(C_6H_4)_\delta$—$IR_{a7}$, where $R_{a7}$ can be independently alkyl, aryl, or monomer or pre-polymer, and $\gamma=0$ to 25, and $\delta=0$ to 5 and the entire group carries an overall positive charge (these ranges include all values and subranges therebetween, including 0, 1, 2, 3, 4, 5, 6, 7, 8, 9, 10, 11, 12, 13, 14, 15, 16, 17, 18, 19, 20, 21, 22, 23, 24, and 25 as appropriate).

viii. one of several other acid- or radical-generating functionalities as described below. These could include, but are not limited to, the following examples: oxoniums, diarylchloroniums, diarylbromoniums, onium bicarbonates, nitrobenzylcarbonate esters, 4-nitrobenzylsulfonates, perfluorobenzylsulfonates, dialkylphenacylsulfonium salts, 3,5-dialkyl-4-hydroxyphenyl sulfonium, sulfones, disulfones, arylphosphates, cyclopentadienyliron arene complexes.

For the onium functionalities of (ii)-(vii), one or more of the substituents pendant on the onium center (e.g. O, S, Se, I) may be part of a fused-ring structure, and two or more of the substituents may be joined through such a fused ring structure. Note that composition of matter numbers 84 and 87 (described below), are some preferred examples of such fused-ring onium photoacid generators.

Since the cationic selenonium, sulfonium or iodonium moieties are essential, the molecules of the invention preferably also have an anion to provide electroneutrality. Preferred examples of anions include: $F^-$, $Cl^-$, $Br^-$, $I^-$, $CN^-$, $SO_4^{2-}$, $PO_4^{3-}$, $CH_3CO_2^-$, $CF_3SO_3^-$, $NO_2^-$, $NO_3^-$, $BF_4^-$, $PF_6^-$, $SbF_6^-$, $AsF_6^-$, $SbCl_4^-$, $ClO_3^-$, $ClO_4^-$, $C(aryl)_4^-$ where aryl is an aryl group containing 25 or fewer carbon atoms (which range includes all values and subranges therebetween, including 3, 4, 5, 6, 7, 8, 9, 10, 11, 12, 13, 14, 15, 16, 17, 18, 19, 20, 21, 22, 23, 24, and 25 as appropriate) and can be additionally substituted with one or more alkyl groups, aryl groups or halogens, for example, $B(C_6H_5)_4^-$, or $B(C_6F_5)_4^-$. In the preferred embodiment of the invention, the photoacid molecules will contain anions that are very weak Lewis bases that are effectively non-coordinating, such as $BF_4^-$, $PF_6^-$, $SbF_6^-$, $AsF_6^-$, $B(aryl)_4^-$ or $SbCl_4^-$. Preferably, the invention molecules may also have a zwitterionic structure, wherein anions (such as $B(aryl)_4^-$) are covalently bound to the cationic fragment, giving an overall electroneutral structure. Combinations of anions are possible.

In a preferred embodiment, the molecules of the invention should have the structure:

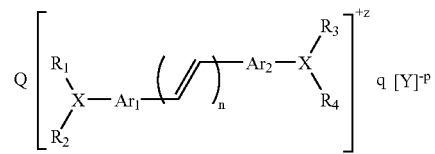

where X=S or Se and n=0, 1, 2, 3, 4, or 5. $Ar_1$ and $Ar_2$ can each independently be: a 5-membered heteroaromatic ring; a 6-membered aromatic ring; or a 6-membered heteroaromatic ring. $Ar_1$ and $Ar_2$ can each independently be substituted with one or more H, alkyl, alkoxy, or aryl, which itself can be further substituted with one or more sulfonium, selenonium, iodonium, other acid- or radical-generating species, or monomer or pre-polymer functionalities. $R_1$, $R_2$, $R_3$, and $R_4$ can be independently alkyl or aryl, which can be further substituted with sulfonium, selenonium, iodonium, other acid- or radical-generating species, or a monomer or pre-polymer functionality. Y is said counterion, and is one of the anions defined previously. The overall charge on the dye portion of the molecule is denoted by z. Integer p is the charge on the counterion, integers q and Q and are the number of anions and cations respectively in the empirical formula and are such that the quantity zQ=pq, where pq is a positive integer less than 9 (which range includes all values and subranges therein, including 1, 2, 3, 4, 5, 6, 7, and 8). The following are provided as illustrative examples, but are not limiting cases: z=1, Q=1, p=1, q=1, so pq=1; and z=2, Q=1, p=1, q=2, so pq=2.

For this composition and all compositions described hereafter (except where explicitly stated otherwise), the two or more substituents connected to a given aromatic ring may assume any substitution pattern. As an example, for the composition described immediately above, the substitution pattern of the fragments $R_1R_2X$ and the vinyl-group around $Ar_1$ may be ortho, meta, or para.

In another preferred embodiment, the molecules of the invention should have the structure:

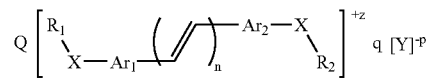

where X=I, and n=0, 1, 2, 3, 4, or 5. $Ar_1$ and Ar2 can each independently be: a 5-membered heteroaromatic ring; a 6-membered aromatic ring; or a 6-membered heteroaromatic ring. $Ar_1$ and $Ar_2$ can each independently be substituted with one or more H, alkyl, alkoxy, or aryl groups, which itself can be further substituted with one or more sulfonium, selenonium, iodonium, other acid- or radical-generating species, or monomer or pre-polymer functionalities. $R_1$ and $R_2$ can be independently alkyl or aryl, which can be further substituted with sulfonium, selenonium, iodonium, other acid- or radical-generating species, or a monomer or pre-polymer functionality. Y is said counterion, and is one of the anions defined previously. The overall charge on the dye portion of the molecule is denoted by z. Integer p is the charge on the counterion, integers q and Q and are the number of anions and cations respectively in the empirical formula and are such that the quantity zQ=pq, where pq is a positive integer less than 9 (which range includes all values and subranges therein, including 1, 2, 3, 4, 5, 6, 7, and 8). The following are provided as illustrative examples, but are not limiting cases: z=1, Q=1, p=1, q=1, so pq=1; and z=2,Q=1, p=1, q=2,so pq=2.

In another preferred embodiment, the molecules should have the general structure:

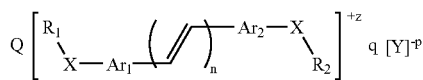

where X is O, where n=1, 2, 3, 4, or 5. $Ar_1$ and $Ar_2$ can each independently be: a 5-membered heteroaromatic ring; a 6-membered aromatic ring; or a 6-membered heteroaromatic ring. $Ar_1$ and $Ar_2$ can each independently be substituted with one or more H, allcyl, alkoxy, or aryl groups, which itself can be further substituted with one or more sulfonium, selenonium, iodonium, other acid- or radical-generating species, or monomer or pre-polymer functionalities. $R_1$ and $R_2$ can be independently H, alkyl or aryl, which can be further substituted with sulfonium, selenonium, iodonium, other acid- or radical-generating species, or a monomer or pre-polymer functionality. At least one of $Ar_1$, $Ar_2$, $R_1$ or $R_2$ must be substituted with a sulfonium, selenonium, or iodonium group, or other acid- or radical generating group. Y is said counterion, and is one of the anions defined previously. The overall charge on the dye portion of the molecule is denoted by z. Integer p is the charge on the counterion, integers q and Q and are the number of anions and cations respectively in the empirical formula and are such that the quantity zQ=pq, where pq is a positive integer less than 9 (which range includes all values and subranges therein, including 1, 2, 3, 4, 5, 6, 7, and 8). The following are provided as illustrative examples, but are not limiting cases: z=1, Q=1, p=1, q=1, so pq=1; and z=2, Q=1, p=1, q=2, so pq=2.

In another preferred embodiment, the molecules should have the general structure:

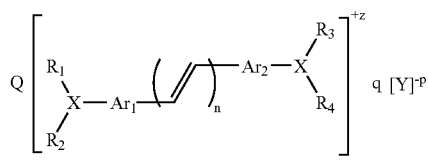

where X is N and n=0, 1, 2, 3, 4, or 5. $Ar_1$ and $Ar_2$ can each independently be: a 5-membered heteroaromatic ring; a 6-membered aromatic ring; or a 6-membered heteroaromatic ring. $Ar_1$ and $Ar_2$ can each independently be substituted with one or more H, alkyl, alkoxy, or aryl groups, which can be further substituted with sulfonium, selenonium, iodonium, other acid- or radical-generating species, or monomer or pre-polymer functionalities. $R_1$, $R_2$, $R_3$, and $R_4$ can be independently H, alkyl, or aryl, which can be further substituted with sulfonium, selenonium, iodonium, other acid- or radical-generating species, or a monomer or pre-polymer functionality. At least one of $Ar_1$, $Ar_2$, $R_1$, $R_2$, $R_3$, or $R_4$ must be substituted with a sulfonium, selenonium, or iodonium group, or other acid- or radical generating group. Y is said counterion, and is one of the anions defined previously. The overall charge on the dye portion of the molecule is denoted by z. Integer p is the charge on the counterion, integers q and Q and are the number of anions and cations respectively in the empirical formula and are such that the quantity zQ=pq, where pq is a positive integer less than 9 (which range includes all values and subranges therein, including 1, 2, 3, 4, 5, 6, 7, and 8). The following are provided as illustrative examples, but are not limiting cases: z=1, Q=1, p=1, q=1, so pq=1; and z=2, Q=1, p=1, q=2,so pq=2.

In another preferred embodiment, the molecules should have the structure:

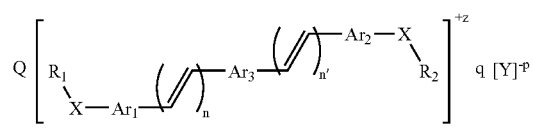

where X is I, n=0, 1, 2, 3, 4, or 5, and n'=0, 1, 2, 3, 4 or 5. $Ar_1$ and $Ar_2$ can each independently be: a 5-membered heteroaromatic ring; a 6-membered aromatic ring; or a 6-membered heteroaromatic ring. $Ar_3$ can be: a 5-membered heteroaromatic ring; a 6-membered aromatic ring; or a 6-membered heteroaromatic ring. $Ar_1$ and $Ar_2$ can each independently be substituted with one or more H, alkyl, alkoxy, or aryl groups, which can be further substituted with sulfonium, selenonium, iodonium, other acid- or radical-generating species, or monomer or pre-polymer functionalities. $Ar_3$ can be substituted with one or more H, acceptor, alkyl, alkoxy, or aryl groups, which can be further substituted with sulfonium, selenonium, iodonium, other acid- or radical-generating species, or monomer or pre-polymer functionalities. $R_1$ and $R_2$ can be independently: alkyl or aryl which can be further substituted with sulfonium, selenonium, iodonium, other acid- or radical-generating species, or monomer or pre-polymer functionalities. Y is said counterion, and is one of the anions defined previously. The overall charge on the dye portion of the molecule is denoted by z. Integer p is the charge on the counterion, integers q and Q and are the number of anions and cations respectively in the empirical formula and are such that the quantity zQ=pq, where pq is a positive integer less than 9 (which range includes all values and subranges therein, including 1, 2, 3, 4, 5, 6, 7, and 8). The following are provided as illustrative examples, but are not limiting cases: z=1, Q=1, p=1, q=1, so pq=1; and z=2, Q=1, p=1, q=2, so pq=2.

In another preferred embodiment, the molecules should have the structure:

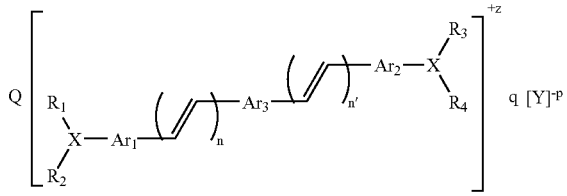

where X is S or Se, n=0, 1, 2, 3, 4, or 5, and n'=0, 1, 2, 3, 4 or 5. $Ar_1$ and $Ar_2$ can each independently be: a 5-membered heteroaromatic ring; a 6-membered aromatic ring; or a 6-membered heteroaromatic ring. $Ar_3$ can be: a 5-membered heteroaromatic ring; a 6-membered aromatic ring; or a 6-membered heteroaromatic ring. $Ar_1$ and $Ar_2$ can be substituted with one or more: H, alkyl, alkoxy, or aryl, which can be further substituted with sulfonium, selenonium, iodonium, other acid- or radical-generating species, or a monomer or pre-polymer functionality. $Ar_3$ can be substituted with: one or more H, acceptor, alkyl, alkoxy, or aryl, which can be further substituted with sulfonium, selenonium, iodonium, other acid- or radical-generating species, or a monomer or pre-polymer functionality. $R_1$, $R_2$, $R_3$, and $R_4$ can be independently: alkyl, or aryl, which can be further substituted with sulfonium, selenonium, iodonium, other acid- or radical-generating species, or a monomer or pre-polymer functionality. The overall charge on the dye portion of the molecule is denoted by z. Integer p is the charge on the counterion, integers q and Q and are the number of anions and cations respectively in the empirical formula and are such that the quantity zQ=pq, where pq is a positive integer less than 9 (which range includes all values and subranges therein, including 1, 2, 3, 4, 5, 6, 7, and 8). The following are provided as illustrative examples, but are not limiting cases: z=1, Q=1, p=1, q=1, so pq=1; and z=2, Q=1, p=1, q=2, so pq=2.

In another preferred embodiment, the molecules should have the structure:

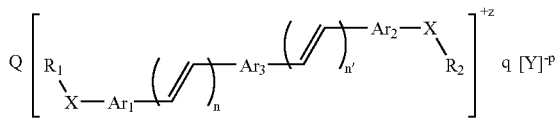

where X is O, n=0, 1, 2, 3, 4, or 5, and n'=0, 1, 2, 3, 4 or 5. $Ar_1$ and $Ar_2$ can each independently be: a 5-membered heteroaromatic ring; a 6-membered aromatic ring; or a 6-membered heteroaromatic ring. $Ar_3$ can be: a 5-membered heteroaromatic ring; a 6-membered aromatic ring; or a 6-membered heteroaromatic ring. $Ar_1$ and $Ar_2$ can each independently be substituted with: one or more H, alkyl, alkoxy, or aryl, which can be further substituted with sulfonium, selenonium, iodonium, other acid- or radical-generating species, or a monomer or pre-polymer functionality. $Ar_3$ can be substituted with: one or more H, acceptor, alkyl, alkoxy, aryl, which can be further substituted with sulfonium, selenonium, iodonium, other acid- or radical-generating species, or a monomer or pre-polymer functionality. $R_1$ and $R_2$ can be independently: H, alkyl, or aryl, which can be further substituted with sulfonium, selenonium, iodonium, other acid- or radical-generating species, or a monomer or pre-polymer functionality. At least one of $Ar_1$, $Ar_2$, $Ar_3$, $R_1$, or $R_2$ must be substituted with one or more sulfonium, selenonium, or iodonium groups, or other acid- or radical generating groups. Y is said counterion, and is one of the anions defined previously. The overall charge on the dye portion of the molecule is denoted by z. Integer p is the charge on the counterion, integers q and Q and are the number of anions and cations respectively in the empirical formula and are such that the quantity zQ=pq, where pq is a positive integer less than 9 (which range includes all values and subranges therein, including 1, 2, 3, 4, 5, 6, 7, and 8). The following are provided as illustrative examples, but are not limiting cases: z=1, Q=1, p=1, q 1, so pq=1; and z=2, Q=1, p=1, q=2, so pq=2.

In another preferred embodiment, the molecules should have the structure:

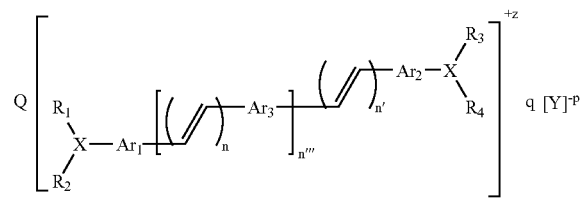

where X is N, n=0, 1, 2, 3, 4 or 5, n'=0, 1, 2, 3, 4, or 5 and n'''=0, 1, 2, 3, 4, or 5. $Ar_1$ and $Ar_2$ can each independently be: a 5-membered heteroaromatic ring; a 6-membered aromatic ring; or a 6-membered heteroaromatic ring. $Ar_3$ can be: a 5-membered heteroaromatic ring; a 6-membered aromatic ring; or a 6-membered heteroaromatic zing. $Ar_1$ and $Ar_2$ can each independently be substituted with: one or more H, alkyl, alkoxy, or aryl, which can be further substituted with sulfonium, selenonium, iodonium, other acid- or radical-generating species, or a monomer or pre-polymer functionality. $Ar_3$ can be substituted with: one or more H, acceptor, alkyl, alkoxy, or aryl, which can be further substituted with sulfonium, selenonium, iodonium, other acid- or radical-generating species, or a monomer or pre-polymer functionality. $R_1$, $R_2$, $R_3$, and $R_4$ can be independently: H, alkyl, or aryl, which can be further substituted with sulfonium, selenonium, iodonium, other acid- or radical-generating species, or a monomer or pre-polymer functionality. At least one of $Ar_1$, $Ar_2$, $Ar_3$, $R_1$, $R_2$, $R_3$, or $R_4$ must be substituted with one or more sulfoniumn, selenonium, or iodonium groups, or other acid- or radical generating groups. Y is said counterion, and is one of the anions defined previously. The overall charge on the dye portion of the molecule is denoted by z. Integer p is the charge on the counterion, integers q and Q are the number of anions and cations respectively in the empirical formula and are such that the quantity zQ=pq, where pq is a positive integer less than 9 (which range includes all values and subranges therein, including 1, 2, 3, 4, 5, 6, 7, and 8). The following are provided as illustrative examples, but are not limiting cases: z=1, Q=1, p=1, q=1, so pq=1; and z=2, Q=1, p=1, q=2, so pq=2.

In another preferred embodiment, the molecules should have the structure:

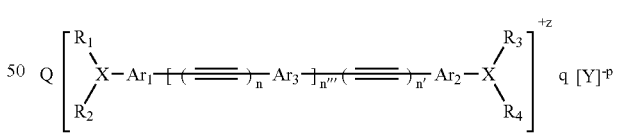

where X is N, n=0, 1, 2, 3, 4, or 5, n'=0, 1, 2, 3, 4 or 5 and n'''=0, 1, 2, 3, 4, or 5. $Ar_1$ and $Ar_2$ can each independently be: a 5-membered heteroaromatic ring; a 6-membered aromatic ring; or a 6-membered heteroaromatic ring. $Ar_3$ can be: a 5-membered heteroaromatic ring; a 6-membered aromatic ring; or a 6-membered heteroaromatic ring. $Ar_1$ and $Ar_2$ can each independently be substituted with: one or more H, alkyl, alkoxy, or aryl, which can be further substituted with sulfonium, selenonium, iodonium, other acid- or radical-generating species, or a monomer or pre-polymer functionality. $Ar_3$ can be substituted with: one or more H, acceptor, alkyl, alkoxy, or aryl, which can be further substituted with sulfonium, selenonium, iodonium, other acid- or radical-generating species, or a monomer or pre-polymer functionality. $R_1$, $R_2$, $R_3$, and $R_4$ can be independently: H, alkyl, or aryl, which can be further substituted with sulfonium, selenonium, iodonium, other acid- or radical-generating species, or a monomer or pre-polymer functionality. At least one of $Ar_1$, $Ar_2$, $Ar_3$, $R_1$, $R_2$, $R_3$, or $R_4$ must be substituted with one or more sulfonium, selenonium, or iodonium gropus, or other acid- or radical generating groups. Y is said counterion, and is one of the anions defined previously. The overall charge on the dye portion of the molecule is denoted by z. Integer p is the charge on the counterion, integers q and Q and are the number of anions and cations respectively in the empirical formula and are such that the quantity zQ=pq, where pq is a positive integer less than 9 (which range includes all values and subranges therein, including 1, 2, 3, 4, 5, 6, 7, and 8). The following are provided as illustrative examples, but are not limiting cases: z=1, Q=1, p=1, q=1, so pq=1; and z=2, Q=1, p=2, so pq=2.

In another preferred embodiment, the composition should contain one or more sensitizers selected from the group of molecules including:

Class 1 Structures: Compounds where the end groups are electron donating groups

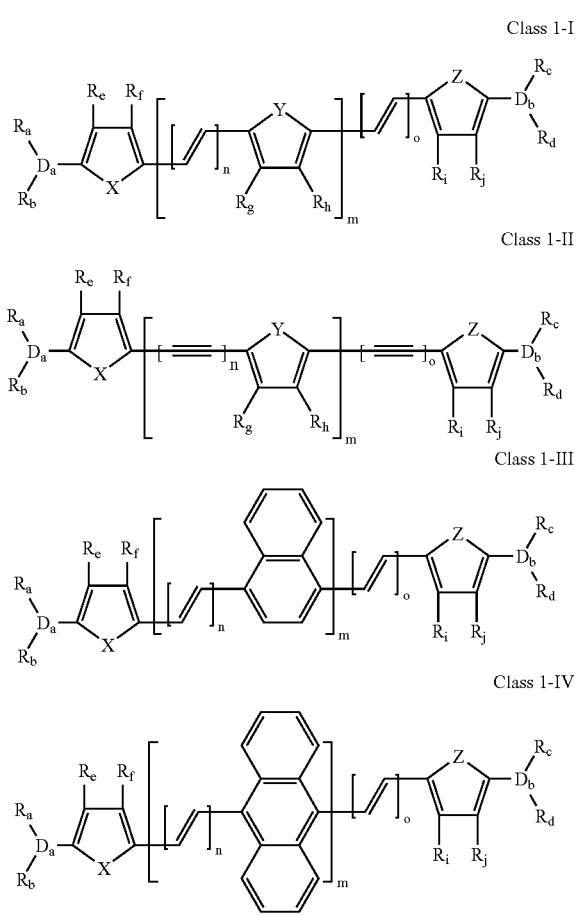

Class 1-I

Class 1-II

Class 1-III

Class 1-IV where $D_a$ is an electron donating group that is any one of N, O, or S, where m, n, o are integers such that $0 \leq m \leq 10$, $0 \leq n \leq 10$, $0 \leq o \leq 10$ (which ranges independently include all values and subranges therebetween, including 1, 2, 3, 4, 5, 6, 7, 8, and 9); and where X, Y, Z are independently selected from the group including: $CR_k=CR_l$; O; S; N—$R_m$ where $R_e$, $R_f$, $R_g$, $R_h$, $R_i$, $R_j$, $R_k$, $R_l$, $R_m$ are defined in NOTE 1.

$R_a$, $R_b$, $R_c$, $R_d$ wherein $R_a$, $R_b$, $R_c$, $R_d$ are independently selected from the group including: H; a linear or branched alkyl group with up to 25 carbons; —$(CH_2CH_2O)_\alpha$—$(CH_2)_\beta OR_{a1}$; —$(CH_2CH_2O)_\alpha$—$(CH_2)_\beta NR_{a2}R_{a3}$; —$(CH_2CH_2O)_\alpha$—$(CH_2)_\beta CONR_{a2}R_{a3}$; —$(CH_2CH_2O)_\alpha$—$(CH_2)_\beta CN$; —$(CH_2CH_2O)_\alpha$—$(CH_2)_\beta Cl$; —$(CH_2CH_2O)_\alpha$—$(CH_2)_\beta Br$; —$(CH_2CH_2O)_\alpha$—$(CH_2)_\beta I$; —$(CH_2CH_2O)_\alpha$—$(CH_2)_\beta$-Phenyl; various aryl groups; various fused aromatic rings;

where $\alpha$ is 0-10, where $\beta$ is 1-25, (wherein each of the above ranges independently includes all values and subranges therebetween, including 1, 2, 3, 4, 5, 6, 7, 8, 9, 10, 11, 12, 13, 14, 15, 16, 17, 18, 19, 20, 21, 22, 23 and 24 as appropriate).

In the case of Da (Db)=O or S, Rb (Rd)=nothing.

$R_e$, $R_f$, $R_g$, $R_h$, $R_i$, $R_j$, $R_k$, $R_l$, $R_m$

NOTE 1:

$R_e$, $R_f$, $R_g$, $R_h$, $R_i$, $R_j$, $R_k$, $R_l$, $R_m$ are independently selected from the group including H; a linear or branched alkyl group with up to 25 carbons;

—$(CH_2CH_2O)_\alpha$—$(CH_2)_\beta OR_{b1}$; —$(CH_2CH_2O)_\alpha$—$(CH_2)_\beta NR_{b2}R_{b3}$;

—$(CH_2CH_2O)_\alpha$—$(CH_2)_\beta CONR_{b2}R_{b3}$; —$(CH_2CH_2O)_\alpha$—$(CH_2)_\beta CN$;

—$(CH_2CH_2O)_\alpha$—$(CH_2)_\beta Cl$; —$(CH_2CH_2O)_\alpha$—$(CH_2)_\beta Br$; —$(CH_2CH_2O)_\alpha$—$(CH_2)_\beta I$;

—$(CH_2CH_2O)_\alpha$—$(CH_2)_\beta$-Phenyl; various aryl; various fused aromatic rings; $NR_{e1}R_{e2}$;

$OR_{e3}$; CHO; CN; $NO_2$; Br; Cl; I; phenyl;

where $\alpha$ is 0-10, where $\beta$ is 1-25, (wherein each of the above ranges independently includes all values and subranges therebetween, including 1, 2, 3, 4, 5, 6, 7, 8, 9, 10, 11, 12, 13, 14, 15, 16, 17, 18, 19, 20, 21, 22, 23 and 24 as appropriate).

The composition may optionally and preferably contain a second component that can be selected from the group including a sulfonium salt such described in U.S. Pat. Nos. 5,302,757, 5,274,148, 5,446,172, 5,012,001, 4,882,201, 5,591,011, or 2,807,648, or an iodonium salt selected from the group including those described in C. Herzig and S. Scheiding, DE 4,142,327, CA 119,250,162 and C. Herzig, EP 4,219,376, CA 120,298,975 and U.S. Pat. Nos. 5,079,378, 4992,571, 4,450,360, 4,399,071, 4,310,469, 4,151,175, 3,981,897, 5,144,051, 3,729,313, 3,741,769, 3,808,006, 4,250,053 and 4,394,403. Combinations are possible.

It is preferred that the anion for these salts be a nonnucleophilic anion such as $BF_4^-$, $PF_6^-$, $SbF_6^-$, $AsF_6^-$, or $SbCl_4^-$.

The two components of the photoinitiator system are preferably present in photochemically effective amounts, that is, amounts of each component sufficient to enable the resin to undergo photochemical hardening upon exposure to light of the desired wavelength. Preferably, for every 100 parts of monomer, the resin of the invention contains about 0.005 to about 10 parts (more preferably about 0.1 to about 4 parts) each of iodonium salt, sensitizer and donor. The amounts of each component are independently variable and thus need not be equal, with larger amounts generally providing faster cure, but shorter shelf life. These ranges include all values and subranges therebetween, including 0.007, 0.01, 0.05, 0.07, 0.5, 0.7, 0.9, 1, 1.1, 2, 3, 4, 5, 6, 7, 8, 9, and 9.5 parts per 100 parts.

The combination of amine-containing compounds acting as efficient sensitizers for iodonium salts has been reported for one photon excitation. U.S. Pat. Nos. 4,162,162, 4,268, 667, and 4,351,893 and EP 127,762 disclose sensitizers containing constrained amino-ketone groups for bi-imidazole initiators in addition polymerization. U.S. Pat. No. 4,505,793 discloses constrained coumarin sensitizers for triazine initiators. Amino group-containing-coumarins and constrained coumarins are also disclosed in U.S. Pat. Nos. 4,278,751, 4,147,552, and 4,366,228 and U.K. Patent 2,083,832 for use as triplet sensitizers for cyclo-addition reactions or for use as sensitizers for radical polymerization in combination with arylaminoacetic acids. References to these compounds are also found in Polym. Eng. Sci. 1983, 23, 1022-1024. This article mentions the utility of arninoketocoumarin compounds as sensitizers with alkoxypyridinium salts. Photoreactions of coumarin compounds are also mentioned in J. Org. Chem. 1984, 49, 2705-2708. U.S. Pat. No. 4,250,053 teaches constrained coumarin as a sensitizer of iodonium salt for cationic polymerization. We teach that the above combination of two-photon sensitizers shown in Classes 1-I to 1-IV above and iodonium or sulfoniums are excitable by two-photon and multi-photon excitation and should therefore have advantageous properties not available for the simple amino-ketone dye, coumarines and related compounds described previously.

Furthermore, U.S. Pat. No. 4,921,827, which is incorporated herein by reference, teaches that constrained alkylamino (particularly julolidino) ketone sensitizers increase the rate of polymerization when used in combination with iodonium salts. Thus we teach that two-photon dyes in which $R_a$, $R_b$, $R_c$, $R_d$ as described for Class 1-I, Class 1-II, Class 1-III, and Class 1-IV above are preferably part of a constrained julolidine ring. The large electron affinity of the iodonium groups, together with the electron-rich nature of the two-photon chromophores described in Class 1-I, Class 1-II, Class 1-III, and Class 1-IV above, strongly favors formation of a charge-transfer complex between the two-photon chromophores and the iodonium cation, which advantageously keep the species in close proximity, and which increases the efficiency of the two-photon and multi-photon induced sensitization process.

The invention, as defined in part by FIG. 1, includes compositions in which the multi-photon excitable molecular fragment may be a species other than those detailed above. Preferred examples of alternative multi-photon-excitable molecular fragments include, but are not limited to the following species: Disperse Red 1 (Delysse, S.; Raimond, P.; Nunzi, J.-M., Chem. Phys. 1997, 219, 341); Coumarin 120, Rhodamine B (Fischer, A.; Cremer, C.; Stelzer, E. H. K., Appl. Opt. 1995, 34, 1989); AF-50 (Mukheijee, N.; Mukheree, A.; Reinhardt, B. A., Appl. Phys. Lett. 1997, 70, 1524); AF-250 (Swiatkiewicz, J.; Prasad, P. N.; Reinhardt, B. A. Opt. Comm. 1998, 157, 135); and 4,4'-dicarbazolyl-stilbene (Segal, J.; Kotler, Z.; Ben-Asuly, S. M. A.; Khodorkovsky, V. Proc. Soc. Photo-Opt. Instrum. Eng. 1999, 3796, 153).

The invention, as defined in part by FIG. 1, includes compositions in which the photoacid generator fragment may be a species other than those detailed above. Preferable examples of alternative photoacid generator fragments include, but are not limited to the following species: 4-nitrobenzylsulfonates and perfluorobenzylsulfonates (Shirai, M.; Tsunooka, M. Prog. Polym. Sci. 1996, 21, 1); dialkylphenacylsulfonium salts and 3,5-dialkyl-4-hydroxyphenyl sulfonium salts (Crivello, J. V.; Lee, J. L. Macromol. 1981, 14, 1141).

The invention as described is not intended to be specific to any particularly mechanism of coupling between the two-photonabsorbing chromophore and the photoacid generating fragment. Preferred examples of possible coupling mechanisms include electron-transfer, exciplex formation, and energy transfer. One or more mechanisms can occur in the acid-generating photochemistry of a given molecule of the invention, and which mechanisms occur will depend upon the nature of the two-photon-absorbing chromophore and of the photoacid generating fragment. By analogy, such mechanisms of coupling can be used to generate radical species as well, as should be evident to one skilled in the art.

The compositions of the invention are photoacid generator molecules that can be efficiently activated by multi-photon excitation. The compositions themselves may exist as crystals, mesoscopic phases, polymers, glasses, liquids or gases. The compositions may be used alone or in combination with other crystals, mesoscopic phases, polymers, glasses, liquids, or gases.

A particularly convenient and effective form of an optical element in accordance with the invention involves dispersing the multi-photon absorbing photoacids in a polymeric or prepolymeric binder. The multi-photon absorbing photoacids can be mixed into the binder, or incorporated by grafting the chromophore onto the polymer, prepolymer or monomer constituents. Preferable binders include, for example, polystyrene, polyacrylonitrile, polymethacrylate, poly(methyl methacrylate), poly(vinyl alcohol), copolymers of methyl methacrylate and methacrylic acid, copolymers of styrene and maleic anhydride and half ester-acids of the latter, as well as many others. Combinations are possible.

It is preferred that the polymeric binder be highly transparent so that the transparency of the molecules utilized in the practice of this invention can be advantageously employed. However, it is a unique feature of the invention that even in the case where the binder has strong absorption at the wavelength required to initiate single-photon processes, the chromophores may still be excited by the two-photon or multi-photon absorption process.

Generally, the methods according to invention are carried out by converting a multi-photon absorbing molecule to an electronically excited state by absorption of at least two photons of radiation. The generation of acid following excitation then facilitates numerous applications. The molecule may be irradiated with visible, ultraviolet or infrared radiation. Preferably, the molecule is irradiated at wavelengths from 300 to 1100 nm, which range includes all values and subranges therebetween, including 400, 500, 600, 700, 800, 900, and 1000 nm.

By changing the length and nature of the π-bridge and the strength and nature of the donor and/or acceptor groups, it is possible to control several important molecular photophysical characteristics. These include, for example, the position and strength of the two-photon (or higher-order) absorption band(s), the energies of the lowest-occupied and highest unoccupied molecular orbitals, the excited-state lifetimes, and the fluorescence efficiency. The composition of the π-conjugated bridge and the donor/acceptor groups can also be modified in such a way that the ease with which the material dissolves into a variety of host media—including liquids and polymeric hosts—is advantageously varied.

Compositions of the type described above may, in principle, be used for the photo-activated transformation of any acid-modifiable host medium. Examples of acid-modifiable materials include, but are not limited to: cationically polymerizable and cross-linkable media, catalyzed step-growth polymerizable and cross-linkable media, acid-cleavable ester-functionalized chemically amplified resins (as discussed in U.S. Pat. No. 6,136,500, herein incorporated by reference), polymerizable or cross-linkable materials containing acid-activated polymerization catalysts, and acid-sensitive biological media such as polypeptides and proteins. Preferred materials of these types are discussed in U.S. Pat. No. 5,514,728, which is incorporated herein by reference.

One especially preferable class of such materials includes monomers, oligomers, and or cross-linkable materials containing a cationically polymerizable group, such as epoxides, cyclic ethers, vinyl ethers, vinylamines, lactones, and cyclic acetals. Materials of this type are discussed in U.S. Pat. No. 5,514,728, incorporated herein by reference. Combinations are possible.

The molecules of this invention can be used for multi-photon-excitation initiated ring-opening methathesis polymerization ROMP). It is known that certain ROMP catalysts will initiate living ROMP of small-ring cyclic alkenes upon the introduction of acid (Lynn, D. M.; Mohr, B.; Grubbs, R. H.; Henling, L. M.; Day, M. W. J. Am. Chem. Soc. 2000, 122, 6601). Multi-photon activatable ROMP can then be achieved by irradiating a mixture containing a ROMP medium to which has been added the molecules of this invention.

Onium salts are also well known to generate radicals which can activate free radical polymerization and cross-linking. As such, the molecules of the invention can also be used for the photopolymerization and photo-crosslinking of free-radical-polymerizable compounds. Compounds of this type contain at least one ethylenically unsaturated double bond. Some preferred examples include monomers, oligomers, and cross-linkable polymers containing acrylate, methacrylate, acrylamide, methacrylamide, and vinyl functionalities. Free-radical-polymerizable compounds are described in U.S. Pat. No. 5,514,728, incorporated herein by reference. In cases where the solubility of the resin in a selected solvent decreases upon exposure to radiation, the resins are termed negative resists. Preferable examples of negative resist that could be used in accord with this invention are described in U.S. Pat. Nos. 5,463,084, 5,639,413, 6,268,403, 4,689,289, 4,069,056, 4,102,687, 4,069,055, 4,069,056, 4,058,401, 4,058,400, 5,086,192, 4,791,045, 4,090,936, 5,102,772, and 5,047,568, and patents cited therein—which are incorporated herein by reference. Other resists can undergo chemical transformations where the solubility of the resin in a selected solvent increases; these resins are termed postive resists. Postive resists are well known to those skilled in the art of lithography and may be used in accord with this invention, and some preferred examples are described in U.S. Pat. Nos. 6,346,363 and 6,232,417 which are incorporated herein by reference. The compositions of the invention can generate both acid and radical species. The tendency of a certain molecule of the invention to generate radicals versus acid will depend upon the specific molecular structure and the medium in which the molecule is dispersed. Acid generation is favored in cases, among other known to those skilled in the art, for which the molecules selected from those of the invention bear groups which upon protonation have pKa's less than or equal to 2. Acid generation is disfavored in cases for which the molecules selected from those of the invention bear groups which upon protonation have pKa's greater than 2.

The compositions of matter described in this invention also provide a means for the direct fabrication of complex microstructures from ceramic materials. U.S. Pat. Nos. 6,117,612, 6,129,540, 5,962,108, 5,939,182, 5,814,355, and 5,628,952 and patents cited therein—which are incorporated herein by reference—disclose composite materials which include a photoinitiator, a polymerizable resin, and a ceramic additive present at a high fraction of weight-loading. Films of the composite can be pattern-irradiated by masking or stereolithography to form a patterned polymer matrix containing the ceramic additive. The polymerized material is then heated to remove the polymer binder and to sinter the ceramic precursor into a hardened ceramic part. The process disclosed in U.S. Pat. No. 6,117,612 only pertains to one-photon initiated polymerization and patterning achieved via multi-step masking or stereolithography. Given the inherent limitations of stereolithography, the process disclosed in U.S. Pat. No. 6,117,612 is only capable of producing macro-scale three-dimensional ceramic parts having feature sizes larger than 100 µm. By the present invention, two-photon- and multi-photon-processible ceramic/pre-polymer composites can be formulated, wherein the one-photon initiators of U.S. Pat. No. 6,117,612 are replaced by the highly efficient two-photon initiators of the present invention. Since the initiators of the present invention can generate both radicals and a Brønsted or Lewis acid upon irradiation, the prepolymer may be a free-radical-polymerizable species (acrylate, acrylamide, etc.), as described in U.S. Pat. No. 6,117,612, or cationically polymerizable media (epoxides, vinyl ethers, cycle ethers, etc.), the use of which is not described in U.S. Pat. No. 6,117,612. These new formulations can then be used for the direct two-photon (multiphoton) microfabrication of ceramic parts, wherein the desired three-dimensional pattern is generated using the two-photon (multiphoton) microfabrication technique and irradiation geometry described earlier.

The inclusion of moieties of known excited-state reactivity in chromophores with strong two-photon or multi-photon absorption allows the invention compounds to have a great variety of novel and useful applications including, but not limited to, those described below and above.

The invention two-photon or multi-photon initiators may be used for two-photon (multi-photon) generation of charge carriers, including protonic conductivity, for example in photorefractive polymers.

The invention two-photon or multi-photon initiators may be used for two-photon or multi-photon initiated polymerization.

The invention two-photon or multi-photon initiators may be used for photoinduced cleavage of activated ester functionalities (such as tert-butoxy, tetrahydropyranyl, etc.).

The invention two-photon or multi-photon initiators may be used to initate changes in a host medium to write holographic information.

The invention two-photon or multi-photon initiators may be used for two-photon or multi-photon optical lithography and three-dimensional optical memory.

The invention two-photon or multi-photon initiators may be used for microfabrication of three-dimensional objects.

The invention two-photon or multi-photon initiators may be used to alter the pH of an arbitrary medium.

The invention two-photon or multi-photon initiators may be used for in vivo or in vitro decaging of biochemical agents for biological, physiological, or medicinal purposes, including drug delivery and photodynamic therapy.

The invention two-photon or multi-photon initiators may be used for modifying and functionalizing an arbitrary surface, photoresist patterning and processing, surface inking, and patterning printing plates.

The invention two-photon or multi-photon initiators may be used for modifiing, functionalizing, or texturing the surface or sub-surface of a biological tissue, with the aim, for example, of culturing the growth of cells, or modifying and engineering tissues.

The invention two-photon or multi-photon initiators may be used to photoactivate reactions which destabilize liposome membranes, which in turn may be used for drug delivery, photodynamic therapy, and decaging of agents in diagnostic assays.

The invention two-photon or multi-photon initiators can be used for the fabrication or articles using single-beam tightly focused (numerical aperture of 0.2 to 1.4) laser exposure.

The invention two-photon or multi-photon initiators can be used for the fabrication of three-dimensional objects having 1, 2, and 3-dimensional periodicities using multiple-beam-holographic interference exposure.

The invention two-photon or multi-photon initiators can be used for the fabrication of articles having linear dimensions or feature sizes ranging from 10 centimeters to 20 nanometers, depending upon the specific optical excitation geometry employed.

A photo-patternable medium containing two or more of the two-photon or multi-photon initiators can be exposed sequentially or in parallel using different excitation wavelengths to impress two or more three-dimensional patterns into the same medium, and thereby produce a single complex three-dimensional object.

A series of one or more photo-patternable media containing one or more of the two-photon or multi-photon initiators can be used to photo-pattern a single complex three-dimensional object comprised of two or more distinct material systems.

A composite medium, consisting of (a) the compositions of the invention and (b) a self-assembling or self-organizing material (see below), can be photo-patterned by two- or multi-photon excitation to generate an article having structure, possibly on very different length-scales, defined by (1) the impressed photo-pattern and (2) the structure associated with the self-assembled units. Examples of self-assembling or self-organizing materials that may be used include, but are not limited to, the following: metal, semiconductor, and metal oxide nanoparticles; polymer, silica, and metal oxide microspheres; block co-polymers that spontaneously form ordered structures (e.g. lamellae or micro-domains); liquid crystals and liquid-crystal polymers in various phases; colloidal crystal arrays; lipid-bilayer systems ordered in various phases (e.g. vesicle, hexagonal, or columnar).

A more extensive listing of applications that would be rendered substantially more useful by virtue of the large two-photon or multi-photon absorptivities of the compounds described herein can be found for example in U.S. Pat. Nos. 4,228,861, 4,238,840, 4,471,470, 4,333,165, 4,466,080 and 5,034,613, which are incorporated herein by reference.

The multi-photon activatable materials described in this section can be used for the three-dimensional microfabrication of a wide range of complex devices and systems. Preferred examples include micro-electromechanical structures, micro-electrooptic systems, optical waveguides, photonic circuits, optical component couplers, micro-optical switching systems, microfluidic devices (such as disclosed in U.S. Pat. No. 6,136,212, which is incorporated herein by reference), and the construction of complex patterns and structures used as templates or microscaffolds in further fabrication processes.

Triarylamines are preferred as electron donors for two-photon chromophores for photoacids because i) triarylamine radical cations are known to be very stable, and thus the driving force and rate for bond homolysis should be improved greatly by the stability of the radical cation; ii) protonated triarylamino groups are extremely strong acids ($Ph_3N^+H$, $pK_a = -5$) and so the presence of this amine functionality should not inhibit reactions such as the ring-opening polymerization of epoxides; and iii) the conditions used in the preparation of aryl dialkyl sulfonium salts are compatible with the triarylamine functional group. Triarylamine sulfonium salts are thus particularly suitable.

The sulfonium group(s) can be attached to various sites on triphenylamines; for example, in the examples in Scheme 1 the sulfonium group is attached to the meta position of a phenyl ring on the donor nitrogen atom. The molecules described in Scheme 1 are highly efficient cationic photoinitiators with quantum yields of photoacid generation of ~0.5, independent of the counter-ion.

Scheme 1: Preparation of triphenylamine sulfonium salts

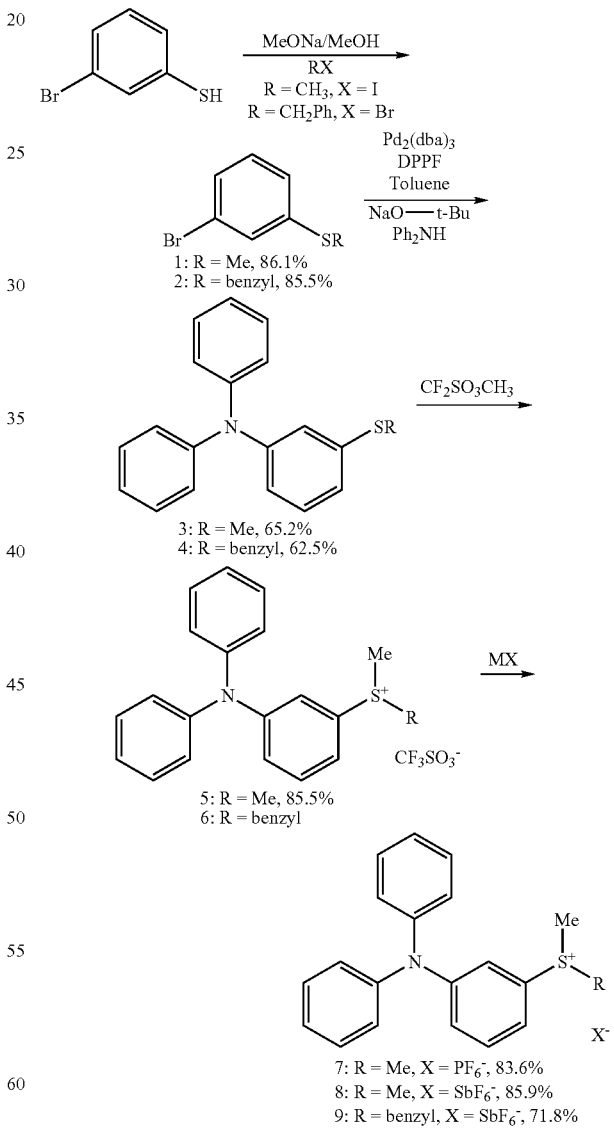

The sulfonium group can be attached to a two-photon dye by a covalent bond, as shown for the molecules in Scheme 2. The sulfonium group can be attached to various sites in the molecule, as will be described, but, in the examples shown in Scheme 2, the sulfonium group is attached to the meta position of a terminal phenyl group. Our experiments have shown that molecules described in this scheme are effective as initiators for the photopolymerization of a wide range of epoxides, including cyclohexene oxide, 4-vinyl-cyclohexene diepoxide, EPON SU-8, and ARALDITE CY179MA.
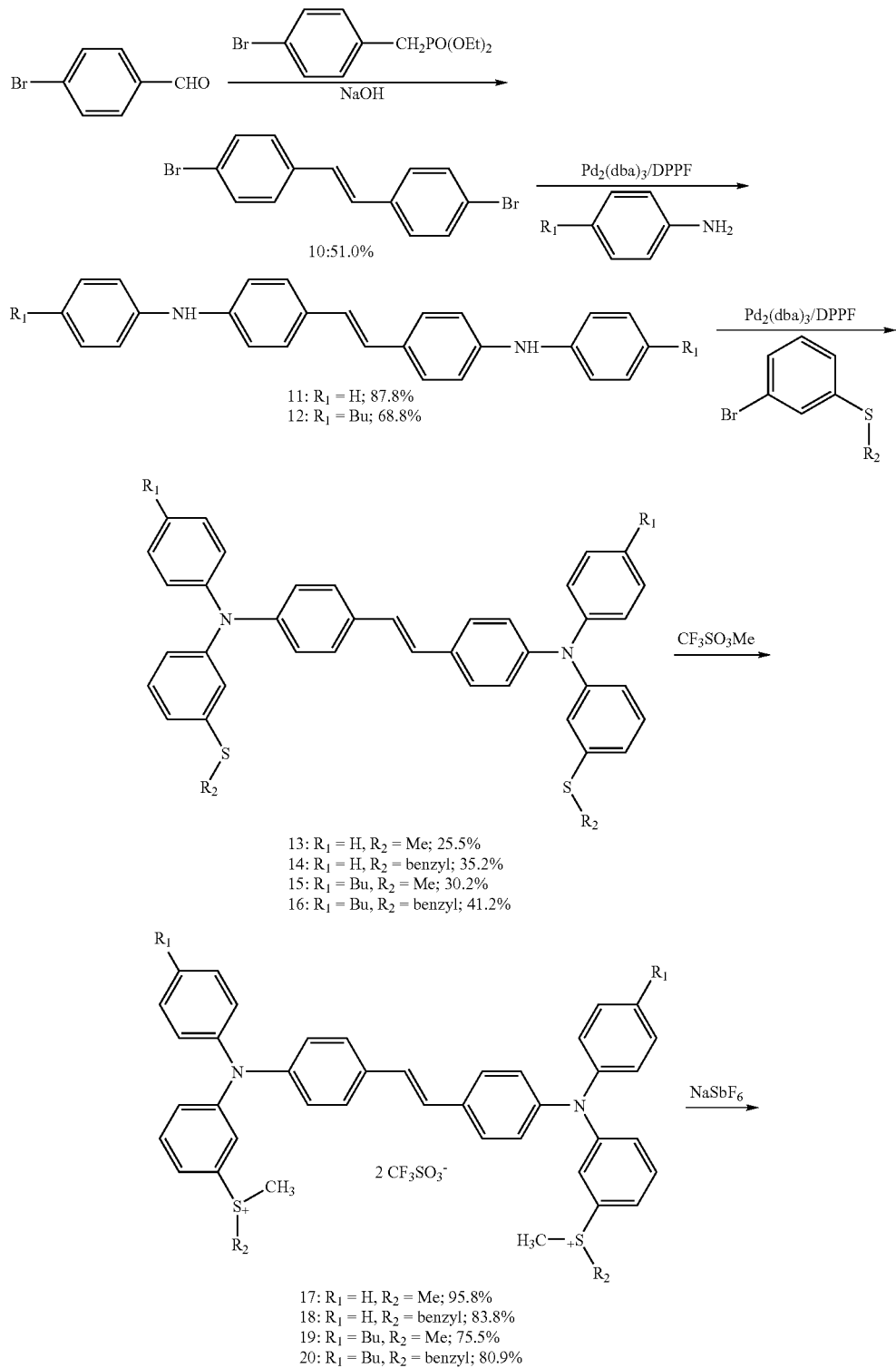

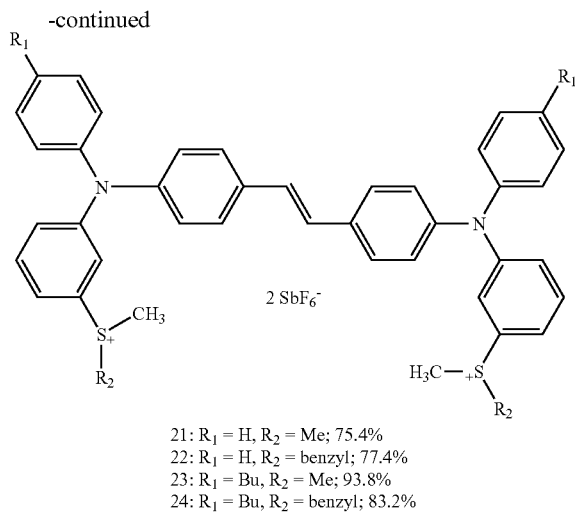

21: $R_1$ = H, $R_2$ = Me; 75.4%
22: $R_1$ = H, $R_2$ = benzyl; 77.4%
23: $R_1$ = Bu, $R_2$ = Me; 93.8%
24: $R_1$ = Bu, $R_2$ = benzyl; 83.2%

The precursor sulfides for bis(styryl)benzene sulfonium salts (type-I) 41 and 42 were synthesized using a phase-transfer Horner-Emmons reaction and Pd-catalyzed C—N coupling reactions (Scheme 3). However, the poor solubility of bis(arylarninostyryl)benzene in the Pd-catalyzed reaction mixture leads to the low yield of product, only 9.9% when R is methyl and 16.2% when R is benzyl, and total yields are 4.4% (R=methyl) and 7.2% (R=benzyl). Meanwhile, the formation of unknown side products makes purification difficult. Therefore, an improved route for the preparation such type of compounds was developed.

Scheme 3: Initial Preparation of bis(styryl) benzene dye type (I) precursors.

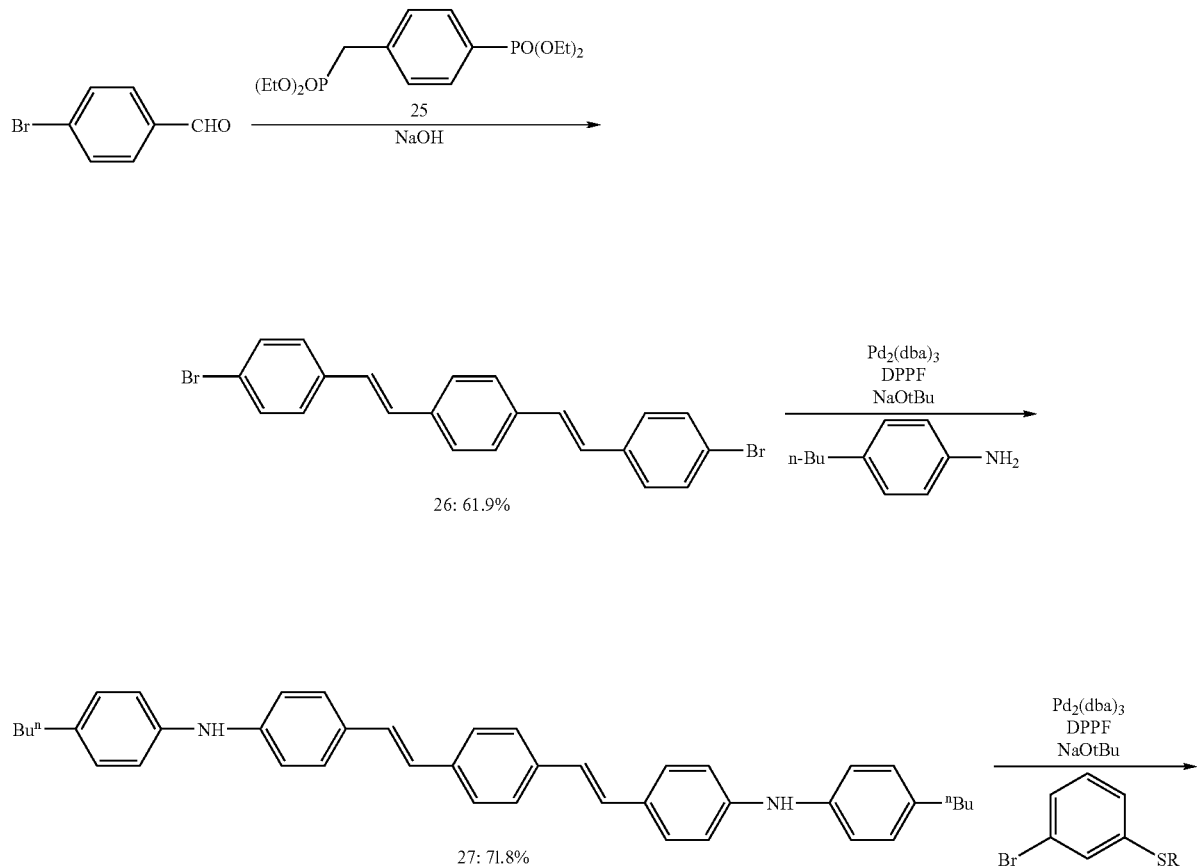

-continued

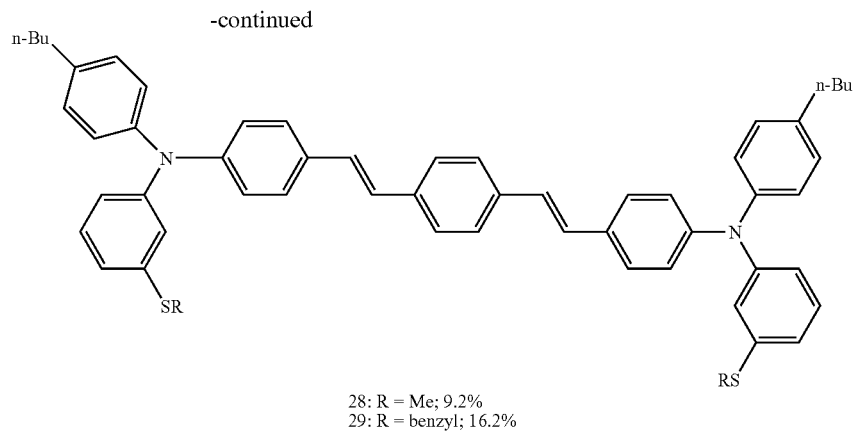

28: R = Me; 9.2%
29: R = benzyl; 16.2%

The yields in the alternative route, using Pd-catalyzed reactions followed by the Horner-Emmons reaction (Scheme 4), were quite high; 87.5% for methyl and 95.4% for benzyl. The low reactivity of 4-bromobenzaldehyde makes the Pd-catalyzed direct arylation of amines difficult; thus, a protected 4-bromobenzaldehyde derivative was used in the arylation. The arylation of the amine with the protected 4-bromobenzaldehyde afforded a high yield, and, without further separation, the deprotection was fast and complete in the presence of acid in TVE solution. The total yields for the preparation the precursor sulfides are 50.5% (R=methyl) and 49.7% (R=benzyl).

The syntheses of other types of bis(styryl)benzene sulfonium salts (type-II) 52 and 53 are shown in Scheme 5, wherein the sulfonium group is attached to an aryl ring closer to the dye center. The triarylamine can be made with palladium-catalyzed coupling chemistry, and then formylated under Vilsmeier conditions. The yields of the precursor sulfides by the Horner-Emmons coupling is high, and the final salts can be easily obtained.

Scheme 4: Improved preparation of bis(styryl) benzene dye sulfonium salts (I).

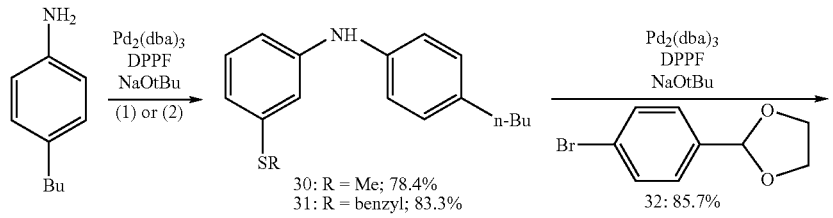

30: R = Me; 78.4%
31: R = benzyl; 83.3%

32: 85.7%

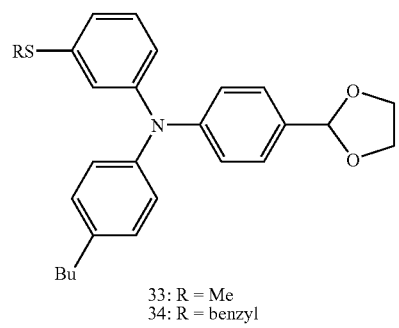

33: R = Me
34: R = benzyl

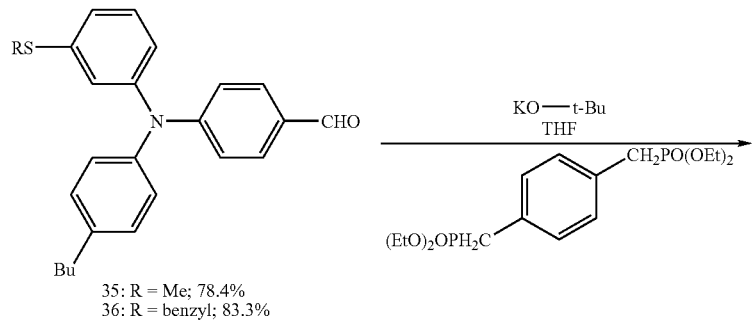
35: R = Me; 78.4%
36: R = benzyl; 83.3%
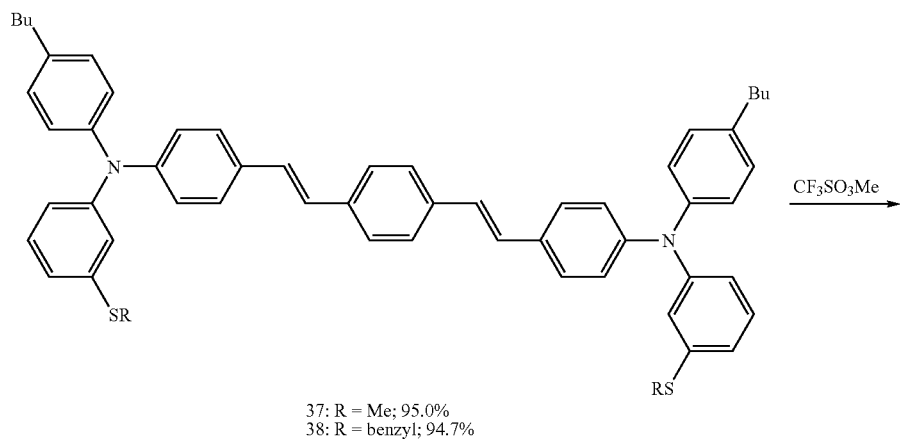
37: R = Me; 95.0%
38: R = benzyl; 94.7%
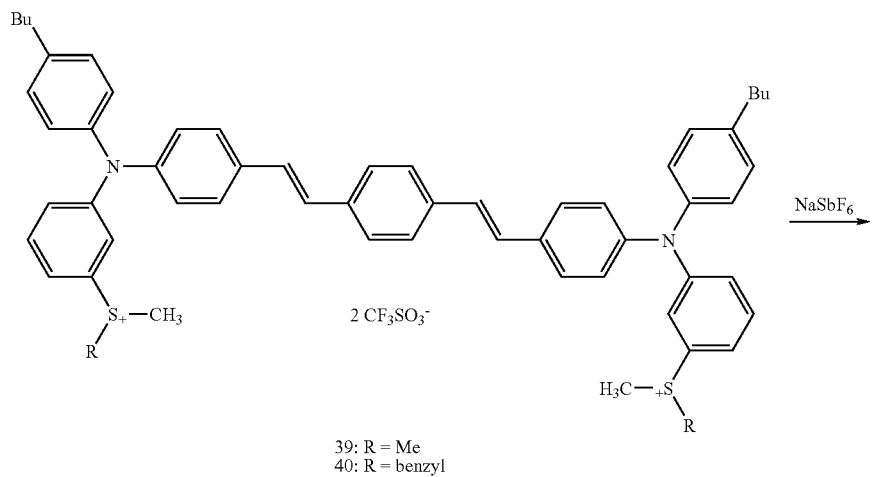
39: R = Me
40: R = benzyl -continued
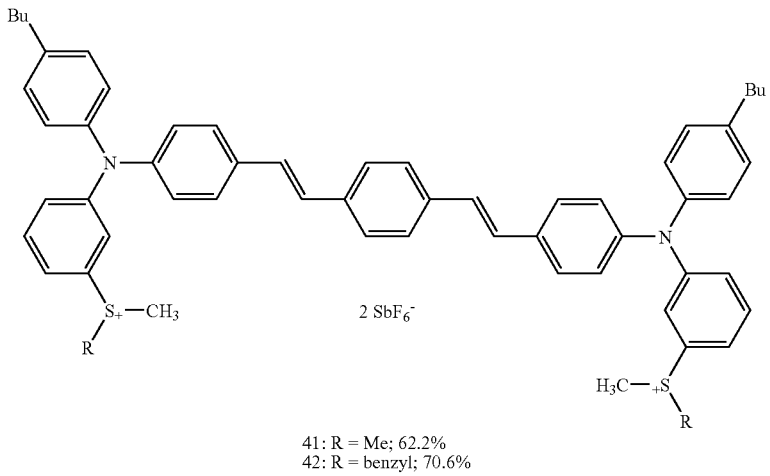
41: R = Me; 62.2%
42: R = benzyl; 70.6%
Scheme 5: Preparation of bis(styryl) benzene dye sulfonium salts (II).
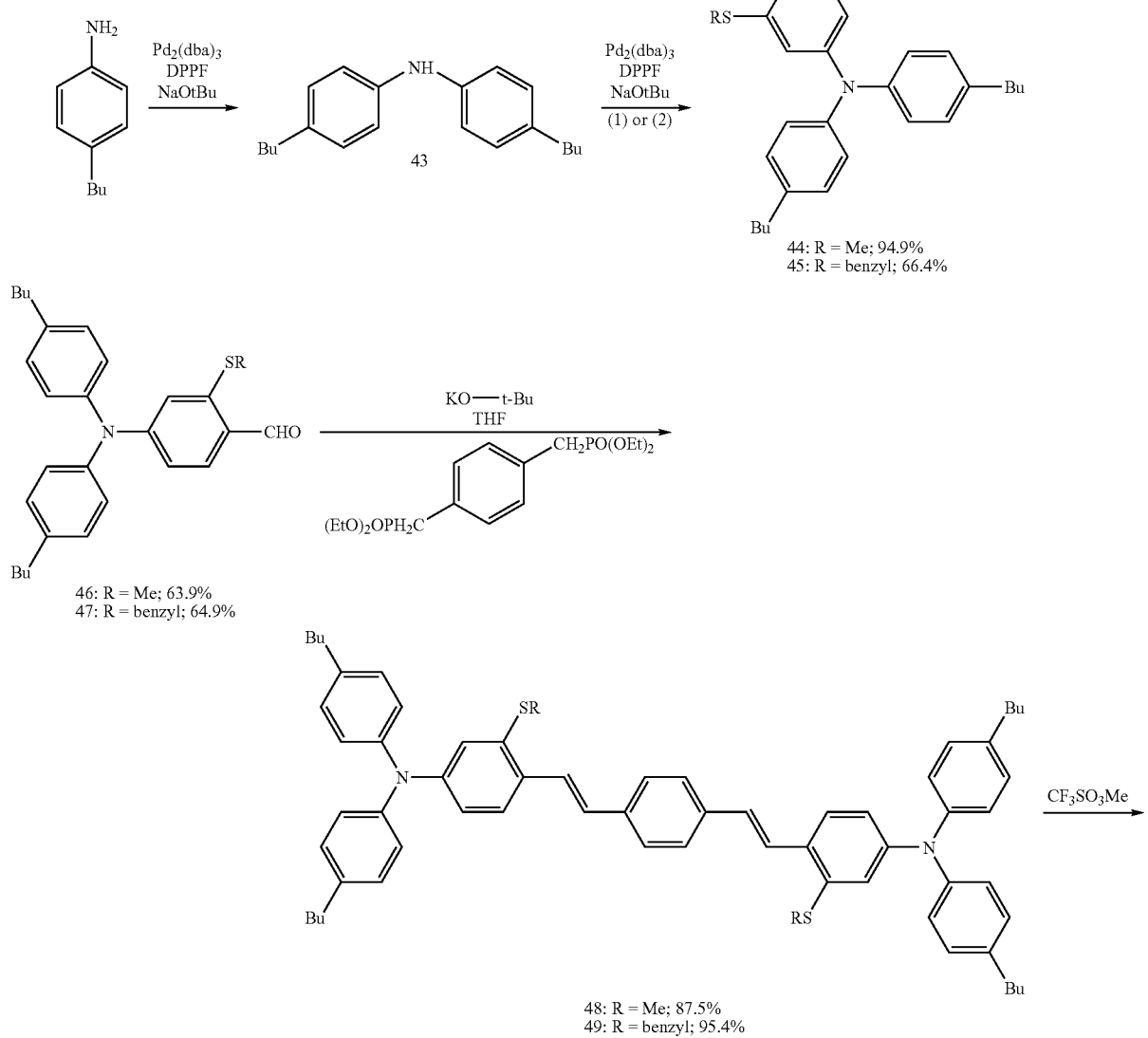
44: R = Me; 94.9%
45: R = benzyl; 66.4%
46: R = Me; 63.9%
47: R = benzyl; 64.9%
48: R = Me; 87.5%
49: R = benzyl; 95.4%

-continued

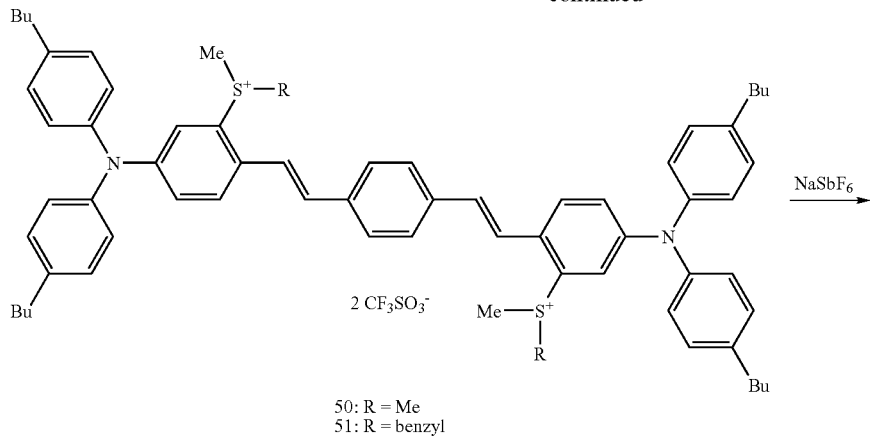

50: R = Me
51: R = benzyl

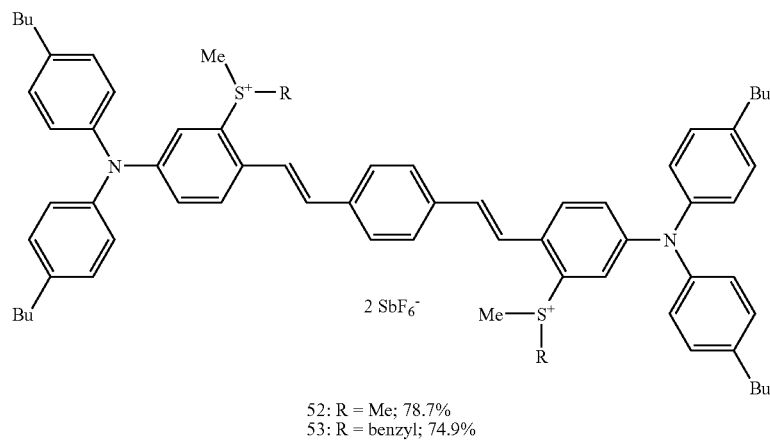

52: R = Me; 78.7%
53: R = benzyl; 74.9%

Two A-π-A bis(styryl)benzene sulfide precursors (59) (Scheme 6) and (64) (Scheme 7) with terminal electron-withdrawing sulfonium groups were synthesized. To increase solubility, long alkyl chains were introduced on the central phenyl ring (59) or linked to sulfur (64). 59 has been prepared by two different methods: the Wittig reaction and the Homer-Emmons reaction (Scheme 6).

Scheme 6: Preparation of A-π-A bis (styryl) benzene dye sulfonium salts (I)

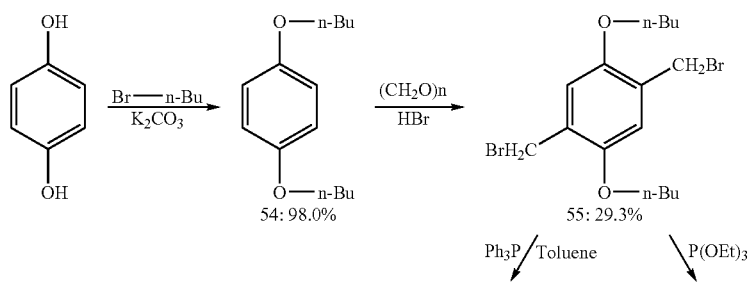

54: 98.0%
55: 29.3%

-continued
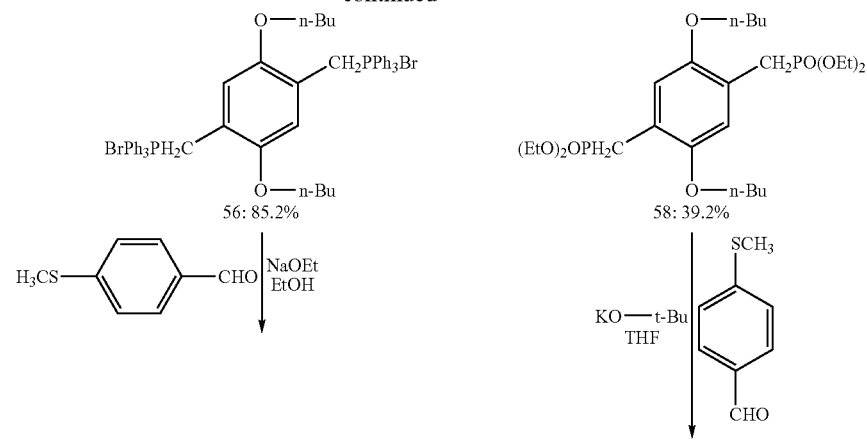
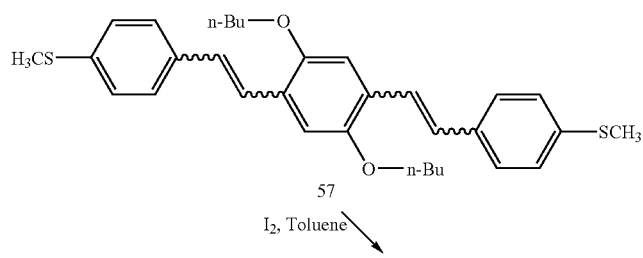
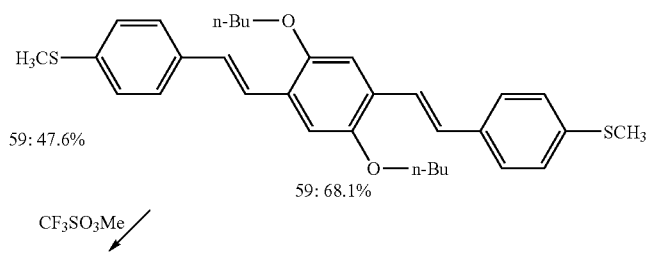
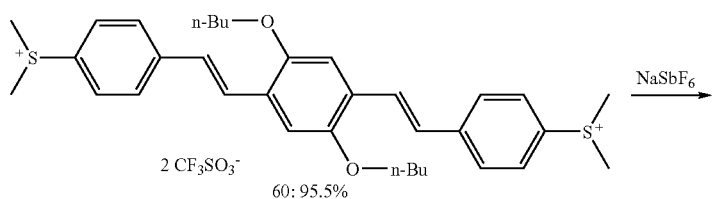
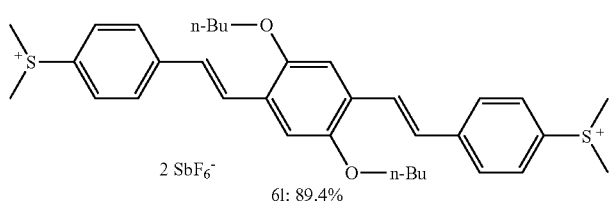

Scheme 7: Preparation of A-π-A bis(styryl)benzene sulfide precursor (II)

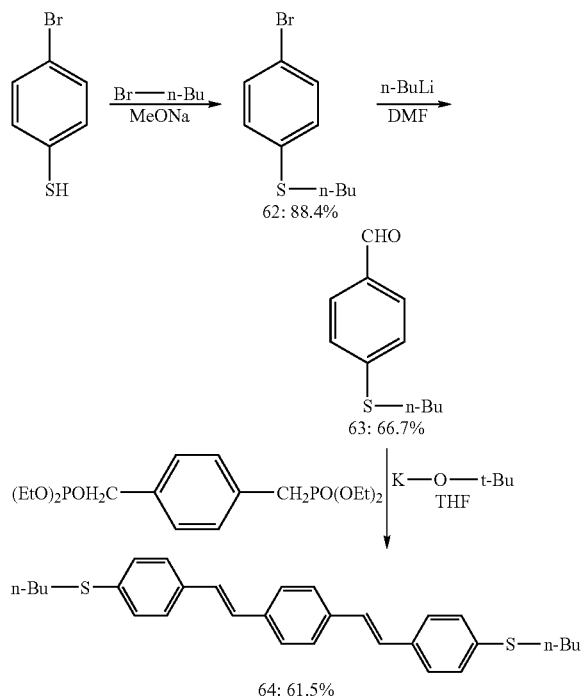

Since D-A-D type chromophores have large two-photon cross sections, and since the sulfonium group is a relatively strong electron acceptor, four D-A-D type bis(styryl)benzene molecules with sulfonium on the central ring and electron-donating alkoxy or amino donors on both ends were prepared. To increase the solubility of these species, long allyl chains were attached. Introduction of the alkoxy group as the donor shifts the molecules' absorption peaks to shorter wavelength, which could be advantageous for certain applications.

Three synthetic routes to precursor sulfides for such D-A-D type two-photon cationic initiators (mono or bis-sulfonium) were investigated (Scheme 8). Following route 1, attempts to synthesize 2-methylthio-α,α'-dibromo-p-xylene from 2-methylthio-p-xylene (64), or 2,5-di(methylthio)-α,α'-dibromo-p-xylene from 2,5-di(methylthio)-p-xylene (65) failed to yield the desired products using either N-bromosuccinimde (NBS) or paraformaldehyde/HBr/acetic as brominating agents. Following route 3, the preparation of 2-methylthio-p-benzenedialdehyde was found to be difficult to optimize. Route 2 was, therefore, employed, and the desired precursors (78, 79, 80 and 81) could be prepared as shown in Scheme 9. In an attempt to prepare 2,5-dibromo-α,α'-dibromo-p-xylene (67) or 2-bromo-α,α'-dibromo-p-xylene (68) using NBS, the bromine radical can attack both α-carbon and phenyl ring carbon positions. However, the reactivity of the α-carbon is still higher than that of the phenyl ring carbon and, therefore, in order to control the product distribution, NBS was added to the reaction mixture in several portions over a relatively long time period. The mono or bis products can be easily purified by recrystallization from methanol. In the preparation of sulfides from the corrresponding bromides using t-butyllithium followed by sulfur, the yields for butoxyl bis(styryl)benzenes (74, 75) are higher than those triphenylamine bis(styryl)benzene compound (76, 77).

Scheme 8: The possible routes for the preparation of D-A-D precursor sulfides

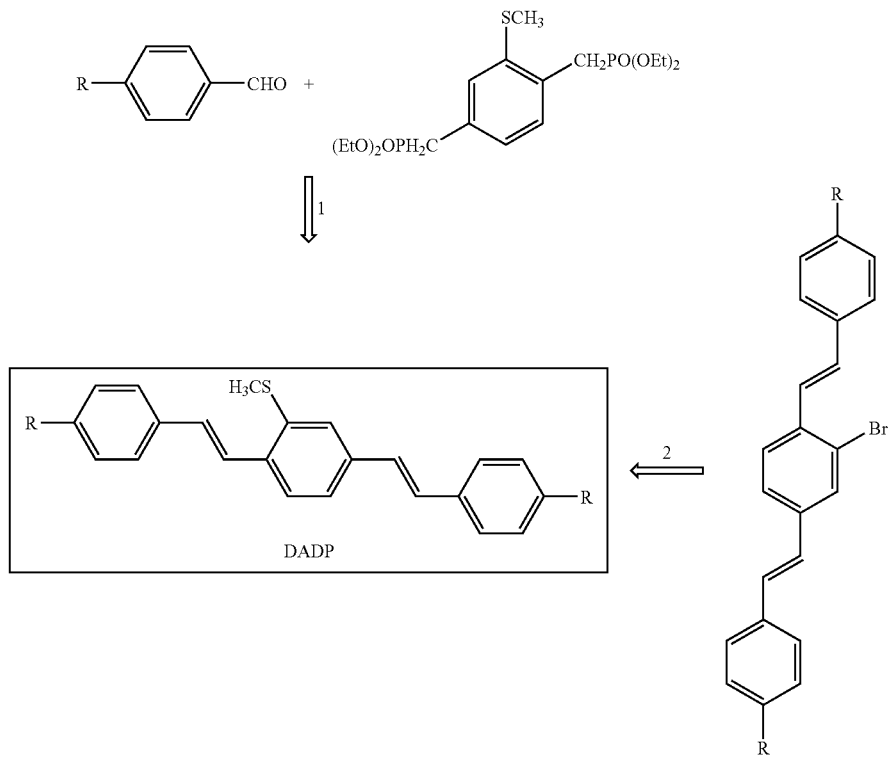

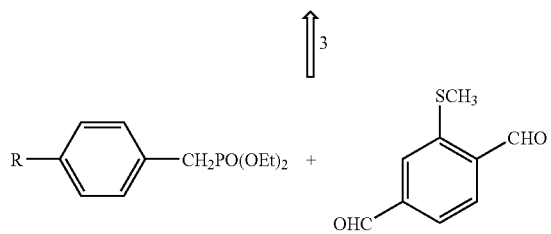
Scheme 9: Preparation of D-A-D sulfide precursors.
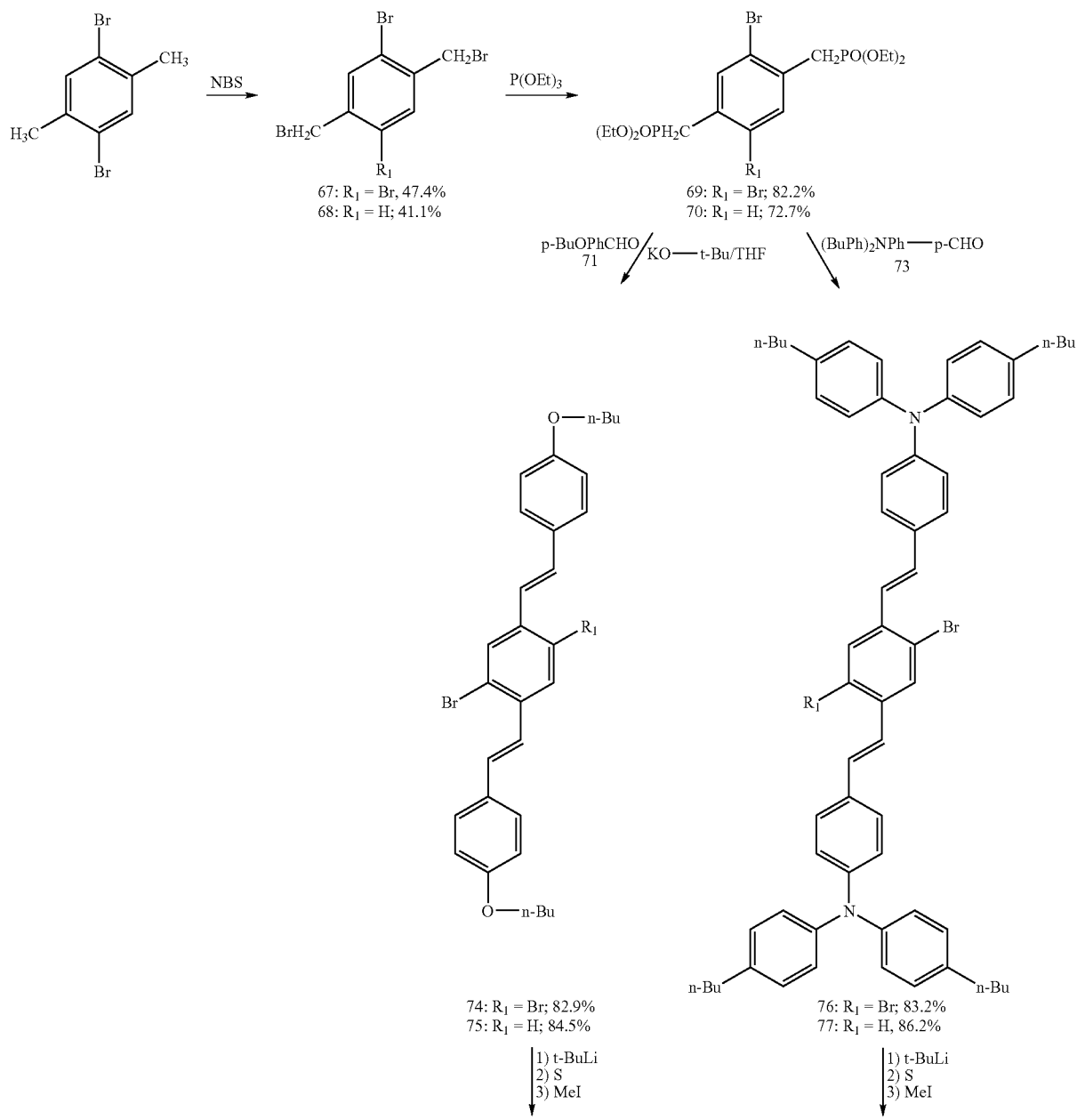

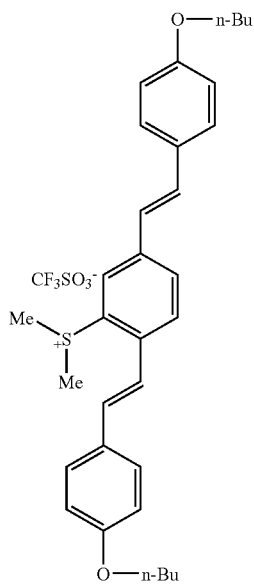
82: 85.0%
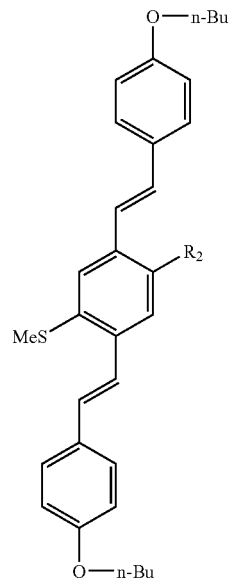
78: R₁ = Br; 48.7%
79: R₁ = H; 66.3%
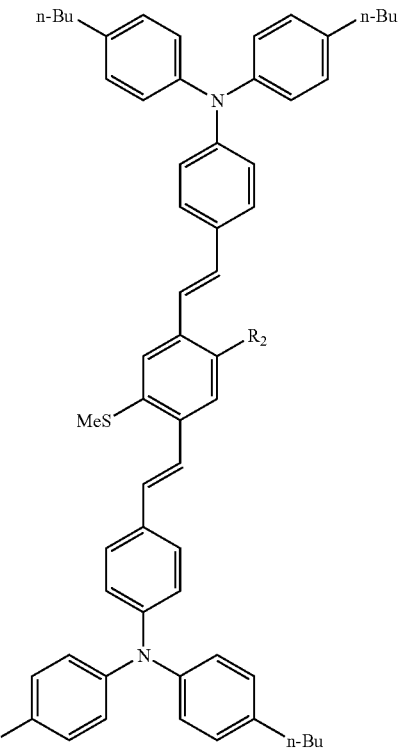
80: R₁ = Br
81: R₁ = H; 32.1%
Scheme 10: Preparation of phenothiazine sulfonium salts
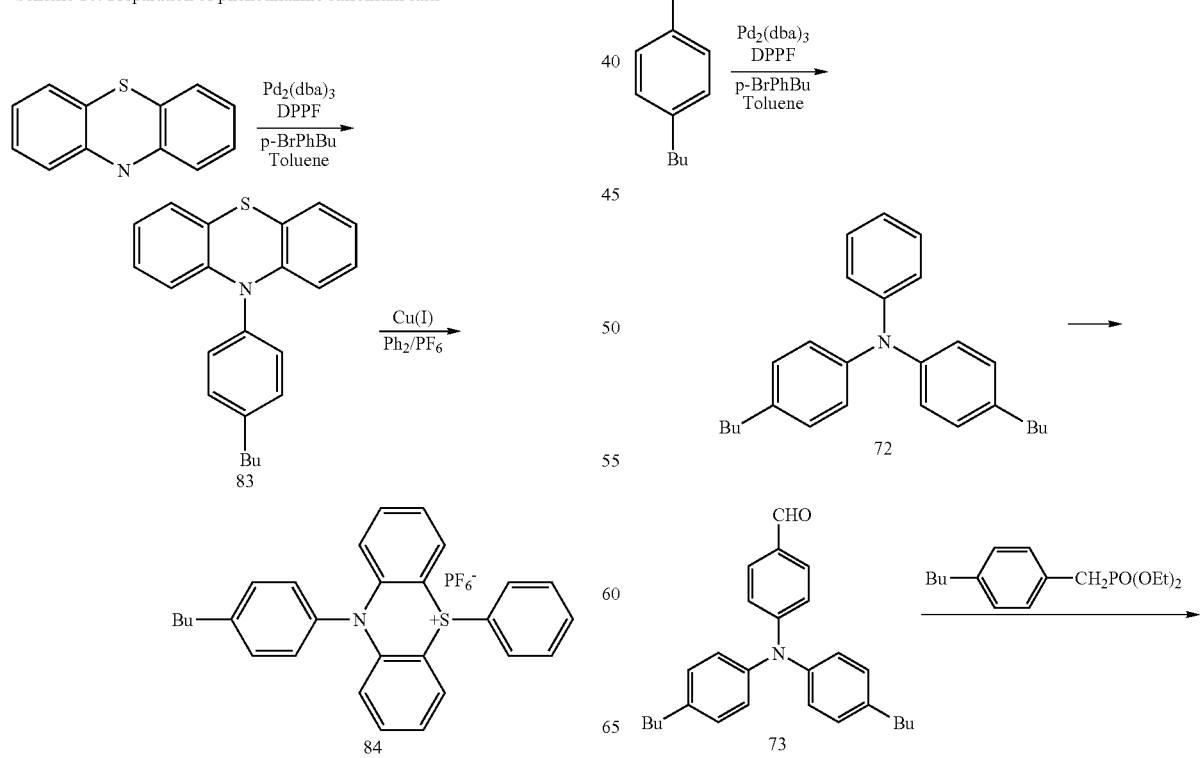

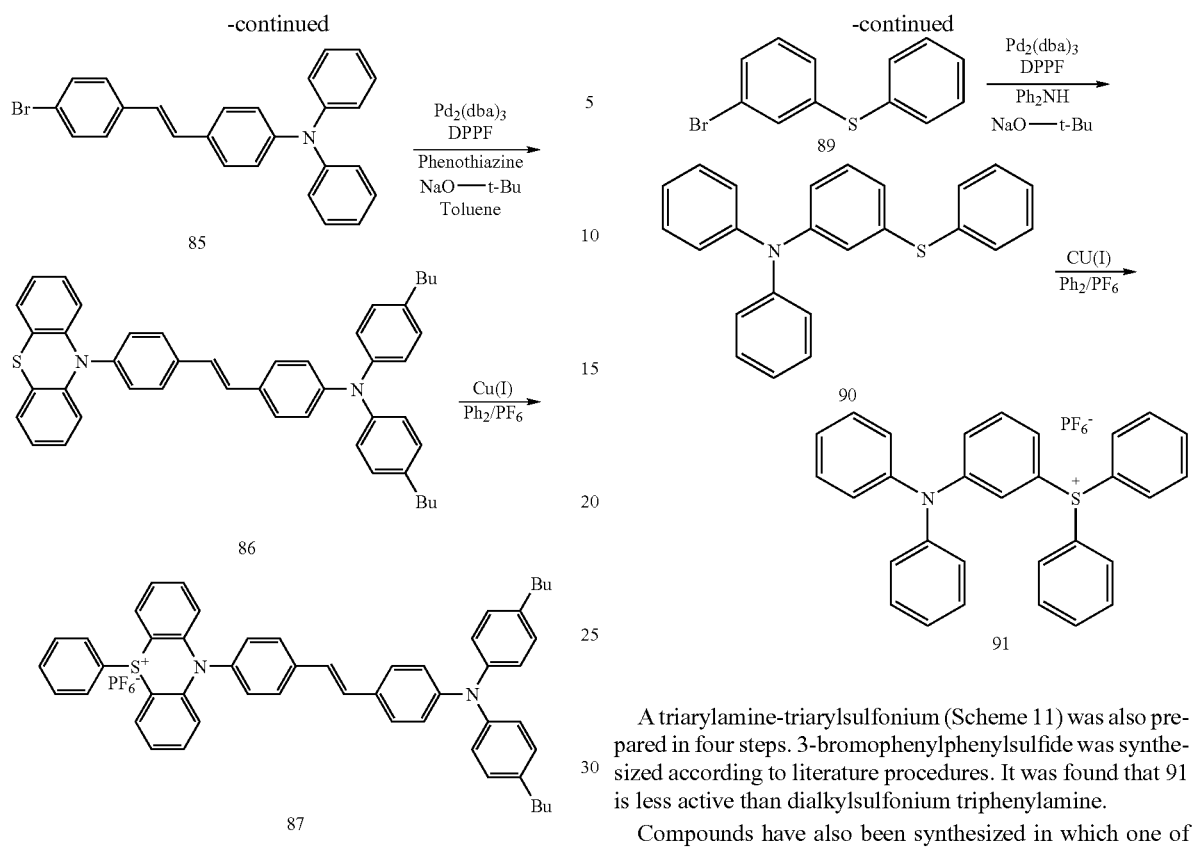

Triphenylsulfonium salts are known as UV sensitive cationic and radical initiators; like dialkyl sulfonium salts they can be attached to appropriate chromophore so that they act as photo-initiators via an electron transfer process. Phenothiazine, the first compound in Scheme 10, with N and S atoms in the central of three fused rings, is the basis of one method of attachment of a triphenylsulfonium group to a two-photon chromophore. The sulfur can be arylated to sulfonium and the secondary amino group affords a site for the extension of a conjugated system, such as those characteristics of D-π-D two-photon absorbing chromophores. As shown in Scheme 10, the molecules (84, 87) were prepared by first arylating the amine, using a palladium-catalyzed coupling reaction, and then arylating the sulfide using an iodonium salt. The acid-generation quantum yield for 87 (($\Phi_H^+$=0.21) is higher than that for 84 ($\Phi_H^+$=0.07). 87 can efficiently initiate both cationic and radical polymerization as shown in FIG. 5.

Scheme 11: Synthesis of a triarylamine-triarylsulfonium compound

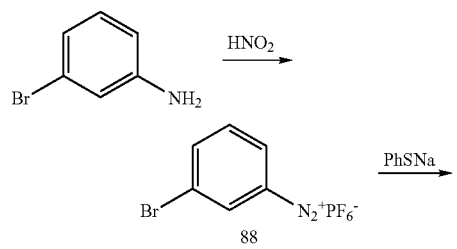

A triarylamine-triarylsulfonium (Scheme 11) was also prepared in four steps. 3-bromophenylphenylsulfide was synthesized according to literature procedures. It was found that 91 is less active than dialkylsulfonium triphenylamine.

Compounds have also been synthesized in which one of two electron donors is replaced by a nitrogen of the two-nitrogen-containing piperazine ring, and where the other secondary amine of the piperazine is linked to the active sulfonium group using a nucleophilic substitution reaction (e. g. 100, 106).

Stilbene dye-triphenylsulfonium compound 100 has been prepared in seven steps. Formylation of N,N-dibutylaniline gave 4-N,N-dibutylamino benzaldehyde (92) in a yield of 79.9%. Reduction of aldehyde 92 with NaBH$_4$ gave 4-N,N-dibutylamino benzylalcohol (93) in a yield of 89.4%. The preparation of 4-N,N-dibutylamino benzylchloride from alcohol 93 was unsuccessful using thionyl chloride (SOCl$_2$). However, chlorination of 93 was successful using concentrated hydrochloric acid, which gave a hydrochloride salt 94 in a yield of 96.1%. Since the neutral N,N-dibutylaminobenzylchloride is unstable and easily transformed to a carbocation (deep blue), the hydrochloride salt 94 was used in next step without further purification. The reaction of 94 with triethylphosphite gave phosphonate 95 in a yield of 90.1%. The BOC-protected piperazine-functionalized benzaldehyde, 97, was prepared in two steps. Nucleophilic displacement of fluoride from 4-fluorobenzaldehyde with piperazine gave 4-piperazinobenzaldehyde, 96, which reacted with BOC to give secondary amine-protected compound, 97. It was found that this nucleophilic substitution reaction is solvent-dependent; DMF gave none of the desired product, but DMSO was isolated in 48% over two steps. The reaction of 95 and 97 under Homer-Emmons conditions gave compound 98 in a yield of 74.2%; deprotection of 98 gave the mono-piperzino dye 99 in a yield of 89.7%. Finally, the nucleophilic substitution reaction of 99 with 4-fluorophenyldiphenylsulfonium hexafluorophosphate in DMSO gave the light-sensitive compound 100 in a yield of 73.6%.

Scheme 12: Preparation of a triphenlysulfonium salt linked through piperazine to a stilben-based two-photon chromophore.

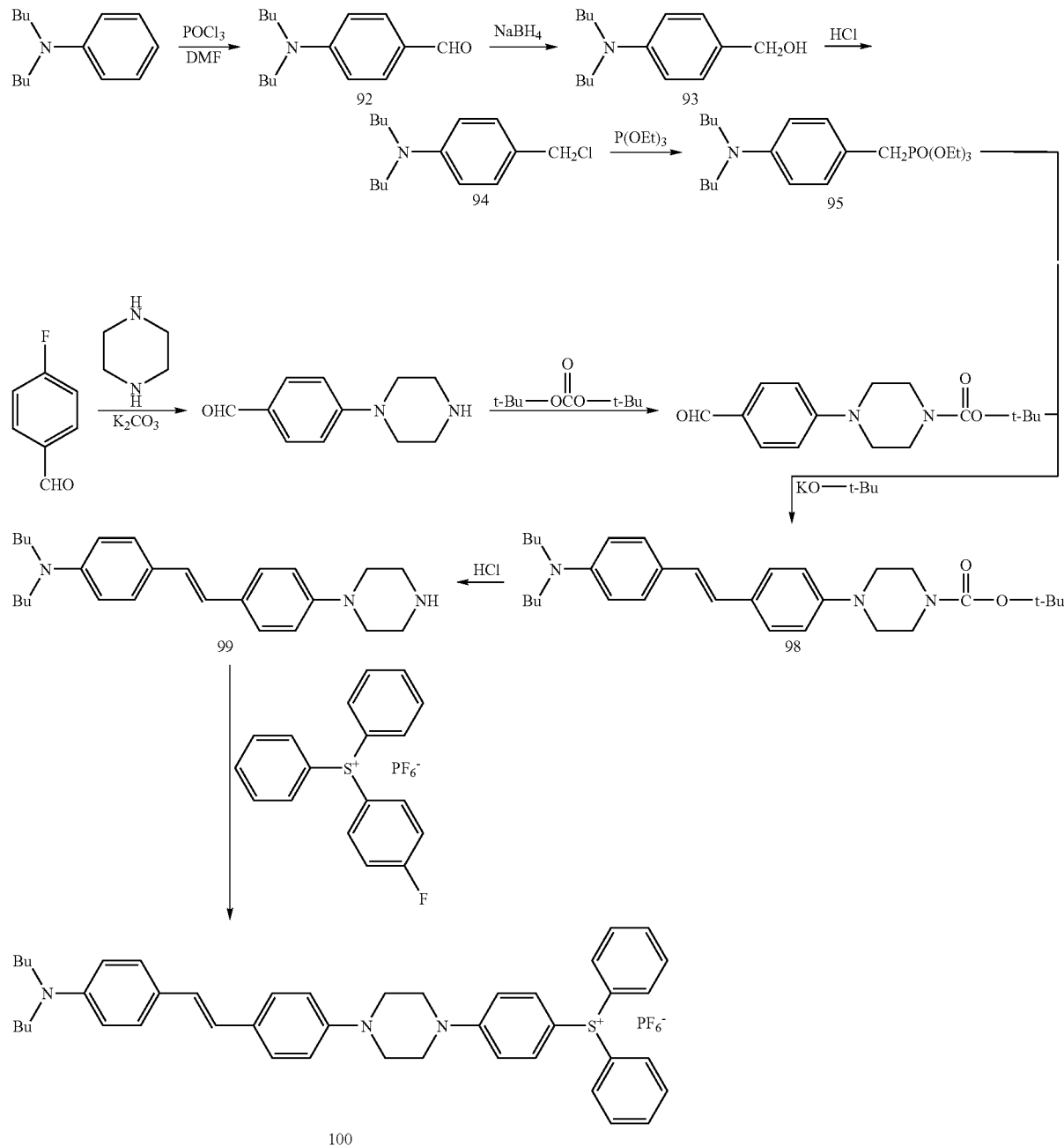

Bistyiylbenzene dye-sulfonium compound 106 was prepared in six steps. In order to increase solubility of the compound, n-butyl substituents were employed on the nitrogen, along with two methoxy groups on the central ring. 1,4-dimethoxyl benzene reacted with formaldehyde in concentrated hydrochloric acid in the presence of hydrogen chloride gas to give 2,5-di(chloromethyl)-1,4-dimethoxyl benzene 101 in a yield of 56.2%. The reaction of 101 with triethylphosphite gave tetraethyl 2,5-bismethoxyl-p-xylene phosphonate (102) in a yield of 94.3%. 102 reacted with N,N-di-n-butyl-4-aminobenzaldehyde under Homer-Emmons conditions to give diethyl 4-{(E)-2-[4-(dibutylamino)phenyl}ethenyl}-2,5-dimethoxybenzyl phosphonate (103) in a yield of 57.8%; excess 102 and a relatively large amount of solvent were used in the experiment to decrease the possibility of reaction on both phosphonates. The Homer-Emmons reaction between 103 and 97 gave N-(4-{(E)-2-{4-[4-(1-tert-butoxycarbonyl)piperazin-1-yl]phenyl}ethenyl)-2,5-dimethoxyphenyl]ethenyl}phenyl) N,N-dibutylamine (104) in a yield of 71.4%. Deprotection of 104 gave 4-N,N-{2,5-dimethoxy-4-[(E)-2-(4-piperazin-1-ylphenyl)ethenyl]phenyl}ethenyl)aniline (105) in a yield of 85.7%. Finally, the nucleophilic substitution reaction of 105 with 4-fluorophenyl diphenylsulfonium hexafluorophosphate gave the target compound 106 in a yield of 70.4%.
Scheme 13: Preparation of a triphenylsulfonium salt linked through piperazine to a bis(styryl)benzene-based two-photon chromophore
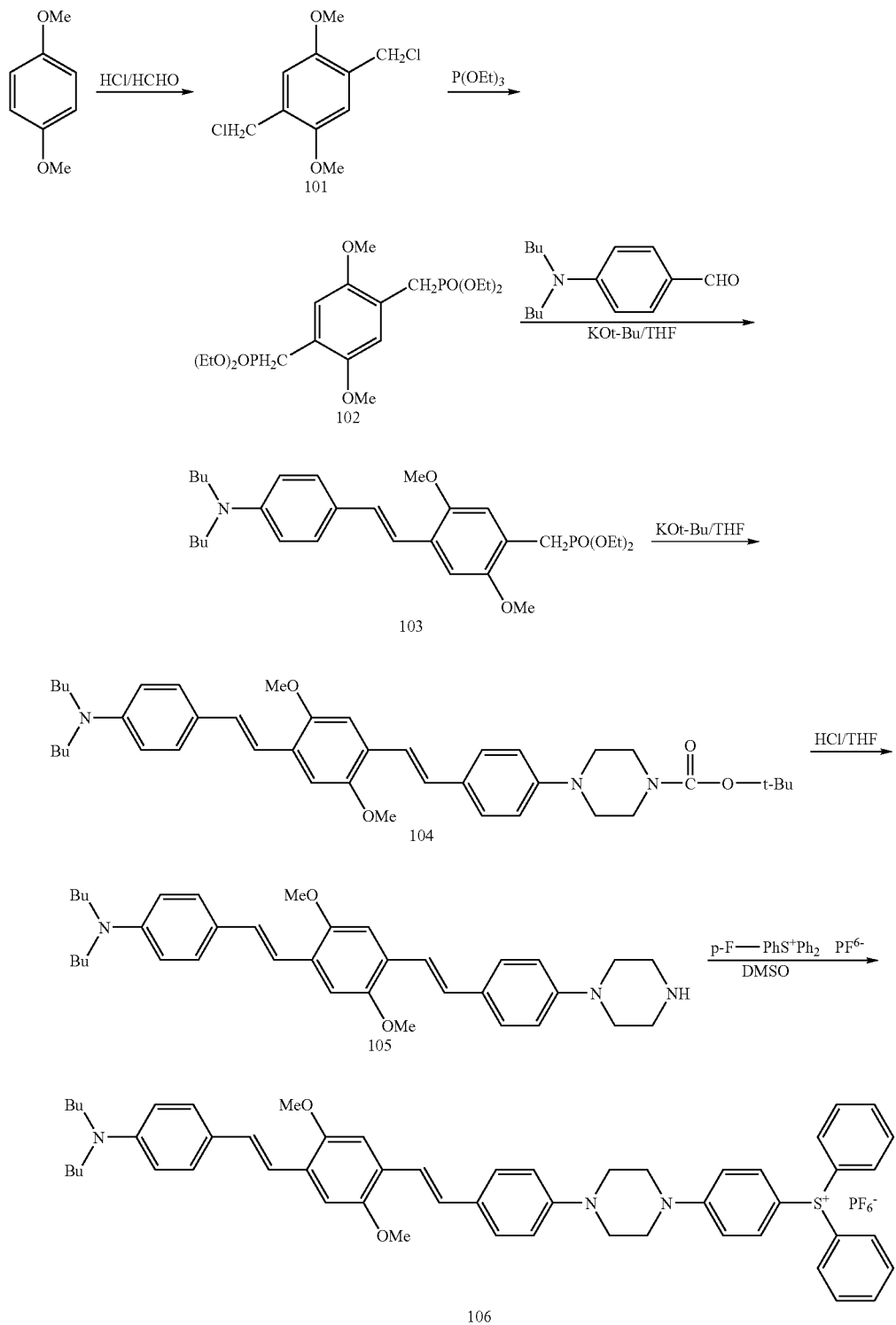

Scheme 14 shows the synthesis of a precursor suitable for conversion to a two-photon dye doubly functionalized with triarylsulfonium groups.

Scheme 14: Preparation of a precursor for a disulfonium-functionalized piperazine-substituted bis(styryl)benzene.

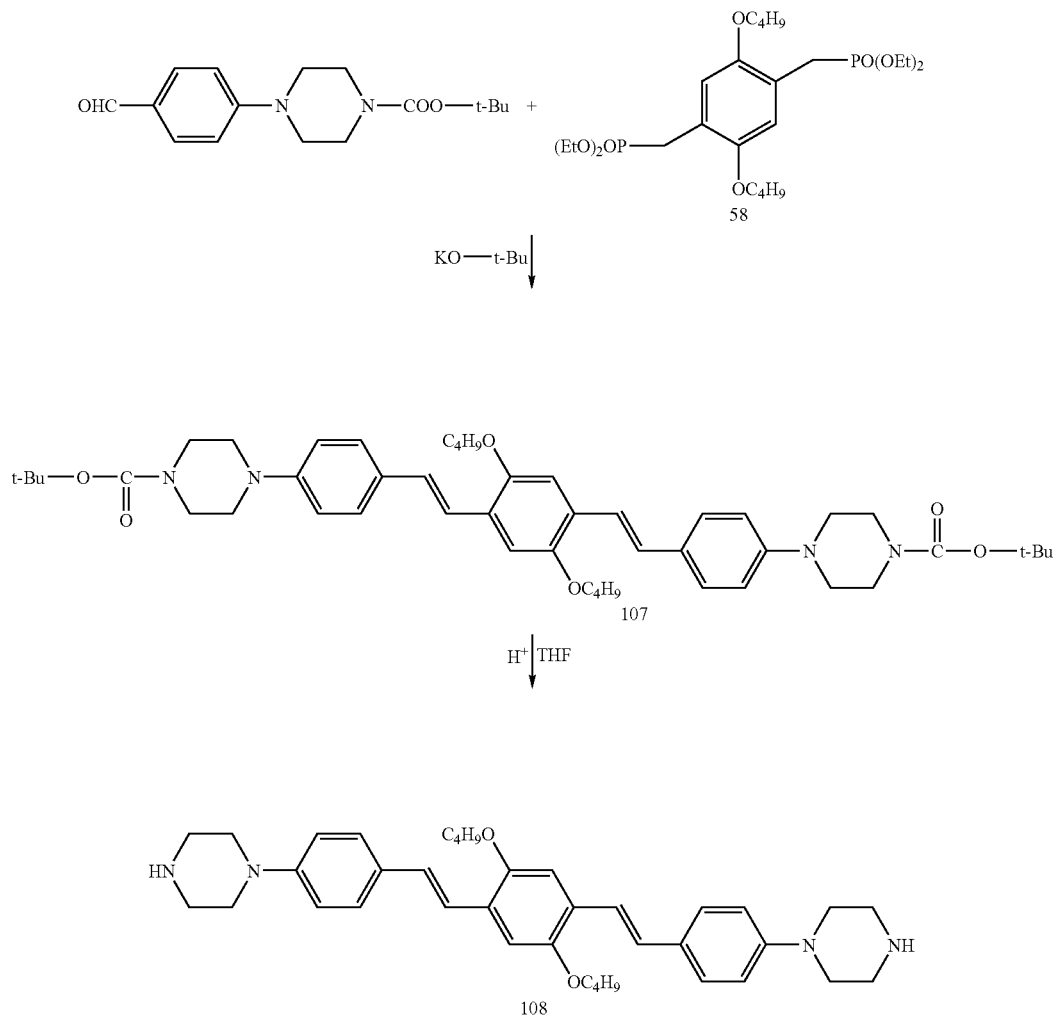

Scheme 15 shows examples of two-photon chromophores containing the julolidine that have been synthesized and that are potential two-photon sensitizers with diphenyliodonium salts through a charge-transfer interaction.

Scheme 15. Examples of julolidine-based two-photon chromophores.

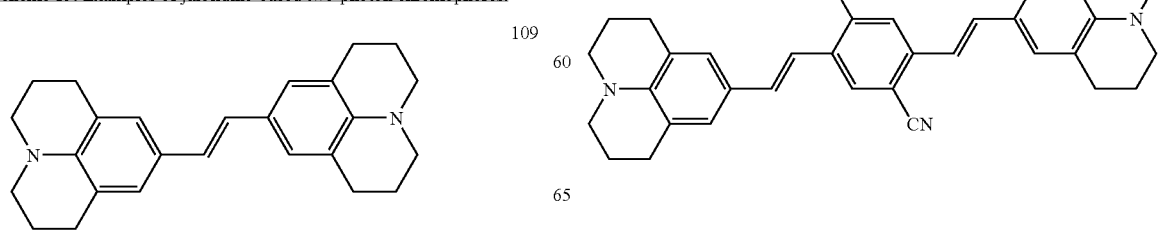

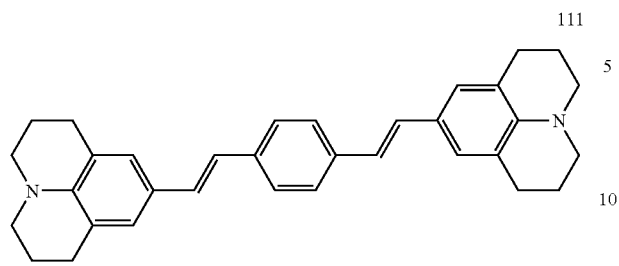
Scheme 16 summarizes acid quantum-yield data for some of the photoacids described above.
Scheme 16: Acid-generation quantum yields of different sulfonium salts
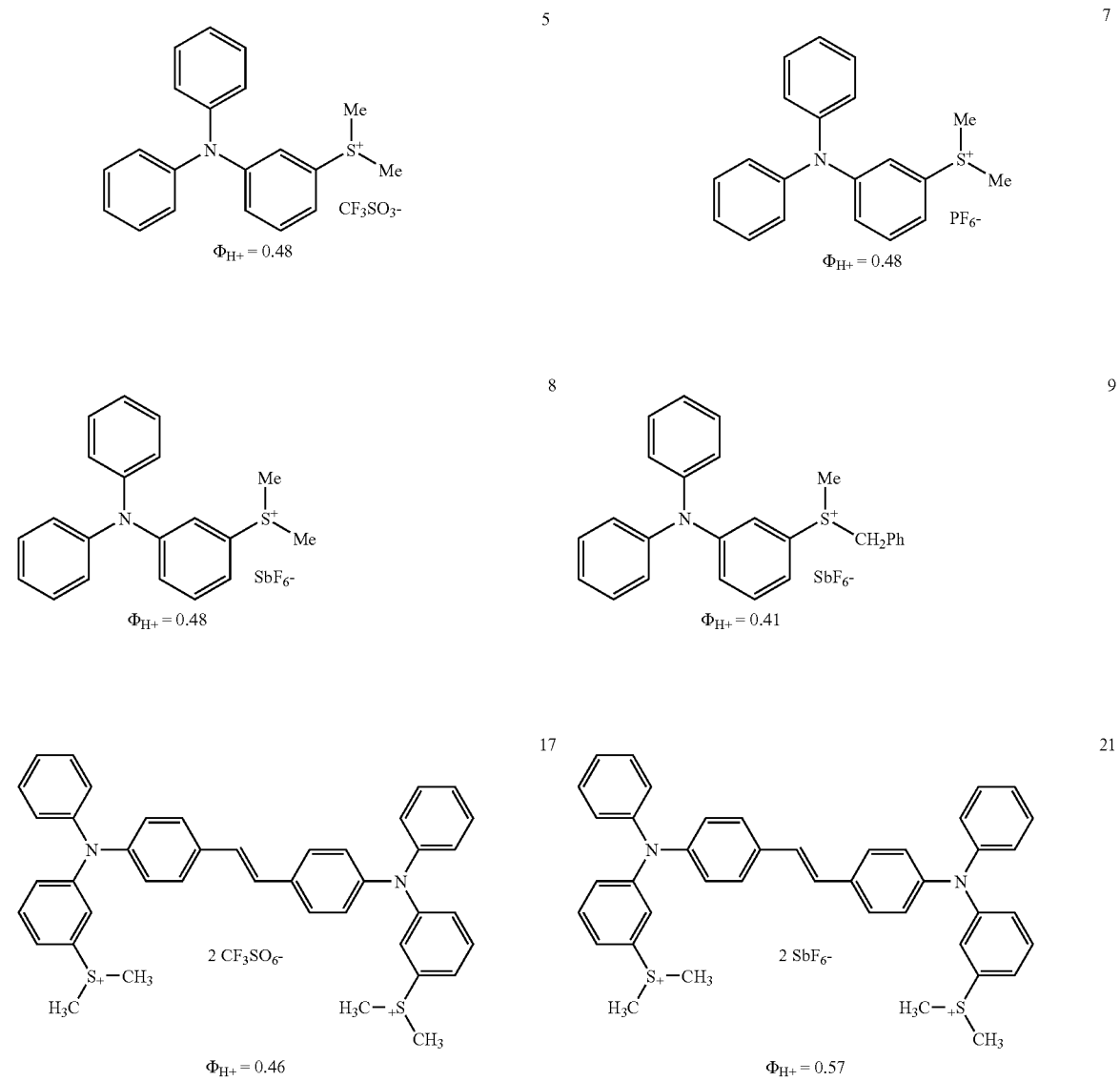

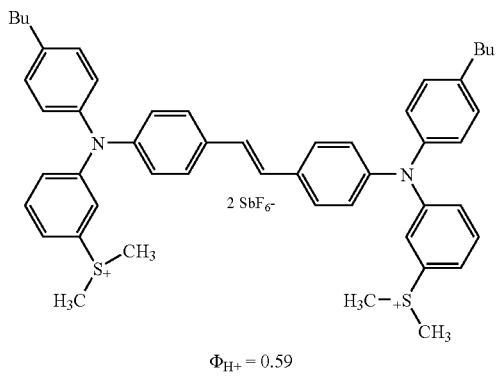
$\Phi_{H+} = 0.59$
23
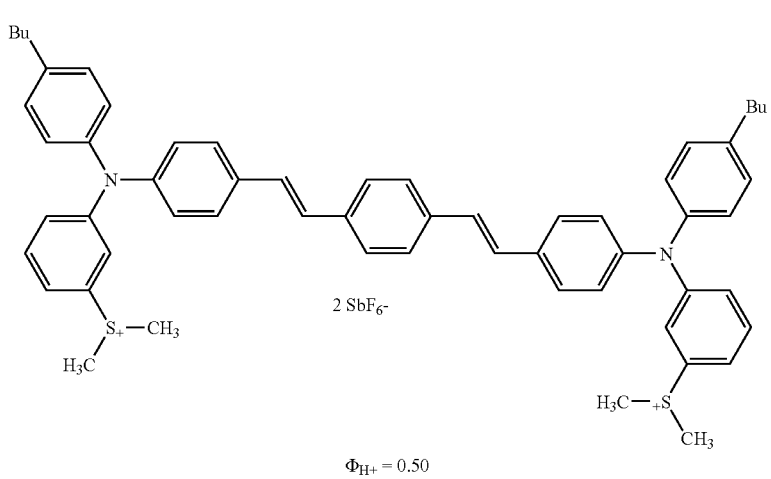
$\Phi_{H+} = 0.50$
41
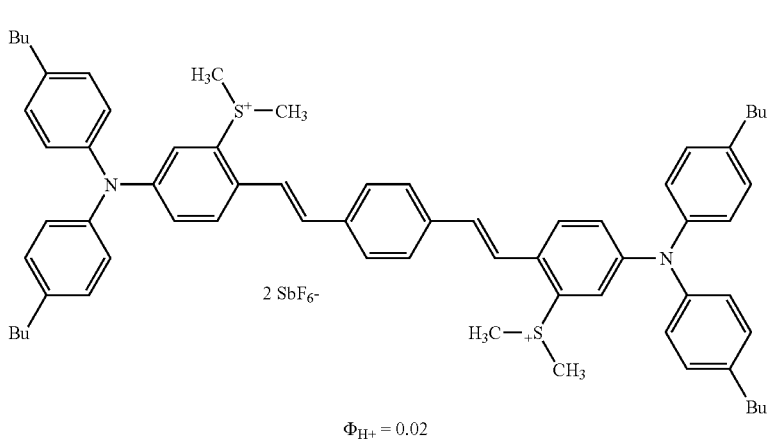
$\Phi_{H+} = 0.02$
52
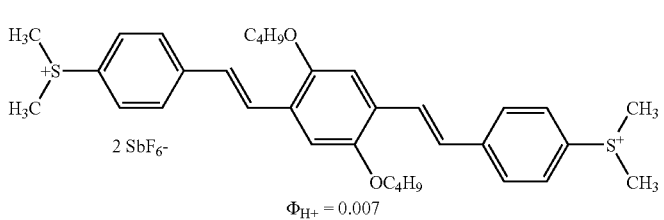
$\Phi_{H+} = 0.007$
61

-continued

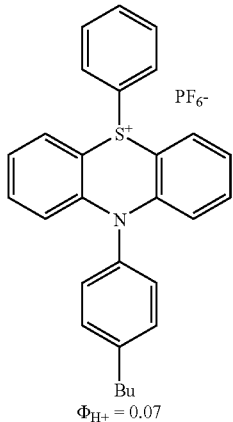

84

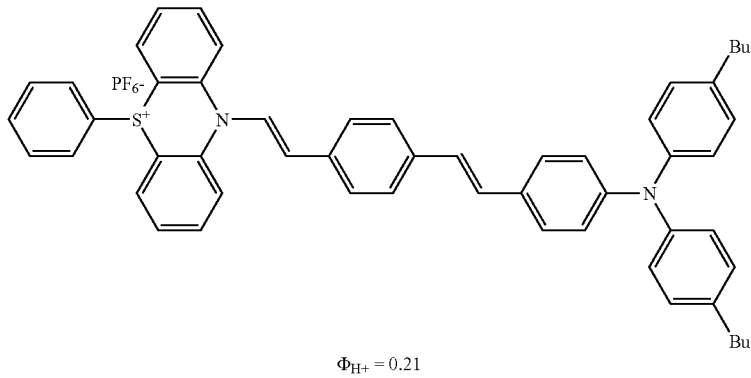

87

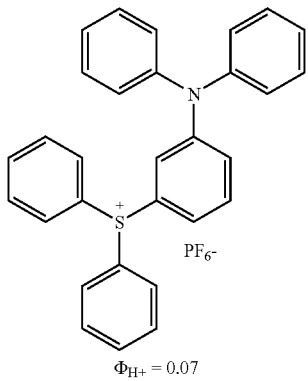

91

Cationic Photopolymerization

FIG. 3 shows a comparison of the photopolymerization of cyclohexene oxide using 5, 7, 8 and 9 as initiators. In accord with previous observations, large anion-dependent variations in the photopolymerization rate were observed. Sulfonium salt 5, which has a triflate counterion, does not initiate polymerization, even after one hour of irradiation. In contrast, 8 and 9, having a $SbF_6^-$ anion, rapidly initiate polymerization, leading to 90% conversion to polymer in 130 seconds. 8 and 9 were found to initiate polymerization with extremely short induction times relative to triphenylsulfonium hexafluoroantimonate (TPS), when irradiated at 300 nm, under otherwise identical conditions. This demonstrates that triphenylamine sulfonium salts are highly efficient cationic initiators that are sensitive to 300 nm radiation.

The photopolymerization of cyclohexene oxide initiated by different dye sulfonium salts was measured. From the % conversion versus time curve (FIG. 4), it can be seen that these three sulfonium salts have a high initiation ability upon irradiation at 419 nm.

Radical Photopolymerization

A typical formulation of epoxy acrylate CN 115 (Sartomer Company, Inc.), initiator, and tetrahydrofuran (20% by weight of CN115) was used for radical polymerization experiments and the conversion of acrylate was monitored using IR spectroscopy at 810 cm$^{-1}$. Upon irradiation, mono- or bi-molecular systems of dye/sulfonium salt undergo inter- or intra-molecular electron-transfer reactions to produce the active phenyl radical species, and the radical cation of the dye. The latter might further undergo a secondary reaction to form colorless photo-products, while the phenyl radical can initiate a radical polymerization of unsaturated acrylates or resins. FIG. 5 illustrates radical polymerization initiated by compound 87. The plots of conversion vs. irradiation time (FIG. 6a, 6b) show that both the combination systems 99 or 105 with triphenylsulfonium hexafluorophosphate (TPS'), and the single molecule systems 100 or 106 are more effective than 99 or 105 alone. But single molecule systems 100 and 106 are the most efficient initiators, and both the polymerization rate (initial slope of a curve) and maximal conversion are higher than for others under the same conditions. The polymerization rate also decreases with the decrease of concentration of initiator 100 or 106, but not dramatically. In contrast, the concentration of the components of the bimolecular system has a dramatic influence on the polymerization, the decrease of concentration of 99, 105 or sulfonium (TPS) leads to a significant increase of the induction time, a decrease of polymerization rate, and a decrease in maximal conversion. Therefore, the single molecule dye-sulfonium linked radical initiators are highly efficient in viscous media.

Preferable high peak-power lasers (emission wavelengths, and pulse durations) suitable for two-photon/multiphoton excitation of photoacid- and radical-generators include:

Continuous-wave (CW) mode-locked ML) titanium:sapphire
$\lambda_{em}$=690-1050 nm, $\tau_p$~80 fs-80 ps
$\lambda_{em}$=345-525 nm (second harmonic), $\tau_p$~80 fs-80 ps.

Optical parametric oscillator pumped by CW ML Ti:sapphire
$\lambda_{em}$=500-2000 nm (including second-harmonic), $\tau_p$~80 fs.

Amplified ML Ti:sapphire
$\lambda_{em}$=750-900 nm, $\tau_p$~80 fs-80 ps
$\lambda_{em}$=375-450 nm (second harmonic), $\tau_p$~80 fs-80 ps
$\lambda_{em}$=250-300 nm (third harmonic), $\tau_p$~80 fs-80 ps
$\lambda_{em}$=188-225 nm (fourth harmonic), $\tau_p$~80 fs-80 ps.

Optical parametric amplifier (OPA) pumped by amplified ML Ti:sapphire
$\lambda_{em}$=300-10,000 nm (including harmonics), $\tau_p$~80 fs-1 ps.

Q-switched Nd:yttrium aluminum garnet (Nd:YAG)
$\lambda_{em}$=1064 nm, $\tau_p$~5 ns
$\lambda_{em}$=532 nm (second harmonic), $\tau_p$~5 ns
$\lambda_{em}$=355 nm (third harmonic), $\tau_p$~5 ns
$\lambda_{em}$=266 nm (fourth harmonic), $\tau_p$~5 ns.

Q-switched Nd:yttrium vanadate (Nd:YVO$_4$)
$\lambda_{em}$=1064 nm, $\tau_p$~5 ns
$\lambda_{em}$=532 nm (second harmonic), $\tau_p$~5 ns
$\lambda_{em}$=355 nm (third harmonic), $\tau_p$~5 ns
$\lambda_{em}$=266 nm (fourth harmonic), $\tau_p$~5 ns.

Q-switched Nd:yttrium lanthanum fluoride (Nd:YLF$_4$)
$\lambda_{em}$=1054 nm, $\tau_p$~5 ns
$\lambda_{em}$=527 nm (second harmonic), $\tau_p$~5 ns
$\lambda_{em}$=351 nm (third harmonic), $\tau_p$~5 ns
$\lambda_{em}$=264 nm (fourth harmonic), $\tau_p$~5 ns.

Mode-locked Q-switched Nd:glass
$\lambda_{em}$=1060 nm, $\tau_p$~5-50 ps
$\lambda_{em}$=527 nm (second hanmonic), $\tau_p$~5 ns -50 ps
$\lambda_{em}$=351 nm (third harmonic), $\tau_p$~5 ns -50 ps
$\lambda_{em}$=264 nm (fourth harmonic), $\tau_p$~5 ns -50 ps.

Dye lasers
$\lambda_{em}$~225-940 nm (including harmonics)
$\tau_p$~500 ps-5 ns, (<5 fs in special cases).

Ruby
$\lambda_{em}$=694 nm, $\tau_p$~5 ns
$\lambda_{em}$=347 nm (second harmonic), $\tau_p$~5 ns.

Alexandrite
$\lambda_{em}$=378 nm (second harmonic), $\tau_p$~5 ns.

Picosecond diode lasers
$\lambda_{em}$=635-1060 nm, $\tau_p$~70-150 ps.

Erbium-doped fiber lasers
$\lambda_{em}$=1550 nm, 775 nm (second harmonic), $\tau_p$=100 fs.

The two-photon absorption cross-sections, δ, are measured by the two-photon induced fluorescence method (Xu, C.; Webb, W. W. *J. Opt. Soc. Am. B*, 1996, 13, 481-491) using both femtosecond and nanosecond pulsed lasers as excitation sources. The reference standards used in the measurement of δ are (1,4-bis(2-methylstyrl)benzene in cyclohexane, rhodamine B in methanol, fluorescein in pH 11 water, and coumarin 307 in methanol), for which the two-photon properties have been well characterized in the literature (Xu, C.; Webb, W. W., *J. Opt. Soc. Am. B*, 1996, 13, 481-491; Kennedy, S. M.; Lytle, F. E. *Anal Chem.*, 1986, 58, 2643-2647). The δ for a given compound is obtained from experimentally determined parameters using:

$$\delta_s = \frac{S_s \eta_r \Phi_r C_r}{S_r \eta_s \Phi_s C_s} \delta_r$$

where S is the detected two-photon induced fluorescence signal, η is the fluorescence quantum yield, and C is the concentration of the chromophore. Φ is the collection efficiency of the experimental setup and accounts for the wavelength dependence of the detectors and optics as well as the difference in refractive indexes between the solvents in which the reference (r) and sample (s) compounds are dissolved. The measurements are conducted in a regime where the fluorescence signal shows a quadratic dependence on the intensity of the excitation beam, as expected for two-photon induced emission.

The nanosecond-pulse measurements are performed using an experimental set-up described previously (Rumi, M; Ehrlich, J. E; Heikal, A. A.; Perry, J. W.; Barlow, S.; Hu, Z.; McCord-Maughon, D.; Parker, T. C.; Röckel, H.; Thayumanavan, S.; Marder, S. R.; Beljonne, D.; and Brédas, J.-L. *J. Am. Chem. Soc.*, 2000, 122, 9500-9510). The excitation source is a Nd:YAG-pumped optical parametric oscillator (Quanta-Ray, MOPO 730) with a 5-ns pulse duration and 10 Hz repetition rate, tunable over the wavelength range of 430-700 and 730-2000 nm. A two-arm set-up is used to correct for fluctuations in the laser intensity. The beam is approximately collimated over the 1-cm pathlength of the glass cuvette. The concentrations of the solutions are ~$10^{-4}$ M for both the sample and reference compounds. In each arm, the two-photon-induced fluorescence is collected at right angles to the excitation beam and focused onto a photomultiplier tube (PMT). Short wave pass filters are used to block scattered light. The signals are averaged over about 300 pulses.

The femtosecond-pulse measurements are performed using a Ti:Sapphire laser (Spectra-Physics, Tsunami) as the excitation source. This laser generates ~100 fs pulses at a repetition rate of 82 MHz in the wavelength range of 710-1000 nm. A one-arm set-up is utilized in this experiment, and the sample and reference measurements are taken in series for each excitation wavelength. The beam is focused into a 1-cm pathlength cell containing solutions at concentrations of $10^{-4}$ M-$10^{-6}$ M. Fluorescence is detected at 90° with respect to the excitation beam by a PMT after a series of short-wave-pass filters and a monochromator to block out scattered light. The fluorescence collection is performed at the same detection wavelength for reference and sample compounds. The PMT is operated in a single photon counting regime and its output is amplified and read by a frequency counter. The output signal is averaged for 30 seconds and recorded.

The magnitude of the two-photon absorptivity of a generic medium can be characterized by the two-photon absorption coefficient, $\beta$ (having units of, e.g., cm/W). $\beta$ is a macroscopic property of a given material that depends upon the specific composition. For the case of a material comprised in part or entirely of molecules, the macroscopic two-photon absorptivity can be related to the molecular two-photon absorption cross-section, $\delta$, by $\beta=\delta C/h\nu$, where C is the number density of the molecules in the material (in units of molecules/cm$^3$), h is the Planck constant, and $\nu$ is the frequency of the radiation used to two-photon excite the medium (in units of s$^{-1}$). $\beta$ can be measured using several techniques, including nonlinear transmission and "Z-scan", as described in R. L. Sutherland's *Handbook of Nonlinear Optics* (New York, Marcel Dekker, 1996). At a two-photon excitation wavelength of 800 nm, typical photopolymer compositions comprised of conventional photoinitiators will have two-photon absoiptivities in the range of $\beta=0$ to $1.6\times10^{-11}$ cm/W, and more typically, $\beta<1.6\times10^{-12}$ cm/W.

Several preferred embodiments are given below in paragraphs A-I.

A. A composition of matter which includes a sulfonium, selenonium, iodonium salt, or other acid- or radical generator containing:
- a two-photon absorbing chromophore with a two-photon cross-section $>50\times10^{-50}$ cm$^4$ s/photon wherein the excited state of the chromophore can activate the acid/radical generator towards undergoing a molecular rearrangement generating a Brønsted or Lewis acid and/or radical;
- a group or bond that links the chromophore to the acid/radical generator, bringing the chromophore and the acid/radical generator into close spatial proximity; and
- an anion(s).

B. A composition of matter which includes a sulfonium, selenonium, or iodonium salt, or other acid- or radical generator containing:
- a two-photon absorbing chromophore with a two-photon cross-section $>50\times10^{-50}$ cm$^4$ s/photon, wherein the excited state of the chromophore can activate the acid/radical generator towards undergoing a molecular rearrangement generating a Brønsted or Lewis acid and/or radical;
- an electrostatic interaction between the chromophore and the acid/radical generator, the attractive energy associated with which is greater than 3 kcal/mol, and which keeps both moeities in close spatial proximity on average, when both compounds are present in the concentrations of 0.001 M-2M; and
- an anion(s).

C. A composition of matter which includes a sulfonium, selenonium, or iodonium salt, or other acid- or radical generator containing:
- a two-photon absorbing chromophore with a two-photon cross-section $>50\times10^{-50}$ cm$^4$ s/photon wherein the excited state of the chromophore can activate the acid/radical generator towards undergoing a molecular rearrangement generating a Brønsted or Lewis acid and/or radical;
- an electrostatic interaction between the chromophore and the acid/radical generator, the attractive energy associated with which is greater than 3 kcal/mol, and which keeps both compounds in close spatial proximity on average, when both compounds are present in the concentrations of 0.001 M -2M;
- wherein the chromophore itself is an anion.

D. A composition according to embodiment A above, in which a two-photon absorbing chromophore with a two-photon cross-section $>50\times10^{-50}$ cm$^4$ s/photon, wherein the excited state of the chromophore can activate the radical/acid generator towards undergoing a molecular rearrangement generating a Brønsted or Lewis acid and/or radical, and the chromophore is a molecule in which two donors are connected to a conjugated $\pi$-electron bridge (abbreviated "D-$\pi$-D" motif).

E. A composition according to embodiment A above, in which a two-photon absorbing chromophore with a two-photon cross-section $>50\times10^{-50}$ cm$^4$ s/photon, wherein the excited state of the chromophore can activate the radical/acid generator towards undergoing a molecular rearrangement generating a Brønsted or Lewis acid and/or radical, and the chromophore is a molecule in which two donors are connected to a conjugated $\pi$-electron bridge which is substituted with one or more electron accepting groups (abbreviated "D-A-D" motif).

F. A composition according to embodiment A above, in which a two-photon absorbing chromophore with a two-photon cross-section $>50\times10^{-50}$ cm$^4$ s/photon, wherein the excited state of the chromophore can activate the radical/acid generator towards towards undergoing a molecular rearrangement generating a Brønsted or Lewis acid and/or radical, and the chromophore is a molecule in which two acceptors are connected to a conjugated $\pi$-electron bridge (abbreviated A-$\pi$-A" motif).

G. A composition according to embodiment A above in which a two-photon absorbing chromophore with a two-photon cross-section $>50\times10^{-50}$ cm$^4$ s/photon, wherein the excited state of the chromophore can activate the radical/acid generator towards undergoing a molecular rearrangement generating a Brønsted or Lewis acid and/or radical, and the chromophore is a molecule in which two acceptors are connected to a conjugated $\pi$-electron bridge which is substituted with one or more electron donating groups (abbreviated "A-D-A" motif).

H. A method of generating a Brønsted or Lewis acid or radical, which includes a step of exposing a compound that includes a sulfonium, selenonium, or iodonium salt, or other acid- or radical generator; a chromophore having the formula $D_1$-$\pi$-$D_2$ wherein $D_1$ and $D_2$ are electron donor groups; and 7 includes a bridge of $\pi$-conjugated bonds connecting $D_1$ and $D_2$; and a group which links the chromophore to the radical/acid generator, bringing the chromophore and the radical/acid generator into close spatial proximity; and an anion;to pulsed laser radiation and converting the compound to a multi-photon electronically excited state upon simultaneous absorption of at least two photons of the radiation by the compound, wherein the sum of the energies of all of the absorbed photons is greater than or equal to the transition energy from a ground state of the compound to the multi-photon excited state, and wherein the energy of each absorbed photon is less than the transition energy between the ground state and the lowest single-photon excited state of the compound and is less than the transition energy between the multi-photon excited state and the ground state, and the excited state is capable of transforming the salt through a sequence of one or more reactions to a Brønsted or Lewis acid and/or radical.

I. A method of generating a Brønsted or Lewis acid and/or radical, which includes:
  i. exposing a compound, which includes a sulfonium, selenonium, or iodonium salt, or other acid- or radical generator; a chromophore and a group or bond which links the chromophore to the acid/radical generator, bringing the chromophore and the acid/radical generator into close spatial proximity; and an anion(s);

to pulsed laser radiation;

ii. converting the compound to a multi-photon electronically excited state upon simultaneous absorption of at least two photons of the radiation by the compound, wherein the sum of the energies of all of the absorbed photons is greater than or equal to the transition energy from a ground state of the compound to the multi-photon excited state and wherein the energy of each absorbed photon is less than the transition energy between the ground state and the lowest single-photon excited state of the compound and is less than the transition energy between the multi-photon excited state and the ground state; and;

iii. generating a Brønsted or Lewis acid and/or a radical from the excited compound through a sequence of one or more reactions.

EXAMPLES

Having generally described this invention, a further understanding can be obtained by reference to certain specific examples, which are provided herein for purposes of illustration only and are not intended to be limiting unless otherwise specified.

Example 1

Preparation of 3-bromothioanisole (1). 3-bromobenzenethiol (5 g, 26.44 mmol) was added to a solution of sodium methoxide (1.43 g, 26.48 mmol) in 20 ml of anhydrous methanol. The mixture was stirred for 30 min under nitrogen at room temperature and a solution of methyl iodide (4.51 g, 31.77 mmol) in 20 ml anhydrous methanol was then added. The reaction mixture was stirred overnight at room temperature, poured into 2 M aqueous NaOH solution (30 ml) and extracted three times with ether (60 ml×3). The combined organic layer was washed with saturated sodium chloride solution and dried over anhydrous magnesium sulfate. After removal of solvent, the product was purified by distillation at 80° C. (0.3 mmHg) and isolated in 86.1% (4.62 g) yield. $^1$H NMR(CDCl$_3$, 500 MHz) δ ppm: 2.44 (s, 3H, CH$_3$), 7.1-7.4 (m, 4H, Ar—H)GC-MS(relative intensity %): 202, 204(1:1, 100, M$^+$), 187, 189(1:1, 11, 3-BrPhS$^+$).

Example 2

Preparation of 3-bromophenyl benzyl sulfide (2). 3-bromobenzenethiol (5 g, 26.44 mmol) was added to a solution of sodium methoxide (1.43 g, 26.48 mmol) in 20 ml of anhydrous methanol. The mixture was stirred for 30 min at room temperature and a solution of benzyl bromide (4.53 g, 26.48 mmol) in 20 ml anhydrous methanol was then added. The reaction mixture was stirred overnight at room temperature, poured into 2M o aqueous NaOH solution (40 ml) and extracted three times with ether (60 ml×3). The combined organic layer was washed with saturated sodium chloride solution and dried over anhydrous magnesium sulfate. After removal of solvent, the product was purified by distillation at 161° C., 0.3 mmHg and isolated in 85.5% (6.31 g) yield. $^1$H NMR (CDCl$_3$, 500 MHz) δ ppm: 4.12 (s, 2H, CH$_2$), 7.0-7.5 (m, 4H, Ar—H)GC-MS (relative intensity %): 278, 280 (1:1, 30.8, M$^+$), 91(100, PhCH$_2$$^+$).

Example 3

Preparation of 3-methylthiotriphenylamine (3). 3-bromothioanisole (1) (2.0 g, 9.85 mmol) was added to a solution of tris(dibenzylideneacetone)dipalladium (Pd$_2$(dba)$_3$) (0.28 g, 0.306 mmol) and bis(diphenylphosphino)ferrocene (IPPF) (0.245 g, 0.442 mmol) in dry toluene (20 mL) under a nitrogen atmosphere at room temperature. The resultant mixture was stirred for 10 minutes. Sodium tert-butoxide (2.17 g) and diphenylamnine (1.67 g, 9.85 mmol) were then added and stirred at 90° C. for 24 h. The reaction mixture was poured into 20 mL of water, extracted three times with ether (3×60 mL) and dried over anhydrous magnesium sulfate. The product was purified by flash column chromatography using 2% ethyl acetate in hexanes as eluant to give 1.87 g of a pale yellow oil (65.2%). The product was estimated to be greater than 95% pure by $^1$H NMR and was used in next step without fiiier purification. $^1$H NMR (500 MHz, CDCl$_3$) δ ppm: 7.25 (t, br, J=7.5 Hz, 4H), 7.14 (t, J=8.2 Hz, 1H), 7.08 (d, br, J=8.2 Hz, 4 H), 7.02 (t, br, J=7.5 Hz, 2H), 6.97 (t, J=2.0 Hz, 1H), 6.87 (d, br, J=8.0, 1H), 6.82 (d, br, J=8.0, 1H), 2.20 (s, 3H, CH$_3$). $^{13}$C NMR (125 MHz, CDCl$_3$) δppm: 148.3, 147.5, 139.3, 129.4. 129.2, 124.3, 122.9, 121.5, 120.5, 120.2, 15.6. EIMS (relative intensity %): 291(100, M$^+$).

Example 4

Preparation of 3-benzylthiotriphenylamine (4). 3-bromophenyl benzyl sulfide (3) (1.86 g, 6.67 mmol) was added to a solution of tris(dibenzylideneacetone)dipalladium (Pd$_2$(dba)$_3$) (0.15 g, 0.16 mmol) and bis(diphenylphosphino)ferrocene (DPPF) (0.11 g, 0.20 mmol) in dry toluene (20 mL) under nitrogen atmosphere at room temperature. The resultant mixture was stirred for 10 minutes. Sodium tert-butoxide (1.42 g) and diphenylamine (1.13 g, 6.69 mmol) were then added to this solution and stirred at 90° C. for 24 h. The reaction mixture was poured into 20 mL of water, extracted three times with ether (3×60 mL) and dried over anhydrous magnesium sulfate. The product was purified by flash column chromatography using 2% ethyl acetate in hexanes as eluant to give 1.53 g of a pale yellow oil (62.5%). The product was estimated to be greater than 95% pure by $^1$H NMR and was used in next step without finther purification. $^1$H NMR (500 MHz, CDCl$_3$) δppm: 7.2-7.3 (m, overlap, 9H), 7.10 (t, J=8.0 Hz, 1H), 7.0-7.06 (m, overlap, 7H), 6.93 (d, br, J=8.0 Hz, 1H), 6.86 (d, br, J=8.0 Hz, 1H), 4.04 (s, 2H, CH$_2$). $^{13}$C NMR (125 MHz, CDCl$_3$) δ ppm: 148.2, 147.4, 137.4, 137.2, 129.4, 129.2, 128.7, 128.4, 127.1, 124.4, 123.4, 123.0, 121.6. 38.7 (One carbon was not observed). EIMS (relative intensity %): 367 (100, M$^+$).

Example 5

Preparation of [3-(N,N-diphenyl)amino]phenyl dimethyl sulfonium trifluoromethanesulfonate (5). 3-methylthiotriphenylamine (3) (1.77 g, 6.08 mmol) was dissolved in 30 mL of dry methylene chloride and cooled to −78° C. in the dark. To this solution was added via syringe 0.76 mL (1.10 g, 6.70 mmol) of methyl trifluoromethanesulfonate under nitrogen and stirred for 30 minutes while the temperature was maintained at −78° C. The resultant mixture was then stirred overnight at room temperature. 60 mL of ether was added to the mixture, resulting in the slow formation of white crystals. The crystals were collected by filtration and washed three times with ether. The product was purified by recrystallization from methylene chloride and ether at room temperature and isolated in 2.45 g (88.6%) yield. $^1$H NMR (500 MHz, d$_6$-DMSO)

δ ppm: 7.61 (d, br, J=8.5 Hz, 1H), 7.58 (d, J=8.5 Hz, 1H), 7.55 (t, J=1.7 Hz, 1H), 7.38 (t, br, J=8.0 Hz, 4H), 7.13-7.20 (m, 3H), 7.09 (d, br, J=7.5, 4H), 3.19 (s, 6H, $CH_3$). Anal. Calcd. for $C_{21}H_{20}NO_3S_2F_3$: C, 55.37; H, 4.42; N, 3.09. Found: C, 55.26; H, 4.59; N, 3.19.

Example 6

Preparation of [3-(N,N-diphenyl)amino]phenyl dimethyl sulfonium hexafluorophosphate (7). A fresh 20 mL solution of $KPF_6$ (1.14 g, 5.98 mmol) in water was added to a solution of [3-(N,N-diphenyl)amino]phenyl dimethyl sulfonium trifluoromethanesulfonate (1.3 g, 2.86 mmol) in 15 mL of acetone. The mixture was stirred for 2 hours at room temperature in the dark. The solid was collected by filtration and redissolved in 10 mL of acetone. This anion-exchange procedure was repeated three times. The resultant white solid was washed three times with water and ether. The solid was purified by two precipitations from 10 mL of acetone solution through the addition of 50 mL of diethyl ether. The final product yield was 1.08 g (83.6%). $^1$H NMR (500 MHz, $d_6$-DMSO) δ pm: 7.62 (d, J=7.5 Hz, 1H), 7.57 (d, J=8.0 Hz, 1H), 7.55 (s, 1H), 7.38 (t, br, J=8.2 Hz, 4H), 7.13-7.20 (m, 3H, 7.09 (d, J=8.5, 4H), 3.19 (s, 6H, $CH_3$). Anal. Calcd for $C_{20}H_{20}NSF_6P$: C, 53.22; H, 4.47; N, 3.10. Found: C, 53.20; H, 4.29; N, 3.13.

Example 7

Preparation of [3-(N,N-diphenyl)amino]phenyl dimethyl sulfonium hexafluoroantimonate (8). A fresh 20 mL portion of $NaSbF_6$ (1.14 g, 4.40 mmol) in water was added to a solution of [3-(N,N-diphenyl)amino]phenyl dimethyl sulfonium trifluoromethanesulfonate (1.0 g, 2.19 mmol) in 10 mL of acetone. The mixture was stirred for 2 hours at room temperature in the dark. The solid was collected by filtration and redissolved in 10 mL of acetone. The above anion-exchange was repeated three times. The resulting white solid was washed three times with water and ether. The product was purified by two precipitations from 10 mL of acetone solution through the addition of 50 mL of diethyl ether. The final product yield was 1.02 g (85.9%). $^1$H NMR (500 MHz, $d_6$-DMSO) δppm: 7.62 (d, J=7.5 Hz, 1H), 7.57 (d, J=8.0 Hz, 1H), 7.55 (s, 1H), 7.38 (t, br, J=8.2 Hz, 4H), 7.13-7.20 (m, overlap, 3H), 7.09 (d, J=8.5, 4H), 3.19 (s, 6H, $CH_3$). Anal. Calcd for $C_{20}H_{20}NSF_6Sb$: C, 44.30; H, 3.72; N, 2.58. Found: C, 44.29; H, 3.76; N, 2.54.

Example 8

Preparation of [3-(N,N-diphenyl)amino]phenyl benzyl methyl sulfonium hexafluoroantimonate (9). 3-Benzylthiotriphenylamine (1.48 g, 4.03 mmol) was dissolved in 30 mL of dry methylene chloride and cooled to −78 ° C. in the dark. To this solution was added via syringe 0.46 mL (0.67 g, 4.07 mmol) of methyl trifluoromethanesulfonate under nitrogen. The mixture was then stirred for 30 minutes while the temperature was maintained at −78° C. The mixture was then allowed to warm to room temperature and was stirred overnight. 60 mL of ether was added resulting in the formation of a light green oil. The solvent was decanted and the oil was dried in vacuo at room temperature. The product was used in the ion-metathesis described below without further purification.

A fresh 20 mL portion of aqueous $NaSbF_6$ (2.10 g, 8.11 mmol) was added to a solution of [3-(N,N-diphenyl)amino] phenyl benzyl methyl sulfonium trifluoromethane-sulfonate (6) (1.3 g, 2.86 mmol) in 10 mL of acetone. The mixture was stirred for 2 hours at room temperature in the dark. The solid was collected by filtration and redissolved in 10 mL of acetone. The above anion-exchange was repeated three times. The resultant white solid was washed three times with water and ether. The product was purified by re-precipitation twice from 10 mL of acetone solution by the addition of 50 mL diethyl ether giving a final yield of 1.08 g (71.8%). $^1$H NMR (500 MHz, $CD_3COCD_3$) δ ppm: 7.58-7.62 (m, overlap, 2H), 7.55 (t, J=7.7 Hz, 1H), 7.46 (t, J=7.5 Hz, 2H), 7.36 (t, J=7.7 Hz, 4H), 7.25-7.32 (m, 4H), 7.17 (t, J=7.7 Hz, 2H), 7.02 (d, J=8.0, 4H), 5.25 (d, J=12.5 Hz, 1H, $CH_2$), 5.02 (d, J=13.0 Hz, 1H, $CH_2$), 3.52 (s, 3H, $CH_3$). Anal. Calcd for $C_{26}H_{24}NSF_6Sb$: C, 50.51; H, 3.91; N, 2.26. Found: C, 50.42; H, 3.98; N, 2.19.

Example 9

Preparation of trans-4,4'-dibromostilbene (10).[14] 50% aqueous sodium hydroxide (20 ml) was added to a solution of diethyl 4bromobenzyl phosphnate (5.66 g, 18.4 mmol) and 4-bromobenzaldhyde (3.41 g, 18.4 mmol) in benzene (20 ml). Tetra-(n-butyl) ammonium iodide (420 mg) was added and the mixture was refluxed under nitrogen for 30 min. The reaction mixture was allowed to cool and diluted by addition of water (50 ml). A white solid was collected, washed with methanol and ether, and isolated in 51.0% (3.17 g) yield. $^1$H NMR ($CDCl_3$, 500 MHz) δ ppm: 7.48 (d, J=6.4 Hz, 4H), 7.37 (d, J=6.8 Hz, 4H), 7.02 (s, 2H, =CH).

Example 10

Preparation of trans-4,4'-di(phenylamino)stilbene (11). To a solution of tris(di-benzylideneacetone)dipalladium ($Pd_2(dba)_3$) (0.335 g, 0.365 mmol) and bis-(diphenyl-phosphino)ferrocene (DPPF) (0.294 g, 0.530 mmol) in dry toluene (30 ml) under nitrogen atmosphere was added trans-4,4'-dibromostilbene (10) (2.0 g, 5.91 mmol) at room temperature, and the resultant mixture was stirred for 10 min; sodium tert-butoxide (2.6 g) and aniline (1.102 g, 11.83 mmol) were added to this solution and stirred at 90° C. overnight. The solid was collected, washed three times with methanol and ether and isolated in a yield of 87.8% (1.88 g) as an NMR-pure product. $^1$H NM ($CDCl_3$, 500 MHz) δ ppm: 7.0-7.5 (m, 18H, Ar—H), 6.95 (s, 2H, =CH), 5.77 (s, 2H, NH).

Example 11

Preparation of trans-4,4'-di(p-n-butylphenyl)aminostilbene (12). To a solution of tris(di-benzylideneacetone)dipalladium ($Pd_2(dba)_3$) (0.335 g, 0.365 mmol) and bis-(diphenylphosphino)ferrocene (DPPF) (0.294 g, 0.530 mmol) in dry toluene (20 ml) under nitrogen atmosphere was added trans-4,4'-dibromostilbene (10) (2.0 g, 5.91 mmol) at room temperature, and the resultant mixture was stirred for 10 min, sodium tert-butoxide (2.6 g) and 4-n-butyl aniline (1.77 g, 11.83 mmol) were added to this solution and stirred at 90° C. overnight. The solid was collected, washed three times with methanol and ether, and isolated in 68.8% (1.93 g) yield as an NAM-pure product. $^1$H NMR ($CDCl_3$, 500 MHz) δ ppm: 7.38 (d, J=8.0 Hz, 4H), 7.10 (d, J=8.5 Hz, 4H), 7.03 (d, J=8.0 Hz, 4H), 7.0 (d, J=8.5 Hz, 4H), 6.91 (s, 2H, =CH), 5.77 (s, 2H, NH), 2.56 (t, J=7.7 Hz, $CH_2$, 4H), 1.59 (m, $CH_2$, 4H), 1.37 (m, $CH_2$, 4H), 0.94 (t, J=7.5Hz, $CH_3$, 6H).

Example 12

Preparation of trans-4,4'-di(N,N-phenyl m-methylthiophenyl)amino-stilbene (13). To a solution of tris(dibenzylideneacetone) dipalladium ($Pd_2(dba)_3$) (0.14 g, 0.153 mmol) and bis(diphenylphosphino)ferrocene (DPPF) (0.12 g, 0.216 mmol) in dry toluene (10 ml) under a nitrogen atmosphere was added 3-bromothioanisole (1.0 g, 4.93 mmol) at room temperature, and the resultant mixture was stirred for 10 min. Sodium tert-butoxide (1.08 g) and trans-4,4'-diphenylaminostilbene (11) (0.89 g, 2.46 mmol) were added to this solution and stirred at 90° C. overnight. The reaction mixture was poured into water (20 ml), extracted three times with ether (30 ml×3) and dried over anhydrous magnesium sulfate. The yellow product was purified by flash column chromatography using 5% ethyl acetate in hexane as eluant and isolated in 25.5% (0.38 g) yield. $^1H$ NMR ($CDCl_3$, 500 MHz) δ ppm: 6.8-7.4 (m, 26H, Ar—H), 6.95 (s, 2H, =CH), 2.40 (s, 6H, $CH_3$) $^{13}C$ NMR ($CDCl_3$, 125.7 MHz) δppm: 148.0, 147.2, 146.7, 139.4, 132.1, 129.5, 129.3, 127.1, 126.6, 124.6, 123.9, 123.2, 121.7, 120.8, 120.5, 15.6

Anal. Calcd. for $C_{40}H_{34}N_2S_2$: C, 79.17; H, 5.65; N, 4.62. Found: C, 78.84; H, 5.55; N, 4.54.

Example 13

Preparation of trans-4,4'-di(N,N-phenyl m-benzylthiophenyl)amino-stilbene (14). To a solution of tris(dibenzylideneacetone)dipalladium ($Pd_2(dba)_3$) (0.111 g, 0.114 mmol) and bis-(diphenylphosphino)ferrocene (DPPF) (0.087 g, 0.157 mmol) in dry toluene (10 ml) under nitrogen atmosphere was added 3-bromophenyl benzyl sulfide (1 g, 3.58 mmol) at room temperature, and the resultant mixture was stirred for 10 min, sodium tert-butoxide (0.80 g), and trans-4,4'-diphenylaminostilbene (11) (0.649 g, 1.79 mmol) were added to this solution and stirred at 90° C. overnight. The reaction mixture was poured into water (20 ml), extracted three times with ether (30 ml×3) and dried over anhydrous magnesium sulfate. The product was purified by flash column chromatography using 4% ethyl acetate in hexane as eluant and was isolated in 35.2% (0.48 g) yield. $^1H$ NMR ($CDCl_3$, 500 MHz) δ ppm: 6.8-7.4 (m, 36H, Ar—H), 6.95 (s, 2H, =CH), 4.02 (s, 4H, $CH_2$) $^{13}C$ NMR ($CDCl_3$, 125.7 MHz) δ ppm: 148.0, 147.2, 146.7, 137.3, 132.1, 129.5, 129.3, 128.7, 128.5, 127.2, 127.1, 126.7, 124.6, 124.0, 123.7, 123.2, 121.9, 112.7, 38.69 (One carbon was not observed).

Example 14

Preparation of trans-4,4'-di[N,N-(p-n-butylphenyl)m-methylthiophenyl]aminostilbene (15). To a solution of tris (dibenzylideneacetone) dipalladium ($Pd_2(dba)_3$) (0.197 g, 0.215 mmol) and bis(diphenylphosphino)ferrocene (DPPF) (0.156 g, 0.281 mmol) in dry toluene (10 ml) under nitrogen atmosphere was added 3-bromothioanisole (1.30 g, 6.40 mmol) at room temperature, and the resultant mixture was stirred for 10 min., sodium tert-butoxide (1.41 g), and trans-4,4'-di-p-n-butylphenylaminostilbene (12) (1.52 g, 3.20 mmol) were added to this solution and stirred at 90° C. overnight. The reaction mixture was poured into water (20 ml), extracted three times with ether (30 ml×3) and dried over anhydrous magnesium sulfate. The product was purified by flash column chromatography using 3% ethyl acetate in hexanes as eluant, recrystallized from diethyl ether/hexnanes with slow evaporation of ether, and isolated in 30.2% (0.71 g) yield. $^1H$ NMR ($CDCl_3$, 500 MHz) δ ppm: 6.8-7.4 (m, 24H, Ar—H), 6.96 (s, 2H, =CH), 2.59 (t, J=7.7 Hz, $CH_2$, 4H), 2.40 (s, 6H, $CH_3$), 1.60 (m, $CH_2$, 4H), 1.38 (m, $CH_2$, 4H), 0.98 (t, J=7.5 Hz, $CH_3$, 6H) $^{13}C$ NMR ($CDCl_3$, 125.7 MHz) δ ppm: 148.4, 147.1, 144.9, 139.5, 138.5, 132.0, 129.6, 127.3, 126.7, 125.2, 123.7, 121.5, 120.6, 120.3, 35.3, 33.9, 22.7, 15.9, 14.2 (one carbon was not observed)HRMS (FAB): calcd. For $C_{48}H_{50}N_2S_2M^+$718.3415, found 718.3404

Anal. Calcd. for $C_{48}H_{50}N_2S_2$: C, 80.18 H, 7.01; N, 3.90. Found: C, 80.02; H, 6.78; N, 4.17.

Example 15

Preparation of trans-4,4'-di(N,N-p-n-butylphenyl m-benzylthiophenyl)aminostilbene (16). To a solution of tris(dibenzylideneacetone) dipalladium ($Pd_2(dba)_3$) (0.165 g, 0.180 mmol) and bis-(diphenylphosphino)ferrocene (DPPF) (0.131 g, 0.236 mmol) in dry toluene (10 ml) under nitrogen atmosphere was added 3-bromophenyl benzyl sulfide (1.5 g, 5.38 mmol) at room temperature, and the resultant mixture was stirred for 10 min., sodium tert-butoxide (1.18 g), and trans-4,4'-di-p-n-butylphenyl aminostilbene (12) (1.274 g, 2.69 mmol) were added to this solution and stirred at 90° C. overnight. The reaction mixture was poured into water (20 ml), extracted three times with ether (20 ml) and dried over anhydrous magnesium sulfate. The yellow product was purified by flash column chromatography twice using 3% ethyl acetate in hexane as eluant and isolated in 41.2% (0.96 g) yield. $^1H$ NMR ($CDCl_3$, 500 MH) δ ppm: 6.8-7.4 (m, 34 Ar—H, 2 =CH), 4.04 (s, 4H, $CH_2$), 2.57 (t, J=7.7 Hz, $CH_2$, 4H), 1.60 (m, $CH_2$, 4H), 1.38 (m, $CH_2$, 4H), 0.94 (t, J=7.5 Hz, $CH_3$, 6H) $^{13}C$ NMR ($CDCl_3$, 125.7 MHz) δ ppm: 148.1, 146.8, 144.6, 138.3, 137.4, 137.2, 131.8, 129.4, 129.3, 128.7, 128.4, 127.1, 127.0, 126.5, 125.0, 124.1, 123.5, 123.3, 121.4, 38.7, 35.1, 33.6, 22.4, 14.0.

Example 16

Preparation of {3-[[4-(2-{4-[[3-(dimethylsulfonio)phenyl](phenyl)amino]-phenyl}-vinyl)phenyl](phenyl)amino]phenyl}(dimethyl)sulfonium triflate (17). Trans-4,4'-di(N,N-phenyl m-methyllthiophenyl)aminostilbene (13) (0.2 g, 0.344 mmol) was dissolved in 10 ml of dry methylene chloride and cooled at −78° C. in dry ice-acetone bath. To this solution was added, via syringe, methyl trifluoromethanesulfonate (96.55 µl, 0.852 mmol) and the mixture was stirred for 30 min while the temperature was maintained at −78° C. The resultant mixture was stirred overnight at room temperature and then poured into 10 ml of ether. The product was precipitated as a yellow solid, that was washed three times with ether and isolated in 95.8% (0.30 g) yield. $^1H$ NMR (DMSO, 500 MHz) δ ppm: 7.0-7.8 (m, 26H, Ar—H), 7.17 (s, =CH, 2H), 3.40 (s, $CH_3$, 12H)

Anal. Calcd. for $C_{44}H_{40}N_2S_4$: C, 56.52; H, 4.31; N, 3.00. Found: C, 55.92; H, 4.36; N, 2.86.

Example 17

Preparation of trans-benzyl{3-[[4-(2-{4-[[3-[benzyl(methyl)sulfonio)]phenyl](phenyl)amino]phenyl}vinyl)phenyl](phenyl)amino]phenyl}(methyl)sulfonium triflate (18). Trans-4,4'-di(N,N-phenyl-3-benzylthiophenyl)aminostilbene (14) (0.25 g, 0.329 mmol) was dissolved in 10 ml of dry methylene chloride and cooled at −78° C. in dry ice-acetone bath. To this solution was added, via syringe, methyl trifluoromethanesulfonate (82.7 µl, 0.731 mmol) and the mixture was stirred for 30 min while the temperature was maintained at −78° C. The resultant mixture was then stirred overnight at room temperature and poured into 10 ml of ether. The product was precipitated as a yellow solid, that was washed three times with ether and isolated in 83.8% (0.31 g) yield. $^1$H NMR (CD$_3$COCD$_3$, 500 MHz) δ ppm: 6.9-7.8 (m, 38H, 36 Ar—H, 2 =CH), 5.29 (d, $^2$J=12.5 Hz, 2H, SCH$_2$), 5.03 (d, $^2$J=12.5 Hz, 2H, SCH$_2$), 3.29 (s, 6H, CH$_3$)$^{13}$C NMR (CD$_3$COCD$_3$, 125.7 MHz) δ ppm: 149.2, 146.1, 145.6, 133.7, 131.9, 130.7, 130.0, 129.9, 129.3, 128.0, 127.8, 127.2, 127.0, 125.3, 124.9, 124.9, 123.9, 122.3, 51.0, 24.5 (1 aryl carbon and 1 CF$_3$ carbon were not observed).

Example 18

[3-((4-butylphenyl){4-[2-(4-{(4-butylphenyl)[3-(dimethylsulfonio)phenyl]-amino}phenyl)vinyl]phenyl}amino)phenyl](dimethyl)sulfonium triflate (19). Trans-4,4'-di[(4-n-butylphenyl)(3-methylthiophenyl)amino]stilbene (15) (0.34 g, 0.47 mmol) was dissolved in 10 ml of dry methylene chloride and cooled at −78° C. in dry ice-acetone bath. To this solution was added, via syringe, methyl trifluoromethanesulfonate (96.55 μl, 0.852 mmol) and the mixture was stirred for 30 min while the temperature was maintained at −78° C. The resultant mixture was then stirred two days at room temperature. After removal of some solvent under reduced pressure, the mixture was then poured into 20 ml of ether. The product was precipitated as a yellow solid, that was washed three times with ether and isolated in 75.5% (0.37 g) yield. $^1$H NMR (CD$_3$COCD$_3$, 500 MHz) δ ppm: 7.1-7.4 (mn, 24 Ar—H, 2 =CH), 3.05 (s, 6H, CH$_3$,) 2.72 (t, J=7.7 Hz, CH$_2$, 4H), 2.), 1.70 (m, CH$_2$, 4H), 1.46 (m, CH$_2$, 4H), 1.04 (t, J=7.3 Hz, CH$_3$, 6H).

Example 19

Preparation of trans-[3-((4-butylphenyl){4-[2-(4-{(4-butylphenyl)[3-((benzyl) methylsulfonio)phenyl] amino}phenyl)vinyl]phenyl}amino)phenyl]((benzyl)methyl)sulfonium triflate (20). Trans-4,4'-di[(4-n-butylphenyl)(3-benzylthiophenyl)amino]stilbene (16) (0.96 g, 1.103 mmol) was dissolved in 20 ml of dry methylene chloride and cooled at −78° C. in dry ice-acetone bath. To this solution was added, via syringe, methyl trifluoromethanesulfonate (276 μl, 2.437 mmol) and the mixture stirred for 30 min while the temperature was maintained at −78° C. The resultant mixture was then stirred two days at room temperature. After removal of some solvent under reduced pressure, the mixture was then poured into 20 ml of ether. The product was precipitated as a yellow solid, that was washed three times with ether and isolated in 80.9% (1.07 g) yield. $^1$H NMR (CD$_3$COCD$_3$, 500 MHz) δ ppm: 6.9-7.8 (m, 34 Ar—H, 2 =CH), 5.27 (d, $^2$J=12.5 Hz, 2H, SCH$_2$), 5.02 (d, $^2$J=12.5 Hz, 2H, SCH$_2$), 3.53 (s, 6H, CH$_3$), 2.63 (t, J=7.7 Hz, CH$_2$, 4H), 1.61 (m, CH$_2$, 4H), 1.36 (m, CH$_2$, 4H), 0.95 (t, J=7.2 Hz, CH$_3$, 6H)$^{13}$C NMR (CD$_3$COCD$_3$, 125.7 MHz) δppm: 149.4, 145.6, 143.6, 139.9, 133.5, 131.8, 130.7, 130.1, 129.8, 129.3, 127.9, 127.7, 127.1, 126.5, 125.7, 124.5, 123.8, 123.4, 121.7, 51.0, 34.7, 33.5, 24.5, 22.1, 13.3. (One CF$_3$ carbon was not observed).

Example 20

Preparation of {3-[[4-(2-{4-[[3-(dimethylsulfonio)phenyl](phenyl)amino]phenyl}vinyl)phenyl](phenyl)amino]phenyl}(dimethyl)sulfonium hexafluoro-antimonate (21). trans-{3-[[4-(2-{4-[[3-(dimethylsulfonio)phenyl](phenyl) amino]phenyl}vinyl)phenyl](phenyl)amino]phenl}(dimethyl)sulfonium triflate (17) (0.3 g 0.33 mmol) was dissolved in methylene chloride (5 ml) and acetone (10 ml). To this solution was added 10 ml aqueous sodium hexafluoroantimonate solution (0.341 g, 1.32 mmol). The resultant mixture was stirred three days in the dark at room temperature; with slow evaporation of methylene chloride and acetone, a yellow solid was formed and collected by filtration. The yellow solid was washed four times with water and three times with ether. NMR-pure product was obtained without further purification in 75.4% (0.31 g) yield. $^1$H NMR (DMSO, 500 MHz) δ ppm: 7.0-7.6 (m, 26H, Ar—H), 7.16 (s, =CH, 2H), 3.35 (s, CH3, 12H) Anal. calcd for C$_{44}$H$_{40}$N$_2$S$_2$Sb$_2$F$_{12}$: C, 45.51; H, 3.64; N, 2.53; S, 5.78.

Found: C, 45.75; H, 3.70; N, 2.77; S, 5.94.

Example 21

Preparation of trans-benzyl{3-[[4-(2-{4-[[3-[benzyl(methyl)sulfonio)]phenyl](phenyl)amino]-phenyl}-vinyl)phenyl](phenyl)amino]phenyl}(methyl)sulfonium hexafluoroantimonate (22). trans-benzyl{3-[[4-(2-{4-[[3-[benzyl (methyl)sulfonio)]phenyl](phenyl)amino]-phenyl}-vinyl) phenyl](phenyl)amino]phenyl}(methyl)sulfonium triflate (18) (0.69 g, 0.74 mmol) was dissolved in acetone (10 ml). To this solution was added an aqueous solution of sodium hexafluoroantimonate (0.76 g, 2.95 mmol). The resultant mixture was stirred overnight in the dark at room temperature; with slow evaporation of acetone, a yellow oil was formed. The yellow oil was allowed to cool at 0° C. to become a yellow solid. The yellow solid was collected by filtration and washed four times with water and three times with ether. A NMR-pure product was obtained without further purification and in 77.4% (0.72 g) yield. $^1$H NMR (CD$_3$COCD$_3$, 500 MHz) δ ppm: 6.9-7.6 (m, 38H, 36 Ar—H, 2 =CH), 5.26 (d, $^2$J=13.0 Hz, 2H, SCH$_2$), 5.02 (d, $^2$J=13.0 Hz, 2H, SCH$_2$), 3.54 (s, 6H, CH$_3$)$^{13}$C NMR (CD$_3$COCD$_3$, 125.7 MHz) δ ppm: 149.3, 146.1, 145.6, 133.7, 131.9, 130.7, 130.1, 129.9, 129.3, 127.9, 127.8, 127.2, 127.1, 125.3, 124.9, 124.8, 123.8, 122.2, 51.1,24.5 (One carbon was not observed).

Example 22

Preparation of [3-((4-butylphenyl){4-[2-(4-{(4-butylphenyl)[3-(dimethyl-sulfonio)phenyl]amino}phenyl)vinyl] phenyl}amino)phenyl](dimethyl)sulfonium hexafluoroantimonate (23). Trans-[3-((4-butylphenyl){4-[2-(4- {(4-butylphenyl)[3-(dimethylsulfonio)phenyl]amino}phenyl) vinyl]phenyl}amino)phenyl](dimethyl)sulfonium triflate (19) (0.87 g, 0.83 mmol) was dissolved in acetone (20 ml). To this solution was added 20 ml of an aqueous solution of sodium hexafluoroantimonate (0.88 g, 3.40 mmol). The resultant mixture was stirred two days in the dark at room temperature; with slow evaporation of acetone, a yellow solid was formed and collected by filtration. The yellow solid was washed four times with water and three times with ether. A NMR-pure product was obtained without further purification and isolated in 93.8% (0.95 g) yield. $^1$H NMR (CD$_3$COCD$_3$, 500 MHz) δ ppm: 7.1-7.4 (m, 24 Ar—H, 2 =CH), 3.06 (s, 6H, CH$_3$,) 2.72 (t, J=7.7 Hz, CH$_2$, 4H), 1.71 (m, CH$_2$, 4H), 1.46 (m, CH$_2$, 4H), 1.04 (t, J=7.3 Hz, CH$_3$, 6H)

Anal. calcd for C$_{50}$H$_{56}$N$_2$S$_2$Sb$_2$F$_{12}$: C, 49.20; H, 4.62; N, 2.29. Found: C, 49.0; H, 4.57; N, 2.14.

Example 23

Preparation of trans-[3-((4-butylphenyl){4-[2-(4-{(4-butylphenyl)[3-((benzyl)methylsulfonio)phenyl]

amino}phenyl)vinyl]phenyl}amino)phenyl]((benzyl)methyl)sulfonium hexafluoroantimonate (24). trans-[3-((4-butylphenyl){4-[2-(4-{(4-butylphenyl)[3-((benzyl)methylsulfonio)phenyl]amino}phenyl)vinyl]phenyl}amino)phenyl]((benzyl)methyl)sulfonium triflate (20) (0.85 g 0.81 mmol) was dissolved in acetone (10 ml). To this solution was added 10 ml of an aqueous solution of sodium hexafluoroantimonate (0.84 g, 3.25 mmol). The resultant mixture was stirred two days with slow evaporation of acetone in the dark at room temperature. The mixture was allowed to cool at 0° C., the yellow oil that formed solidified. The yellow solid was collected by filtration and washed four times with water and three times with ether. NMR-pure product was obtained without further purification in 83.2% yield (0.85 g). $^1$H NMR (CD$_3$COCD$_3$, 500 MHz) δ ppm: 6.9-7.7 (m, 36H, 34 Ar—H, 2 =CH), 5.27 (d, $^2$J=12.5 Hz, 2H, SCH$_2$), 5.02 (d, $^2$J=12.5 Hz, 2H, SCH$_2$), 3.52 (s, 6H, CH$_3$), 2.63 (t, J=7.7 Hz, CH$_2$, 4H), 1.61 (m, CH$_2$, 4H), 1.36 (m, CH$_2$, 4H), 0.95 (t, J=7.2 Hz, CH$_3$, 6H)$^{13}$C NMR (CD$_3$COCD$_3$, 125.7 MHz) δppm: 149.3, 145.6, 143.5, 139.9, 133.5, 131.9, 130.7, 130.0, 129.8, 129.3, 127.9, 127.7, 127.1, 126.5, 125.6, 124.5, 123.8, 123.4, 121.7, 51.0, 34.7, 33.5, 24.5, 22.1, 13.3.

Example 24

Preparation of tetraethyl p-xylylenebisphosphonate (25) (Piechucki, C. Synthesis, 1976, 187). A mixture of α,α'-dichloro-p-xylene (20 g, 0.114 mol) and triethyl phosphite (60 ml) was refluxed at 180° C. overnight. 80 ml of hexanes was added, and white crystals were formed immediately. Then the mixture was cooled at 0° C., and the product was collected, washed three times with 40 ml of hexanes and isolated in 94.4% (40.8 g) yield.

Example 25

Preparation of E,E-1,4-Bis(p-bromostyryl)benzene (26). 50% aqueous sodium hydroxide (20 ml) was added to a solution of tetraethyl p-xylylenebisphosphonate (2.40 g, 6.35 mmol) (25) and 4-bromobenzaldehyde (2.41 g, 13.02 mmol) in 10 ml of benzene. Tetra-n-butylammonium iodide (148 mmg) was added and the mixture was refluxed under nitrogen for 1 hour. The reaction mixture was allowed to cool and diluted by the addition of water (25 ml). A yellow solid was collected and washed three times with water, methanol and ether. The product was purified by recrystallization from xylenes and was isolated in 61.9% (1.73 g) yield (Product is insoluble in standard solvents).

Example 26

Preparation of E,E-1,4-Bis[p-(N-4'-n-butylphenyl)aminostyryl]benzene (27). To a solution of tris(dibenzylideneacetone) dipalladium (Pd$_2$(dba)$_3$) (0.17 g, 0.185 mmol) and bis(diphenylphospino)ferrocene (DPPF) (0.13 g, 0.235 mmol) was dissolved in 40 ml of toluene was added E,E-1,4-bis(p-bromostyryl)benzene (26) (4.06 g, 9.23 mmol) at room temperature under nitrogen, the resultant mixture was stirred for 10 minutes, and sodium tert-butoxide (4.80 g) and 4-butylaniline (2.76 g, 18.49 mmol) were added to this solution. The mixture was then stirred at 90° C. overnight. A yellow solid was collected, washed three times with methanol and ether, and was isolated in 71.8% (3.79 g) yield (Product is insoluble in standard solvents).

Example 27

Preparation of E,E-1,4-Bis{p-[N-(4-n-butylphenyl)-N-(3-methylthiophenyl)]aminostyryl}benzene (28). To a solution of tris(dibenzylideneacetone) dipalladium (Pd$_2$(dba)$_3$) (0.068 g, 0.074 mmol) and bis(diphenylphospino)ferrocene (DPPF) (0.049 g, 0.088 mmol) in 20 ml of toluene was added 3-bromothioanisole (1.50 g, 7.39 mmol) at room temperature under nitrogen, the resultant mixture was stirred for 10 minutes, sodium tert-butoxide (1.95 g) and E,E-1,4-Bis[p-(N-p-butylphenyl)aminostyryl]benzene (27) (2.11 g, 3.69 mmol) were added to this solution which was then stirred for 20 h at 90° C. The mixture was allowed to cool, poured into 20 ml of water and extracted three times with ether (60 ml×3). The combined organic layer was dried over anhydrous magnesium sulfate. After removal of solvent under reduced pressure, the product was purified by flash column chromatography using 5% of ethyl acetate in hexanes as eluant. The product was further purified by recrystallization from the mixture solvent of ether and hexanes (1:5) and was isolated in 9.2% (0.28 g) yield. $^1$H NMR (CDCl$_3$, 500 MHz) δppm: 6.8-7.5 (m, 32 H, 28 ArH, 4 =CH), 2.59 (t, J=7.5 Hz, 4H, CH$_2$), 2.41 (s, 6H, SCH$_3$), 1.62 (m, 4H, CH$_2$), 1.39 (m, 4H, CH$_2$), 0.96 (t, J=7.0 Hz, 6H, CH$_3$)$^{13}$C NMR (CDCl$_3$, 125.7 MHz) δ ppm: 148.1, 147.2, 144.7, 139.3, 138.4, 136.6, 131.4, 129.4, 129.3, 127.8, 127.3, 126.6, 125.1, 123.3, 121.4, 120.5, 120.2, 35.1, 33.6, 22.4, 15.6, 14.0 (One carbon was not observed) HRMS (FAB) calcd. for C$_{56}$H$_{56}$N$_2$S$_2$ M$^+$820.3885; found 820.3917.

Example 28

Preparation of E,E-1,4-Bis{p-[N-(4-n-butylphenyl)-N-(3-benzylthiophenyl)]aminostyryl}benzene (29). To a solution of tris(dibenzylideneacetone) dipalladium (Pd$_2$(dba)$_3$) (0.039 g, 0.041 mmol) and bis(diphenylphospino)ferrocene (DPPF) (0.027 g, 0.049 mmol) in 10 ml of toluene was added 3-bromophenyl benzyl sulfide (1.13 g, 4.06 mmol) at room temperature under nitrogen, the resultant mixture was stirred for 10 minutes, sodium tert-butoxide (0.89 g) and E,E-1,4-Bis[p-(N-p-butylphenyl)aminostyryl]benzene (27) (1.16 g, 2.03 mmol) were added to this solution and then stirred for 20 h at 90° C. The mixture was allowed to cool, poured into 20 ml of water and extracted three times (30 ml×3) with ether. The combined organic layer was dried over anhydrous magnesium sulfate. After removal of solvent under reduced pressure, the product was purified by flash column chromatography using 6% of ethyl acetate in hexanes as eluant and was isolated in 16.2% (0.32 g) yield. $^1$H NMR (CDCl$_3$, 500 MHz) δ ppm: 6.8-7.7 (m, 42 H, 38 ArH, 4 =CH), 4.00 (s, 4H, SCH$_2$), 2.57 (t, J=7.5 Hz, 4H, CH$_2$), 1.60 (m, 4H, CH$_2$), 1.39 (m, 4H, CH$_2$), 0.98 (t, J=7.2 Hz, 6H, CH$_3$)$^{13}$C NMR (CDCl$_3$, 125.7 MHz) δppm: 148.0, 147.0, 144.5, 138.3, 137.3, 137.2, 136.6, 131.3, 129.4, 129.3, 128.7, 128.4, 127.8, 127.2, 127.0, 126.5, 125.0, 124.1, 123.3, 123.2, 121.5, 38.5, 35.0, 33.6, 22.4, 14.0 (One carbon was not observed) HRMS (FAB) Calcd. for C$_{68}$H$_{64}$N$_2$S$_2$ M$^+$972.4511, found 972.4519.

Example 29

Preparation of 3-methylthio-4'-butyl diphenyl amine (30). To a solution of tris(dibenzylideneacetone)dipalladium (Pd$_2$(dba)$_3$) (0.18 g, 0.196 mmol) and bis(diphenylphospino)ferrocene (DPPF) (0.13 g, 0.235 mmol) in 100 ml of dry toluene was added 3-bromothioanisole (4.0 g, 0.0197 mol) at room temperature under nitrogen, the resultant mixture was stirred for 10 minutes, sodium tert-butoxide (4.30 g) and 4-n-butylamine (3.10 g, 0.0201 mol) were added to this solution and stirred at 90° C. overnight. The mixture was poured into 100 ml of water and extracted three times with ether (100 ml×3). The combined organic layer was dried over magnesium sulfate. After removal of solvent, the product was purified by flash column chromatography using 10% of ethyl acetate in hexanes as eluant and was isolated in 78.4% (4.20 g) yield. $^1$H NMR (CDCl$_3$, 500 MHz) δppm: 7.13 (t, J=8.0 Hz, 1 H), 7.08 (d, J=8.0 Hz, 2 H), 7.00 (d, J=8.5 Hz, 2 H), 6.89 (s, 1H), 6.75 (m, 2H), 5.60 (s, 1H, NH), 2.56 (t, J=7.7 Hz, 2 H, CH$_2$), 2.43 (s, 3H, SCH$_3$), 1.58 (m, 2H, CH$_2$), 1.35 (m, 2H, CH$_2$), 0.93 (t, J=7.2 Hz, 3H, CH$_3$) GC-MS (relative intenstiy %): 271 (M+, 67.8), 228 (m-MeSPh-NH-PhCH$_2$$^+$, 100).

Example 30

Preparation of 3-benzylthio-4'-butyl diphenyl amine (31). To a solution of tris(dibenzylideneacetone)dipalladium (Pd$_2$(dba)$_3$) (0.14 g, 0.153 mmol) and bis(diphenylphospino)ferrocene (DPPF) (0.12 g, 0.217 mmol) in 100 ml of dry toluene was added 3-bromophenyl benzyl sulfide (4.06 g, 0.0150 mol) at room temperature under nitrogen, the resultant mixture was stirred for 10 minutes, sodium tert-butoxide (3.27 g) and 4-butylaniline (3.50 g, 0.0234 mol) were added to this solution and stirred at 90° C. under nitrogen for 20 hours. The mixture was then poured into 100 ml of water and extracted three times with ether (100 ml×3). The combined organic layer was dried over magnesium sulfate. After removal of solvent, the product was purified by flash column chromatography using 10% of ethyl acetate in hexanes as eluant and was isolated in 83.3% (4.33 g) yield. $^1$H NMR (CDCl$_3$, 500 MHz) δ ppm: 7.26 (m, 6H), 7.12 (t, J=8.0 Hz 1 H), 7.07 (d, J=8.0 Hz, 2H), 6.94 (d, J=8.5 Hz, 2 H), 6.82 (d, J=7.5 Hz, 1H), 6.79 (d, J=8.0 Hz 1H), 5.59 (s, 1H, NH), 4.04 (s, 2H, SCH$_2$), 2.58 (t, J=7.7 Hz, 2 H, CH$_2$), 1.59 (m, 2H, CH$_2$), 1.38 (m, 2H, CH$_2$), 0.96 (t, J=7.2 Hz, 3H, CH$_3$) GC-MS (relative intensity %): 347 (M$^+$, 100), 304 (m-PhCH$_2$SPh-NH-Ph-p-CH$_2$$^+$, 100).

Example 31

Preparation of 2-p-bromophenyl-1,3-dioxolanes (32) (Greene, T.; Wuts, P. G. Protective Groups in Organic Synthesis, 2$^{nd}$ Edition, John-Wiley &Sons, 1991, p 185). p-Toluenesulfonic acid (200 mg) was added to a mixture of 4-bromobenzaldhyde (20 g, 0.108 mol) and ethylene glycol (18 ml, 0.323 mol) in toluene (250 ml). The mixture was heated to reflux for 20 hours with removal of water from the reaction. Then the mixture was allowed to cool, washed three times by aqueous NaHCO$_3$ and dried over anhydrous Na$_2$SO$_4$. After removal of solvent, the product was recrystallized from pentane and was isolated in 85.7% (21.2 g) yield.

Example 32

Preparation of 3-methylthio-4'-butyl-4''-formyl triphenyl amine (35). To a solution of tris(dibenzylideneacetone)dipalladium (Pd$_2$(dba)$_3$) (0.14 g, 0.153 mmol) and bis(diphenylphospino)ferrocene (DPPF) (0.11 g, 0.198 mmol) in 60 ml of toluene was added 2-p-bromophenyl-1,3-dioxolane (32) (5.22 g, 0.0228 mol) at room temperature under nitrogen, the resultant mixture was stirred for 10 minutes, sodium tert-butoxide (3.34 g) and 3-methylthio-4'-butyldiphenlylamine (30) (4.12 g, 0.0152 mol) were and stired at 90° C. under nitrogen for 20 hours. The mixture was poured into 100 ml of water and extracted three times with ether (100 ml×3). The combined organic layer was dried over magnesium sulfate. After removal of solvent, the residue was dissolved in THF (70 ml), 2 M of aqueous HCl solution (30 ml) was added and the mixture was stirred for 1 hour. Then 1 M aqueous sodium hydroxide solution (70 ml) was added and the mixture was extracted three times with ether (120 ml×3). The combined organic layer was dried over magnesium sulfate. After removal of the solvent, the product was purified by flash column chromatography using 10% of ethyl acetate in hexanes and was isolated in 78.8% (4.41 g) yield. $^1$H NMR (CDCl$_3$, 500 MHz) δ ppm: 7.67 (d, J=8.5 Hz, 2H), 7.23 (t, J=8.0 Hz, 1 H), 7.15 (d, J=8.0 Hz, 2 H), 7.07 (d, J=8.5 Hz, 2 H), 7.01-7.06 (m, 2H), 7.0 (d, J=9.0 Hz 2H), 6.91 (d, J=8.0 Hz, 1H), 2.60 (t, J=7.7 Hz, 2 H, CH$_2$), 2.42 (s, 3H, SCH$_3$), 1.61 (m, 2H, CH$_2$), 1.38 (m, 2H, CH$_2$), 0.94 (t, J=7.2 Hz, 3H, CH$_3$) $^{13}$C NMR (CDCl$_3$, 125.7 MHz) δ ppm: 190.4, 153.3, 146.6, 143.2, 140.3, 140.1, 131.3, 129.9, 129.7, 128.9, 126.4, 123.5, 122.5, 122.4, 119.1, 35.1, 33.5, 22.4, 15.5, 14.0GC-MS (relative intenstiy %): 375 (M$^+$, 90.3), 332 (m-MeSPh-N-p-PhCHO)-p-PhCH$_2$$^+$, 100)

Anal. Calcd. for C$_{24}$H$_{25}$ NOS: C, 76.76; H, 6.71; N, 3.73. Found: C, 77.04; H, 6.56; N, 3.85.

Example 33

Preparation of 3-benzylthio-4'-butyl-4''-formyl triphenyl amine (36). To a solution of tris(dibenzylideneacetone)dipalladium (Pd$_2$(dba)$_3$) (0.14 g, 0.153 mmol) and bis(diphenylphospino)ferrocene (DPPF) (0.11 g, 0.198 mmol) in 50 ml of toluene was added 2-p-bromophenyl-1,3-dioxolane (32) (5.22 g, 0.0228 mol) at room temperature under nitrogen, the resultant mixture was stirred for 10 minutes, sodium tert-butoxide (2.80 g) and 3-benzylthio-4'-butyldiphenlylamine (31) (4.33 g, 0.0125 mol) were added and the mixture was stirred at 90° C. under nitrogen for 20 hours. Then the mixture was poured into 100 ml of water and extracted three times with ether (100 ml×3). The combined organic layers were dried over magnesium sulfate. After removal of solvent, the residue was dissolved in THF (60 ml), 2 M of aqueous HCl solution (30 ml) was then added and the mixture was stirred for 1 hour. 1 M of aqueous sodium hydroxide solution (70 ml) was added and the mixture was extracted three times with ether (120 ml×3). The combined organic layers were dried over magnesium sulfate. After removal the solvent, the product was purified by flash column chromatography using 10% of ethyl acetate in hexanes and was isolated in 73.8% (4.16 g) yield. $^1$H NMR (CDCl$_3$, 500 MHz) δ ppm: 7.65 (d, J=9.0 Hz, 2H), 7.18-7.30 (m, 6H), 7.15 (d, J=8.5 Hz, 2H), 7.09 (d, J=7.5 Hz, 2 H), 7.03 (d, J=8.5 Hz, 2H), 7.0 (d, J=9.0 Hz 2H), 6.95 (d, J=8.5 Hz, 1H), 6.92 (d, J=8.5 Hz, 2H), 4.04 (s, 2H, SCH$_2$), 2.62 (t, J=7.7 Hz, 2 H, CH$_2$), 1.62 (m, 2H, CH$_2$), 1.40 (m, 2H, CH$_2$), 0.96 (t, J=7.2 Hz, 3H, CH$_3$) $^{13}$C NMR (CDCl$_3$, 125.7 MHz) δ ppm: 190.4, 153.2, 146.6, 143.2, 140.3, 137.8, 137.0, 131.3, 129.9, 129.7, 128.9, 128.7, 128.5, 127.2, 126.6, 126.4, 125.7, 123.6, 119.1, 38.6, 35.1, 33.5, 22.4, 14.0GC-MS (relative intenstiy %): 451 (M$^+$, 100), 408 (m-PhCH$_2$SPh-N-p-PhCHO)-p-PhCH$_2$$^+$, 50)

Anal. Calcd. for C$_{30}$H$_{29}$ NOS: C, 79.78; H, 6.47; N, 3.10. Found: C, 79.95; H, 6.61; N, 3.28.

Example 34

Preparation of E,E-1,4-Bis[4'-(N-p-$^n$butylphenyl-N-m-methylthiophenyl)aminostyryl]benzene (37). To a solution of 3-methylthio-4'-butyl-4''-formyl triphenyl amine (35) (2.0 g, 5.33. mmol) and tetraethyl α,α'-p-xylenebisphosphonate (25) (0.98 g, 2.59 mmol) in dry THF (30 ml) at 0° C. was added 6.0 ml of 1 M solution of KO$^t$Bu in THF. After 2 hours the reaction was quenched by addition of 30 ml of water, a large amount of yellow precipitate was formed. After removal THF under reduced pressure, the yellow solid was collected by filtration. The product was purified by flash chromatography using ethyl acetate/methylene chloride/hexanes (1:10:10) as eluant and was isolated in 95.0% (2.08 g) yield. $^1$H NMR (CDCl$_3$, 500 MHz) δ ppm: 6.8-7.5 (m, 32 H, 28 ArH, 4 =CH), 2.59 (t, J=7.5 Hz, 4H, CH$_2$), 2.41 (s, 6H, SCH$_3$), 1.62 (m, 4H, CH$_2$), 1.39 (m, 4H, CH$_2$), 0.96 (t, J=7.0 Hz, 6H, CH$_3$) $^{13}$C NMR (CDCl$_3$, 125.7 MHz) δ ppm: 148.1, 147.2, 144.7, 139.3, 138.4, 136.6, 131.4, 129.4, 129.3, 127.8, 127.3, 126.6, 125.1, 123.3, 121.4, 120.5, 120.2, 35.1, 33.6, 22.4, 15.6, 14.0 (One carbon was not observed)

HRMS (FAB) calcd. for C$_{56}$H$_{56}$N$_2$S$_2$M$^+$820.3885; found 820.3917

Anal. Calcd. for C$_{56}$H$_{56}$ N$_2$S$_2$: C, 81.91; H, 6.87; N, 3.41. Found: C, 81.98; H, 7.10; N, 3.54.

Example 35

Preparation of E,E-1,4-Bis[4'-p-$^n$butylphenyl-N-m-benzylthiophenyl)aminostyryl]benzene (38). To a solution of 3-methylthio-4'-butyl-4"-formyl triphenyl amine (36) (2.0 g, 4.43 mmol) and tetraethyl α,α'-p-xylenebisphosphonate (25) (0.82 g, 2.17 mmol) in dry THF (30 ml) at 0° C. was added 5.0 ml of 1 M solution of KO$^t$Bu in THF. After 2 hour the reaction was quenched by addition of 30 ml of water, then 25 ml of saturated brine was added and the mixture was extracted three times with methylene chloride/ether (1:4) (3×100 ml). The combined organic layer was dried over magnesium sulfate. After removal of solvent, the product was purified by flash column chromatography using 10% of ethyl acetate in hexanes as eluant and was isolated in 94.7% (2.21 g) yield. $^1$H NMR (CDCl$_3$, 500 MHz) δ ppm: 6.8-7.7 (m, 42 H, 38 Ar—H, 4 =CH), 4.00 (s, 4H, SCH$_2$), 2.57 (t, J=7.5 Hz, 4H, CH2), 1.60 (m, 4H, CH$_2$), 1.39 (m, 4H, CH$_2$), 0.98 (t, J=7.2 Hz, 6H, CH$_3$) $^{13}$C NMR (CDCl$_3$, 125.7 MHz) δ ppm: 148.0, 147.0, 144.5, 138.3, 137.3, 137.2, 136.6, 131.3, 129.4, 129.3, 128.7, 128.4, 127.8, 127.2, 127.0, 126.5, 125.0, 124.1, 123.3, 123.2, 121.5, 38.5, 35.0, 33.6, 22.4, 14.0 (One carbon was not observed.

HRMS (FAB) calcd. for C$_{68}$H$_{64}$N$_2$S$_2$ M$^+$972.4511; found 972.4519

Anal. Calcd. for C$_{68}$H$_{64}$ N$_2$S$_2$: C, 84.08; H, 7.43; N, 2.58. Found: C, 83.80; H, 7.66; N, 2.77.

Example 36

Preparation of E;E-(3-{(4-butylphenyl)[4-(2-{4-12-(4-{(4-butylphenyl)[3-(dimethylsulfonio)phenyl]amino}phenyl) vinyl]phenyl}vinyl)phenyl]amino}phenyl)(dimethyl)sulfonium (41). E,E-1,4-Bis{p-[N-(4-n-butylphenyl)-N-(3-methylthiophenyl)]aminostyryl}benzene (37) (0.27 g, 0.33 mmol) was dissolved in 10 ml of dry methylene chloride and cooled at −78° C. To this solution was added via syringe methyl trifluoromethanesulfonate (82.7 µl, 0.73 mmol) and stirred for 30 min while the temperature was maintained at −78° C. Then the mixture was stirred for two hours at room temperature. The solvent was removed under reduced pressure, and metathesis of anion was performed without isolation of the product.

The residue was dissolved in acetone (10 ml) and 10 ml of NaSbF$_6$ (0.35 g, 1.35 mmol) aqueous solution was added. The mixture was stirred for 4 hours and acetone was removed under reduced pressure at room temperature. A yellow solid was collected by filtration. This anion-exchange procedure was repeated three times. The yellow solid was collected, washed four times with water, and then dissolved in small amount of acetone (∞1 ml). To this solution 20 ml of ether was added and a yellow precipitate was formed immediately. The yellow solid was washed three times with ether, dried under vacuum and was isolated in 62.2% (0.27 g) yield. $^1$H NMR (CD$_3$COCD$_3$, 500 MHz) δppm: 7.0-7.8 (m, 32 H, 28 ArH, 4 =CH), 3.44 (s, 12H, CH$_3$), 2.64 (t, J=7.5 Hz, 4H, CH$_2$), 1.62 (m, 4H, CH$_2$), 1.39 (m, 4H, CH$_2$), 0.94 (t, J=7.5 Hz, 6H, CH$_3$)

Anal. Calcd. for C$_{58}$H$_{62}$ N$_2$S$_2$F$_{12}$Sb$_2$: C, 52.67; H, 4.72; N, 2.12. Found: C, 52.43; H, 4.69; N, 2.08.

Example 37

Preparation of E,E-benzyl{3-[(4-{2-[4-(2-{4-[{3-[benzyl (methyl)sulfonio]phenyl}(4-butylphenyl)amino] phenyl}vinyl)phenyl]vinyl}phenyl)(4-butylphenyl)amino] phenyl}methylsulfonium hexafluoroantimonate (42). E,E-1,4-Bis{p-[N-(4-n-butylphenyl)-N-(3-benzylthio phenyl)] amino styryl}benzene (38) (0.59 g, 0.61 mmol) was dissolved in 10 ml of dry methylene chloride and cooled at −78° C. To this solution was added via syringe methyl trifluoromethanesulfonate (145 µl, 1.28 mmol). While maintaining that temperature, the mixture was stirred for 30 min. Then the mixture was stirred for two days at room temperature. The solvent was removed under reduced pressure and, metathesis of anion was performed without isolation of the product.

The residue was dissolved in acetone (10 ml) and 10 ml of NaSbF$_6$ (0.70 g, 2.70 mmol) aqueous solution was added. Then the mixture was stirred for 4 hours and acetone was removed under reduced pressure at room temperature. The yellow solid was collected by filtration. The above anion-exchange procedure was repeated three times. The yellow solid was collected, washed four times with water, and then dissolved in small amount of acetone (~1 ml). To this solution was added 20 ml of ether and a yellow precipitate was formed. The yellow solid was washed three times with ether, dried under vacuum and was isolated in 70.6% (0.63 g).

Example 38

Preparation of 4,4'-di-n-butyl-3"-methylthiotriphenylamine (44). To a solution of tris(dibenzylideneacetone)dipalladium (Pd$_2$(dba)$_3$) (0.11 g, 0.120 mmol) and bis(diphenylphospino)ferrocene (DPPF) (0.082 g, 0.147 mmol) in 20 ml of dry toluene was added 3-bromothioanisole (1) (2.5 g, 12.31 mmol) at room temperature under nitrogen, the resultant mixture was stirred for 10 minutes, sodium tert-butoxide (2.70 g) Bi-(4-n-butylphenyl)amine (43) (3.46 g, 10.31 mmol) were added to this solution and stirred for 20 h at 90° C. The mixture was allowed to cool, poured into 50 ml of water and extracted three times (60 ml×3) with ether. The combined organic layer was dried over anhydrous magnesium sulfate. After removal of solvent under reduced pressure, the product was purified by flash column chromatography using 10% of ethyl acetate in hexanes as eluant and was isolated in 94.9% (4.71 g) yield. $^1$H NMR (CDCl$_3$, 500 MHz) δppm: 6.7-7.2 (m, 12H, ArH), 2.57 (t, J=7.5 Hz, 2H, CH$_2$), 2.4 (s, 3H, SCH$_3$), 1.60 (m, 2H, CH$_2$), 1.39 (m, 2H, CH$_2$), 0.95 (t, J=8.0 Hz, 3H, CH$_3$)EIMS (relative intensity %): 403 (M$^+$, 100).

Example 39

Preparation of 4,4'-di-n-butyl-3"-benzylthiotriphenylamine (45). To a solution of tris(dibenzylideneacetone)dipalladium (Pd$_2$(dba)$_3$) (0.079 g, 0.086 mmol) and bis(diphenylphospino)ferrocene (DPPF) (0.064 g, 0.116 mmol) in 20 ml of dry toluene was added 3-bromophenyl benzyl sulfide (2) (3.0 g, 10.75 mmol) at room temperature under nitrogen, the resultant mixture was stirred for 10 minutes, sodium tert-butoxide (2.36 g) Bi-(4-n-butylphenyl)amine (2.42 g, 10.75 mmol) were added to this solution and stirred for 20 h at 90° C. The mixture was allowed to cool, poured into 50 ml of water and was extracted three times (60 ml×3) with ether. The combined organic layer was dried over anhydrous magnesium sulfate. After removal of solvent under reduced pressure, the product was purified by flash column chromatography using 8% of ethyl acetate in hexanes as eluant and was isolated in 66.4% (3.29 g) yield.

Example 40

Preparation of 4-[di-(p-"butylphenyl)amino]-2-methylthiobenzaldehyde (46). To a solution of 4,4'-di-n-butyl-3"-methylthiotriphenylamine (44) (4.59 g, 11.38 mmol) and DMF (40 ml) at 0° C. was added POCl$_3$ (1.90 g, 12.40 mmol) dropwise. The resulting mixture was stirred at 95-100° C. under nitrogen for 20 hours. The mixture was cooled, poured into 50 ml of ice water slowly, neutralized with 4 M aqueous NaOH and extracted three times (40 ml×3) with ether. The combined organic layer was washed with saturated brine and dried over magnesium sulfate. After removal of solvent, the product was purified by flash chromatography using 10% of ethyl acetate in hexanes as eluant and was isolated in 63.9% (3.14 g) yield. $^1$H NMR (CDCl$_3$, 500 MHz) δppm: 9.99 (s, 1H, CHO), 7.55 (d, J=8.5 Hz, 1 H), 7.16 (d, J=8.5 Hz, 4H), 6.98 (d, J=8.5 Hz, 4 H), 6.71 (s, br, 1H), 6.68 (d, br, J=8.5 Hz, 1 H), 2.60 (t, J=7.7 Hz, 4H, CH$_2$), 2.17 (s, 3H, CH$_3$), 1.61 (m, 4H, CH$_2$), 1.38 (m, 4H, CH$_2$), 0.94 (t, J=7.5 Hz, 6H, CH$_3$)$^{13}$C NMR (CDCl$_3$, 125.7 MHz) δppm: 189.2, 153.0, 144.6, 143.2, 1430.3, 135.1, 129.6, 126.4, 124.8, 114.0, 35.1, 33.5, 22.3, 14.9, 14.0 (One carbon was not observed)GC-MS (relative intensity %): 431 (M$^+$, 100)

Anal. Calcd. for C$_{28}$H$_{33}$ NOS: C, 77.91; H, 7.71; N, 3.25. Found: C, 77.91; H, 7.79; N, 3.45.

Example 41

Preparation of 4-[di-(p-"butylphenyl)amino]-2-benzylthiobenzaldehyde (47). To a solution of 4,4'-di-n-butyl-3"-benzyltriphenylamine (45) (3.42 g, 7.14 mmol) and DMF (25 ml) at 0° C. was added POCl$_3$ (1.20 g, 7.85 mmol) dropwise. The resulting mixture was stirred at 95-100° C. under nitrogen for 20 hours. The mixture was cooled, poured into 40 ml of ice water slowly, neutralized with 4 M aqueous NaOH and extracted three times (40 ml×3) with ether. The combined organic layer was washed with saturated brine and dried over magnesium sulfate. After removal of solvent, the product was purified by flash chromatography using 10% of ethyl acetate in hexanes as eluant and was isolated in 64.9% (2.35 g) yield. $^1$H NMR (CDCl$_3$, 500 MHz) δpp m: 10.01(s, 1H, CHO), 7.56 (d, J=8.5 Hz, 1 H), 7.21 (m, 3H), 7.16 (d, J=8.5 Hz, 4H), 7.09 (m, 2H), 7.03 (d, J=8.5 Hz, 4 H), 6.81 (s, br, 1H), 6.69 (d, br, J=8.5 Hz, 1 H), 3.88 (s, 2H, SCH$_2$), 2.61 (t, J=7.7 Hz, 4H, CH$_2$), 1.61 (m, 4H, CH$_2$), 1.38 (m, 4H, CH$_2$), 0.94 (t, J=7.5 Hz, 6H, CH$_3$)$^{13}$C NMR (CDCl$_3$, 125.7 MHz) δ ppm: 189.4, 152.9, 143.1, 142.8, 140.3, 136.4, 134.0, 129.6, 128.7, 128.5, 127.1, 126.5, 125.6, 116.6, 114.9, 37.6, 35.1, 33.5, 22.4, 14.0.

Example 42

Preparation of E,E-1,4-Bis[2'-methylthio-4'-(N,N-di-p-n-butylphenyl)aminostyryl]benzene (48). To a solution of of 4-(N,N-di-p-n-butylphenyl)amino-2-methylthio benzaldehyde (46) (1.50 g, 3.48 mmol) and tetraethyl α,α'-p-xylenebisphosphonate (25) (0.65 g, 1.72 mmol) in dry THF (20 ml) at 0° C. was added 5.0 ml of 1 M solution of KO$^t$Bu in THF. After 2 hours the reaction was quenched by addition of 25 ml of water, then 25 ml saturated brine was added and the mixture was extracted three times by methylene chloride/ether (1:4) (3×60 ml). The combined organic layer was dried over magnesium sulfate. After removal of solvent, the product was purified by flash chromatography using 9% of ethyl acetate in hexanes as eluant and was isolated in 87.5% (1.43 g) yield (including ~6% of E-Z and/or Z-Z isomers by NMR). The products were dissolved in toluene (30 ml) and a small iodine crystal was added to this solution. The solution was refluxed overnight. After removal of solvent, the product was purified by flash chromatography using 7% of ethyl acetate in hexanes as eluant. $^1$H NMR (CDCl$_3$, 500 MHz) δppm: 6.8-7.6 (m, 30H), 2.58 (t, J=7.5 Hz, 8H, CH$_2$), 2.28 (s, 6H, CH$_3$), 1.60 (m, 8H, CH$_2$), 1.38 (m, 8H, CH$_2$), 0.95 (t, J=7.0 Hz, 12H, CH3) 13C NMR (CDCl$_3$, 125.7 MHz) δppm: 148.0, 144.9, 138.0, 137.6,36.9, 129.6, 129.2, 128.0, 126.7, 126.2, 125.1, 124.7, 120.6, 119.8, 35.0, 33.6,22.4, 16.6, 14.0HRMS (FAB): calcd, for C64H72N2S2 932.5137, found 932.5156

Anal. Calcd. for C64H72 N2S2: C, 82.35; H, 7.77; N, 3.0. Found: C, 81.90; H, 7.93; N, 3.55.

Example 43

Preparation of E,E-1,4-Bis[2'-benzylthio-4'-(N,N-di-p-n-butylphenyl)amino-styryl]benzene (49). To a solution of of 4-(N,N-di-p-n-butylphenyl)amino-2-benzylthio benzaldehyde (47) (1.80 g, 3.55 mmol) and tetraethyl α,α'-p-ylenebisphosphonate (25) (0.66 g, 1.74 mmol) in dry THF (20 ml) at 0° C. was added 5.0 ml of 1 M solution of KOtBu in THF. After 2 hours the reaction was quenched by addition of 25 ml of water, then 25 ml of saturated brine was added, and the mixture was extracted three times with methylene chloride/ether (1:4) (3×60 ml). The combined organic layer was dried over magnesium sulfate. After removal of solvent, the product was purified by flash chromatography using 10% of ethyl acetate in hexanes as eluant and was isolated in 95.4% (1.80 g) yield (including ~10% of E-Z and/or Z-Z isomers by NMR). The products were dissolved in toluene (30 ml), a small iodine crystal was added and the solution was refluxed overnight. After removal of solvent, the product was purified by flash chromatography using 7% of ethyl acetate in hexanes as eluant. 1H NMR (CDCl3, 500 MHz) δppm: 6.8-7.7 (m, 40H), 3.90 (s, 4H, SCH2), 2.58 (t, J=8.0 Hz, 8H, CH2), 1.60 (m, 8H, CH2), 1.38 (m, 8H, CH2), 0.94 (t, J=7.0 Hz, 12H, CH$_3$)$^{13}$C NMR (CDCl$_3$, 125.7 MHz) δppm: 147.7, 144.8, 137.9, 137.4, 136.9, 135.1, 131.5, 129.2, 128.8, 128.4, 127.9, 127.0, 126.8, 126.2, 125.7, 125.0, 124.6, 121.339.3, 35.1, 33.7, 22.4, 14.0HRMS (FAB): calcd, for C$_{76}$H$_{80}$N$_2$S$_2$ 1084.5763, found 1084.5797

Anal. Calcd. for C$_{76}$H$_{80}$ N$_2$S$_2$: C, 84.08; H, 7.43; N, 2.58. Found: C, 84.18; H, 7.66; N, 2.77.

Example 44

Preparation of {5-[bis(4-butylphenyl)amino]-2-[2-(4-{2-[4-[(3-butylphenyl)(4-butylphenyl)amino]-2-(dimethylsulfonio)phenyl]vinyl}phenyl)vinyl]phenyl}(dimethyl)sulfonium hexafluoroantimonate (52). E,E-1,4-Bis[2'-methylthio-4'-(N,N-di-p-"butylphenyl)amino styryl]benzene (48) (1.23 g, 1.32 mmol) was dissolved in 30 ml of dry methylene chloride and cooled at −78° C. To this solution was added via syringe methyl trifluoromethanesulfonate (310 μl, 2.74 mmol) and stirred for 30 min. while the temperature was maintained at −78° C. Then the mixture was stirred for two days at room temperature. The solvent was removed under reduced pressure and metathesis of anion was performed without isolation of the product.

The residue was dissolved in acetone (30 ml) and 20 ml of $NaSbF_6$ (0.35 g, 1.35 mmol) aqueous solution was added. Upon addition of $NaSbF_6$, a yellow precipitate was formed immediately. Then the mixture was stirred for 4 hours and acetone was removed under reduced pressure at room temperature. The yellow solid was collected by filtration. The above anion-exchange procedure was repeated three times. The yellow solid was collected, washed four times with water, and then dissolved in small amount of acetone (~2 ml). To this solution was added 30 ml of ether and a yellow precipitate was formed immediately. The yellow solid was washed three times with ether, dried under vacuum and was isolated in 78.7% (1.49 g) yield. $^1$H NMR (CDCl$_3$, 500 MHz) δppm: 7.1-8.0 (m, 30H), 3.40 (s, 12H, CH$_3$), 2.64 (t, J=7.5 Hz, 8H, CH$_2$), 1.62 (m, 8H, CH$_2$), 1.39 (m, 8H, CH$_2$), 0.95 (t, J=7.0 Hz, 12H, CH$_3$)

Anal. Calcd. for $C_{66}H_{78}N_2S_2F_{12}Sb_2$: C, 55.24; H, 5.48; N, 1.95. Found: C, 55.77; H, 5.31; N, 2.17.

Example 45

Preparation of benzyl{2-{2-[4-(2-{2-[benzyl(methyl)sulfonio]-4-[bis(4-butylphenyl)amino]phenyl}vinyl)phenyl]vinyl}-5-[(3-butylphenyl)(4-butylphenyl)amino]phenyl}methylsulfonium hexafluoroantimonate (53). E,E-1,4-Bis[2'-benzyl thio-4'-(N,N-di-p-n-butylphenyl)amino styryl]benzene (49) (1.47 g, 1.35 mmol) was dissolved in 25 ml of dry methylene chloride and cooled at −78° C. To this solution was added via syringe methyl trifluoromethanesulfonate (331 μl, 2.93 mmol). While maintaining that temperature, the mixture was stirred for 30 min. Then the mixture was stirred for two days at room temperature. The solvent was removed under reduced pressure and metathesis of anion was performed without isolation of the product. The residue was dissolved in 30 ml of acetone and 20 ml of $NaSbF_6$ (1.40 g, 5.40 mmol) aqueous solution was added. Then the mixture was stirred for 4 hours and acetone was removed under reduced pressure at room temperature. The yellow solid was collected by filtration. The above anion-exchange procedure was repeated three times. The yellow solid was collected, washed four times with water, and then dissolved in small amount of acetone (~2 ml). To this solution was added 20 ml of ether and a yellow oil was formed. The yellow oil was stirred and cooled at 0° C., and solidified. The yellow solid was washed three times with ether, dried under vacuum and was isolated in 74.9% (1.61 g) yield.

Example 46

Preparation of 1,4-n-butoxylbenzene (54) (Wright, M. E.; Mullick, S.; Lackritz, H. S.; Liu, L. -Y. Macromolecules, 1994, 27, 3009). A suspension of 1,4-hydroquinone (20 g, 0.182 mol) and 1-bromobutane (75 g, 0.547 mol) and potassium carbonate (75 g, 0.542 mol) in acetonitrile (400 ml) was heated to reflux for three days. The reaction mixture was allowed to cool to ambient temperature and poured into water (1000 ml). The precipitates were collected by filtration. The crude product was recrystallized twice from ethanol upon cooling at −78° C. to form white plate-like crystals in 98.0% (39.6 g) yield. $^1$H NMR (CDCl$_3$, 500 MHz) δppm: 6.82 (s, 4H, ArH), 3.91 (t, J=6.7 Hz, 4H, CH$_2$), 1.75 (m, 4H, CH$_2$), 1.49 (m, 4H, CH$_2$), 0.98 (t, J=7.2 Hz, 6H, CH$_3$). $^{13}$C NMR (CDCl$_3$, 125.7 MHz) δ ppm: 153.1, 115.3, 68.3, 31.4, 19.2, 13.9. GC-MS (relative intensity %): 222, (M$^+$, 43), 166 (Bu-n-Ph-OH$^+$, 21.4), 110 (HO-Ph-OH, 100).

Example 47

Preparation of 2,5-bis(bromomethyl)-1,4-bis(n-butoxyl)benzene (55). To a suspension of 1,4-bis(n-butoxyl)benzene (7.0 g, 0.0315 mol) and paraformadhyde (1.89 g) in acetic acid (230 ml) was added hydrobromic acid (23 ml) in one portion. The mixture was then heated to 65-70° C. with stirring for 3 h. Cooling to ambient temperature, the mixture was poured into water (700 ml), the crude product was collected and recrystallized from methanol and was isolated in 29.3% (3.76 g) yield. $^1$H NMR (CDCl$_3$, 500 MHz) δppm: 6.82 (s, 2H, ArH), 4.52 (s, 4H, CH$_2$), 4.0 (t, J=6.2 Hz, 4H, CH$_2$), 1.80 (m, 4H, CH$_2$), 1.53 (m, 4H, CH$_2$), 1.0 (t, J=7.5 Hz, 6H, CH$_3$) $^{13}$C NMR (CDCl$_3$, 125.7 MHz) δ ppm: 150.6, 127.4, 114.5, 68.6, 31.4, 28.8, 19.3, 13.9GC-MS (relative intensity %): 407, 408, 409 (M$^+$, 1:2:1).

Example 48

Preparation of 2,5-butoxyl-p-xylene bis(triphenylphosphino)dibromide (56). A solution of 2,5-bis(bromomethyl)-1,4-bis(n-butoxyl)benzene (55) (2.4 g, 5.88 mmol) and triphenylphosphine (4.0 g, 15.25 mmol) in toluene (80 ml) was heated to reflux for 3 hours. The mixture was cooled to ambient temperature, poured into hexane (200 ml) and a white precipitate was collected. The precipitate was dissolved in methylene chloride (10 ml) and reprecipitated in hexane to afford a NMR-pure compound in (4.67 g, 85.2%) yield. $^1$H NMR (CDCl$_3$, 500 MHz) δppm: 7.5-7.8 (m, 30H, Ar—H), 6.72 (s, 2H, ArH), 5.31 (d, J=13.0 Hz, 4H, CH$_2$), 3.01 (t, J=6.0 Hz, 4H, CH$_2$), 1.10 (m, 8H, CH$_2$), 0.79 (t, J=7.0 Hz, 6H, CH$_3$).

Example 49

Preparation of E,E-1,4-bis(p-methylthiostyryl)-2,5-bis(butoxyl)benzene (59). To a solution of 2,5-butoxyl-p-xylene bis(triphenyl)phosphino bromide (2.0 g, 2.14 mmol) and 4-methylbenzaldehyde (0.64 g, 4.20 mmol) in absolute ethanol (40 ml) was added a solution of sodium ethoxide (8.69 mmol) in 10 ml of absolute ethanol. The reaction mixture was refluxed for 15 hours. Upon cooling to ambient temperature 25 ml of water was added. The yellow precipitate was collected by filtration and washed three times with methanol. The isomers were purified by flash chromatography using hexanes/methylene chloride/ethyl acetate (50:40:10) as eluant. The isomers were dissolved in 30 ml of toluene and refluxed with a small crystal of iodine for 20 hours. The mixture was cooled to ambient temperature and brownish crystals were formed. The brownish crystals were refluxed with activated charcoal in 40 ml of toluene for 20 min and the resulting yellow crystals were collected after hot-filtration in 47.6% (0.53 g) yield. $^1$H NMR (CDCl$_3$, 500 MHz) δppm: 7.4-7.5 (m, 6H), 7.25 (d, 4H, J=8.5 Hz), 7.11 (s, 2H), 7.09 (d, J=16.0 Hz, 2H, =CH), 4.06 (t, J=6.5 Hz, 4H, CH$_2$), 2.05 (s, 6H, SCH$_3$), 1.86 (p, J=6.5 Hz, 4H, CH$_2$), 1.57 (m, 4H, CH$_2$), 1.03 (t, J=7.5 Hz, 6H, CH$_3$) $^{13}$C NMR (CDCl$_3$, 125.7 MHz) δ ppm: 151.0, 137.5, 134.9, 128.1, 126.9, 126.7, 126.6, 122.8, 110.4, 69.1, 31.5, 19.5, 19.4, 15.8, 14.0

Anal. Calcd. for $C_{32}H_{38}O_2S_2$: C, 74.09; H, 7.38;. Found: C, 74.12; H, 7.42.

Example 50

Preparation of tetraethyl 2,5-bis(butoxyl)-p-xylene phosphonate (58). 2,5-bis(bromomethyl)-1,4-bis(n-butoxyl)benzene (55) (2.0 g, 4.90 mmol) and triethyl phosphite (10 ml) was heated to reflux for 24 hours. After removal of unreacted triethyl phosphite under reduced pressure, 10 ml of hexanes was added to the residue. The mixture was stirred for 10 min and cooled at 0° C.; the solvent was then decanted. The product was washed three times in this way, dried in vacuo, and isolated in 39.2% (1.2 g) yield. $^1$H NMR (CDCl$_3$, 500 MHz) δppm: 6.91 (s, 2H, ArH), 4.02 (m, 8H, CH$_2$), 3.93 (t, J=6.0 Hz, 4H, CH$_2$), 3.22 (d, J=20.0 Hz, 4H, CH$_2$), 1.75 (m, 4H, CH$_2$), 1.48 (m, 4H, CH$_2$), 1.24 (t, J=7.0 Hz, 12H, CH$_3$), 0.97 (t, J=7.2 Hz, 6H, CH$_3$).

Example 51

Preparation of E,E-1,4-bis(p-methylthiostyryl)-2,5-bis (butoxyl)benzene (59). To a solution of 4-methylthiobenzaldehyde (0.65 g, 4.27 mmol) and tetraethyl 2,5-bis(butoxyl)-p-xylene phosphonate (1.0 g, 1.92 mmol) in 30 ml of dry THF was added 1M solution of KO$^t$Bu (5 ml, 5 mmol) at 0° C. The mixture was stirred at 0° C for 3 hours. The reaction was quenched by addition of water (30 ml). The yellow precipitate was collected by filtration and washed three times by methanol. The product was recrystallized from toluene and isolated in 68.1% (0.68 g) yield. $^1$H NMR (CDCl$_3$, 500 MHz) δppm: 7.4-7.5 (m, 6H), 7.25 (d, 4H, J=8.5 Hz), 7.11 (s, 2H), 7.09 (d, J=16.0 Hz, 2H, =CH), 4.06 (t, J=6.5 Hz, 4H, CH$_2$), 2.05 (s, 6H, SCH$_3$), 1.86 (p, J=6.5 Hz, 4H, CH$_2$), 1.57 (m, 4H, CH$_2$), 1.03 (t, J=7.5 Hz, 6H, CH$_3$)$^{13}$C NMR (CDCl$_3$, 125.7 MHz) δ ppm: 151.0, 137.5, 134.9, 128.1, 126.9, 126.7, 126.6, 122.8, 110.4, 69.1, 31.5, 19.5, 19.4, 15.8, 14.0.

Example 52

Preparation of E,E-{4-[2-(2,5-dibutoxy-4-{2-[4-(dimethylsulfonio)phenyl]vinyl}phenyl)vinyl]phenyl}(dimethyl) sulfonium triflate (60). To a solution of E,E-1,4-bis(p-methylthiostyryl)-2, 5-bis(butoxyl)benzene (59) (0.68 g, 1.31 mmol) was added methyl trifluorosulfonate (0.44 g, 0.303 ml) at −78° C. The mixture was stirred for 30 minutes, allowed to rise to ambient temperature and stirred overnight. The mixture was poured into 30 ml of ether; the resulting yellow solid was collected by filtration and was isolated in 1.06 g (95.5%) yield.

$^1$H NMR (500 MHz, DMSO) δ ppm: 8.06 (d, J=8.5 Hz, 4H), 7.86 (d, J=8.5 Hz, 4H), 7.63 (d, J=16.5 Hz, 2H, =CH), 7.51 (d, J=16.5 Hz, 2H, =CH), 7.39 (s, 2H), 4.12 (t, J=6.2 Hz, 4H, CH$_2$), 3.27 (s, 12 H, CH$_3$), 1.82 (m, 4H, CH$_2$), 1.53 (m, 4H, CH2), 0.99 (t, J=7.0 Hz, 6H, CH$_3$).

Example 53

Preparation of E,E-{4-[2-(2,5-dibutoxy-4-{2-[4-(dimethylsulfonio)phenyl]vinyl}phenyl)vinyl]phenyl}(dimethyl) sulfonium hexafluoroantimonate (61). Sodium hexafluoroantimonate (1.36 g, 5.26 mmol) in 20 ml of water was added to a solution of E,E-{4-[2-(2,5-dibutoxy-4-{2-[4-(dimethylsulfonio)phenyl]vinyl}phenyl)vinyl]phenyl}(dimethyl)sulfonium triflate (60) (1.06 g, 1.25 mmol) in 20 ml of acetone. The reaction mixture was stirred for 2 hours. The yellow solid was collected by filtration and the above procedure was repeated three times, and isolated in 1.14 g (89.4%) yield.

$^1$H NM (500 MHz, DMSO) δppm: 8.06 (d, J=8.5 Hz, 4H), 7.86 (d, J=8.5 Hz, 4H), 7.63 (d, J=16.5 Hz, 2H, =CH), 7.51 (d, J=16.5 Hz, 2H, =CH), 7.39 (s, 21), 4.12 (t, J=6.2 Hz, 4H, CH$_2$), 3.27 (s, 12 H, CH$_3$), 1.82 (m, 4H, CH$_2$), 1.53 (m, 4H, CH2), 0.99 (t, J=7.0 Hz, 6H, CH$_3$).

Example 54

Preparation of 4-bromophenyl n-butyl sulfide (62). 4-Bromobenzenethiol (5 g, 26.44 mmol) was added to a solution of sodium methoxide (1.43 g, 26.48 mmol) in 20 ml of anhydrous methanol. The mixture was stirred for 30 min under nitrogen at room temperature and a solution of methyl iodide (4.51 g, 31.77 mmol) in 20 ml anhydrous methanol was then added. The reaction mixture was stirred overnight at room temperature, poured into 2 M of NaOH aqueous solution (30 ml) and extracted three times with ether (3×100 ml ). The combined organic layer was washed with saturated sodium chloride solution and dried over anhydrous magnesium sulfate. After removal of solvent, the product was purified by distillation at 117-119° C. (0.5 mmHg) and was isolated in 88.4% (5.72 g) yield.

Example 55

Preparation of 4-butylthiobenzaldhyde (63). To a solution of 4-bromophenyl n-butyl sulfide (1.5 g, 6.12 mmol) in 60 ml of dry THF was added $^n$BuLi (4.1 ml, 1.6 M in hexanes) at −78° C. under nitrogen. The mixture was stirred for 1 hour at −78° C. and then DMF (2.0 ml) was added. The reaction mixture was stirred at room temperature for 2 hours. Then 40 ml of water was added to this mixture, the product was extracted three times by ether (3×50 ml) and the combined organic layer was dried over magnesium sulfate. After removal of solvent under reduced pressure, the product was purified by flash chromatography column using 10% of ethyl acetate in hexanes as eluant and isolated in 66.7% (0.88 g) yield.$^1$H NMR (CDCl$_3$, 500 MHz) δppm: 9.98 (s, 1H, CHO), 7.77 (d, J=8.5 Hz, 2H), 7.36 (d, J=8.5 Hz, 2H,), 7.11 (s, 2H), 3.02 (t, J=7.2 Hz, 2H, CH$_2$), 1.71 (m, 2H, CH$_2$), 1.50 (m, 2H, CH$_2$), 0.97 (t, J=7.5 Hz, 6H, CH$_3$).

Example 56

Preparation of E,E-1,4-bis(p-n-butylthiostyryl)benzene (64). To a solution of 4-n-butylthiobenzaldhyde (0.80 g, 4.12 mmol) and tetraethyl p-xylene phosphonate (0.78 g, 2.06 mmol) in 25 ml of dry THF was added a 1M solution of KO$^t$Bu (5 ml, 5 mmol) at 0° C. The mixture was stirred at 0° C. for 3 hours. The reaction was quenched by addition of water (30 ml). The yellow precipitate was collected by filtration and washed three times with methanol. The product was recrystallized from xylene and isolated in 61.5% (0.58 g) yield.

Example 57

Preparation of 1,4-dimethylthiobenzene (65) (Engman, L.; Hellberg, J. S. E. J. Organometallic Chem. 1985, 296, 357). tert-Butyl lithium (25 ml, 1.7 M) was added dropwise to a stirred solution of 1,4-dibromobenzene (5 g, 0.0212 mol) in 125 ml of THF under nitrogen at −78° C. After 30 min the temperature was allowed to rise to ambient and sulfur (1.36 g, 0.0425 mol) was added while a brisk stream of nitrogen was passed through the open system to exclude air. After sulfur was consumed, methyl iodide (6.5 g, 0.0458 mol) in 5 ml of THF was then added and the mixture was stirred for another 40 min. The solvent was removed under reduced pressure and 50 ml of water was added to the residue. The mixture was extracted three times with ether (3×100 ml) and the combined organic layer was dried over magnesium sulfate. After removal of the solvent, the product was purified by recrystallization from methanol and was isolated in 67.7% (2.44 g) yield as a white solid.GC-MS (relative intensity %): 170 (M$^+$, 100), 155 (MeSPh-S$^+$, 100).

Example 58

Preparation of 2,5-di(methylthio)-p-xylene (66) (Engman, L.; Hellberg, J. S. E. J. Organometallic Chem. 1985, 296, 357). tert-Butyl lithium (22.5 ml, 1.7 M) was added dropwise to a stirred solution of 2,5-dibromo-p-xylene (2.5 g, 9.47 mmol) in 60 ml of THF under nitrogen at −78° C. After 30 min the temperature was allowed to rise to ambient and sulfur (0.61 g, 0.019 mol) was added while a brisk stream of nitrogen was passed through the open system to exclude air. After sulfur was consumed, methyl iodide (2.7 g, 0.019 mol) in 2 ml of THF was then added and the mixture was stirred for another 40 min. The solvent was removed under reduced pressure and 50 ml of water was added to the residue. The mixture was extracted three times with ether (3×100 ml) and the combined organic layer was dried over magnesium sulfate. After removal of the solvent, the product was purified by recrystallization from methanol and isolated in 66.7% (1.25 g) yield as a white solid.$^1$H NMR (CDCl$_3$, 500 MHz) δppm: 6.98 (s, 2H, Ar—H), 2.44 (s, 6H, CH$_3$), 2.36 (s, 6H, CH$_3$). $^{13}$C NMR (CDCl$_3$, 125.7 MHz) δppm: 134.4, 133.7, 127.1, 19.6, 15.9.

Example 59

Preparation 4-n-butoxyl benzaldehyde (71). A suspension of 4-hydroxybenzaldehyde (5 g, 0.0409 mol), potassium carbonate (6.91 g, 0.05 mol) and 1-bromobutane (6.87 g, 0.05 mol) in 40 ml of acetonitrile was refluxed for two days. The mixture was allowed to cool to ambient temperature and 60 ml of water was added. The mixture was extracted three times with ether (3×120 ml) and the combined organic layer was dried over magnesium sulfate. After removal of the solvent, the product was purified by distillation under reduced pressure (0.4 mmHg) at 112° C. and isolated in 86.8% (6.32 g) yield as colorless oil.$^1$H NMR (CDCl3, 500 MHz) δ ppm: 9.84 (s, H, CHO), 7.83 (d, J=9.0 Hz, 2H), 6.99 (d, J=8.5 Hz, 2H), 4.05 (t, J=6.5 Hz, 2H), 1.80 (m, 2H), 1.51 (m, 2H), 0.99 (t, J=7.5 Hz, 3H). $^{13}$C NMR (CDCl3, 125.7 MHz) δ ppm: 134.4, 133.7, 127.1, 19.6, 15.9

MS (relative intensity %): 178 (M+, 33), 121 p-CHOPhO+, 100).

Example 60

Preparation of 2,5-dibromo-α,α'-dibromo-p-xylene (67). (Higuchi, H.; Kibayashi, E.; Sakata, Y.; Misumi, S. Tetrahedron 1986, 42, 173). N-bromosuccinimide (13.5 g, 0.075 mol) was added in four portions over 4 hours to a refluxing solution of 2,5-dibromo-p-xylene (10 g, 0.0379 mol) containing benzoyl peroxide (0.355 g). The mixture was refluxed for 2 hours and then allowed to cool to ambient temperature. After filtration, the solvent was removed under reduced pressure. The resulting yellowish solid was recrystallized from methanol to afford a 7.58 g (47.4%) yield of product.1H NMR (CDCl3, 500 MHz) δ ppm: 7.67 (s, 2H, Ar—H), 4.52 (s, 2H, CH2)13C NMR (CDCl3, 125.7 MHz) δ ppm: 138.9, 135.3, 123.3, 31.5EIMS (relative intensity %): 422 (M+, 18), 341 (o-Br-m-Br-p-BrCH2PhCH2+, 100), 262 (o-Br-m-Br-p-CH2-PhCH2$^+$, 91).

Example 61

Preparation of 2-bromo-α,α'-dibromo-p-xylene (68). N-bromosuccinimide (36.54 g, 0.216 mol) was added in five portions over 5 hours to a refluxing solution of 2-bromo-p-xylene (19 g, 0.103 mol) containing benzoyl peroxide (0.41 g). The mixture was refluxed for 2 hours and then allowed to cool to ambient temperature. After filtration, the solvent was removed under reduced pressure. The resulting yellowish solid was recrystallized from methanol to afford a 14.43 g (41.1%) yield of product.$^1$H NMR (CDCl$_3$, 500 MHz) δppm: 7.62 (d, $^4$J=2.0 Hz, 1H), 7.43 (d, $^3$J=8.0 Hz, 1H), 7.33 (dd, $^3$J=7.7 Hz, $^4$J=1.8 Hz), 4.60 (s, 2H, CH$_2$), 4.41(s, 2H, CH$_2$)$^{13}$C NMR (CDCl$_3$, 125.7 MHz) δppm: 139.9, 137.1, 133.7, 131.5, 124.5, 32.7, 31.3GC-MS (relative intensity %): 342 (M$^+$, 12), 264, 263,262 (1:2:1, m-Br-p-BrCH$_2$-PhCH$_2^+$, 100), 182, 184 (1:1, m-Br-p-CH2PhCH2$^+$, 70).

Example 62

Preparation of tetraethyl 2,5-dibromo-p-xylenebisphosphonate (69). The mixture of 2, 5-dibromo-α,α'-dibromo-p-xylene (67) (7.58 g, 0.018 mol) and triethyl phosphite (60 ml) was refluxed at 180° C. overnight. The excess triethyl phosphite was removed under reduced pressure, 60 ml of hexanes was added, and white solid was formed. The solid was collected by filtration, washed three times with 20 ml of hexanes and gave 7.93 g (82.2%) of product.$^1$H NMR (CDCl$_3$, 500 MHz) δppm: 7.62 (s, 2H, Ar—H), 4.06 (m, 8H, CH2), 3.32 (d, J=20.5 Hz, 4H, CH$_2$), 1.28 (t, J=7.0 Hz, 12H, CH$_3$)$^{13}$C NMR (CDCl$_3$, 125.7 MHz) δppm: 135.2, 132.5, 123.6, 62.35, 62.32, 33.4, 32.2, 16.31, 16.28GC-MS (relative intensity %): 491 (M$^+$, <5%).

Example 63

Preparation of tetraethyl 2-bromo-p-xylenebisphosphonate (70). The mixture of 2-bromo-α,α'-dibromo-p-xylene (68) (14.43 g, 0.042 mol) and triethyl phosphite (145 ml) was refluxed at 180° C. overnight. The excess triethyl phosphite was removed under reduced pressure, 60 ml of hexanes was added, the mixture was cooled at −78 ° C. and white solid was formed on vigorous stirring. The solid was collected by rapid filtration, washed three times with 20 ml of cool hexanes, dried in vacuo and isolated in 14.0 g (72.7%) yield as light yellow oil.$^1$H NMR (CDCl$_3$, 500 MHz) δppm: 7.51 (s, br, 1H), 7.40 (dd, $^3$J=7.7 Hz, $^4$J=2.2 Hz, 1H), 7.21 (d, $^3$J=8.0 Hz, 1H) 4.04 (m, 8H, CH2), 3.38 (d, J=21.5 Hz, 2H, CH$_2$), 3.09 (d, J=21.5 Hz, 2H, CH$_2$), 1.25 (m, 12H, CH$_3$).

Example 64

Preparation of 2,5-dibromo-E,E-1,4-bis[p-n-butoxystyryl] benzene (74). To a solution of p-butoxybenzaldehyde (71) (0.7 g, 3.95 mmol) and tetraethyl 2,5-dibromo-α,α'-p-xylenebisphosphonate (69) (1.02 g, 1.90 mmol) in dry THF (25 ml) at 0° C. was added 4 ml of 1 M solution of KO$^t$Bu in THF. After 2 hours the reaction was quenched by addition of 20 ml of methanol. A yellow solid was collected by filtration and washed three times with methanol to afford NMR-pure product in 0.92 g (82.9%) yield. $^1$H NMR (CDCl$_3$, 500 MHz) δppm: 7.83 (s, 2H), 7.48 (d, J=8.5 Hz, 4H), 7.22 (d, J=16.5 Hz, 2H, =CH), 7.01 (d, J=16.0 Hz, 2H, =CH), 6.91 (d, J=9.0 Hz, 4H), 4.0 (t, J=6.5 Hz, 4H, CH2), 1.80 (m, 4H, CH$_2$), 1.52 (m, 4H, CH2), 0.99 (t, J=7.2 Hz, 6H, CH$_3$)$^{13}$C NMR (CDCl$_3$, 125.7 MHz) δppm: 159.5, 137.2, 131.6, 129.9, 129.2, 128.2, 123.4, 122.8, 114.7, 67.7, 31.3, 19.2, 13.9.

Example 65

Preparation of 2-bromo-E,E-1,4-bis[p-n-butoxystyryl]benzene (75). To a solution of p-butoxybenzaldehyde (71) (2.0 g, 11.2 mmol) and tetraethyl 2-bromo-α,α'-p-xylenebisphosphonate (70) (2.55 g,. 5.5 mmol) in dry THF (70 ml) at 0° C. was added 12 ml of 1 M solution of KO$^t$Bu in THF. After 2 hours the reaction was quenched by addition of 70 ml of methanol. A light yellow solid was collected by filtration and washed three times with methanol to afford NMR-pure product in 2.36 g (84.5%) yield. $^1$H NMR (CDCl$_3$, 500 MHz) δppm: 7.70 (s, 1H), 7.62 (d, J=8.5 Hz, 1H), 7.47 (d, J=8.0 Hz, 2H), 7.44 (d, J=8.5 Hz, 2H), 7.4 (d, J=7.5 Hz, 1H), 7.32 (d, J=16.5 Hz, 1H, =CH), 7.06 (d, J=16.5 Hz, 1H, =C), 7.01 (d, J=16.0 Hz, 1H, =CH), 6.85-6.95 (m, 5H, 4 Ar—H, 1 =CH), 4.0 (m, 4H, CH$_2$), 1.80 (m, 4H, CH$_2$), 1.52 (m, 4H, CH2), 1.0 (t, J=7.5 Hz, 6H, CH$_3$)$^{13}$C NMR (CDCl$_3$, 125.7 MHz) δppm: 159.1, 138.1, 135.7, 130.5, 130.4, 129.7, 129.4, 129.2, 128.0, 127.8, 126.2, 125.2, 124.7, 124.5, 124.3, 114.7, 67.7, 31.3, 19.2, 13.9.

Example 66

Preparation of 2,5-dimethylthio-E,E-1,4-bis p-n-butoxystyryl]benzene (78). 1.7 M tert-butyl lithium (3.63 ml, 6.17 mmol) was added dropwise to a stirred solution of 2,5-dibromo-1,4-E,E-bis[4-(n-butoxy)styryl]benzene (74) (0.9 g, 1.54 mmol) in 20 ml of THF under nitrogen at −78° C. After 30 min the temperature was allowed to rise to ambient and sulfur (0.10 g, 3.08 mmol) was added while a brisk stream of nitrogen was passed through the open system to exclude air. After sulfur was consumed, methyl iodide (0.46 g, 3.24 mmol) in 0.5 ml of THF was added and the mixture was stirred for another 1 hour. The solvent was removed under reduced pressure and 20 ml of water was added to the residue. The mixture was stirred vigorously for 20 min and yellow solid was collected by filtration. The yellow product was purified by flash column chromatography using toluene/hexanes from 1:1 to 5:3 as eluant and isolated in 0.39 g (48.7%) yield.

$^1$H NMR (CDCl$_3$, 500 MHz) δppm: 7.54 (s, 2H), 7.49 (d, J=9.0 Hz, 4H), 7.42 (d, J=16.5 Hz, 2H, =CH), 7.01 (d, J=16.0 Hz, 2H, =CH), 6.91 (d, J=9.0 Hz, 4H), 4.0 (t, J=6.7 Hz, 4H, CH$_2$), 2.50 (s, 6H, CH$_3$), 1.79 (m, 4H, CH$_2$), 1.52 (m, 4H, CH$_2$), 0.99 (t, J=7.2 Hz, 6H, CH$_3$)

$^{13}$C NMR (CDCl$_3$, 125.7 MHz) δppm: 159.0, 137.0, 136.8, 135.9, 129.7, 128.4, 125.1, 123.1, 114.7, 67.7, 31.3, 19.2, 17.3, 13.9

Anal. Calcd. for $C_{32}H_{38}O_2S_2$: C, 74.09; H, 7.38;. Found: C, 73.93; H, 7.43.

Example 67

Preparation of 2-methylthio-E,E-1,4-bis[p-n-butoxystyryl]benzene (79). 1.7 M tert-butyl lithium (5.1 ml, 8.67 mmol) was added dropwise to a stirred solution of 2-bromo-1,4-E,E-bis[4-(n-butoxy)styryl]benzene (75) (2.3 g, 3.98 mmol) in 50 ml of THF under nitrogen at −78° C. After 30 min the mixture was allowed to rise to ambient temperature and sulfur (0.15 g, 4.69 mmol) was added while a brisk stream of nitrogen was passed through the open system to exclude air. After sulfur was consumed, methyl iodide (0.69 g, 4.69 mmol) in 1 ml of THF was added and the mixture was stirred for 1 hour. The solvent was removed under reduced pressure and 50 ml of water was added to the residue. The mixture was stirred vigorously for 20 min and a light yellow solid was collected by filtration. The light yellow product was purified by flash column chromatography using toluene/hexanes from 2:3 as eluant and isolated in 1.24 g (66.3%) yield. $^1$H NMR (CDCl3, 500 MHz) δ ppm: 7.58 (d, J=8.0 Hz, 1H), 7.48 (d, J=8.5 Hz, 2H), 7.45 (d, J=9.0 Hz, 2H), −7.43 (d, J=16.5 Hz, 1H, =CH), 7.38 (s, 1H), 7.33 (d, J=7.5 Hz, 1H), 7.08 (d, J=16.5 Hz, 1H, =CH), 7.01 (d, J=16.0 Hz, 1H, =CH), 6.94 (d, J=16.5 Hz, 1H, =CH), 6.90 (d, J=8.0 Hz, 4H), 4.0 (t, J=6.2 Hz, 4H, CH2), 2.50 (s, 3H, CH3), 1.79 (m, 4H, CH2), 1.52 (m, 4H, CH2), 0.99 (t, J=7.2 Hz, 6H, CH3)13C NMR (CDCl3, 125.7 MHz) δ ppm: 158.9, 137.0, 136.8, 135.9, 130.1, 129.7, 128.4, 127.9, 127.7, 125.65, 125.59, 123.6, 123.3, 114.7, 67.7, 31.3, 19.2, 16.8, 13.8

Anal. Calcd. for $C_{31}H_{36}O_2S$: C, 78.77; H, 7.68;. Found: C, 78.52; H, 7.65.

Example 68

Preparation of 4,4'-di(n-butyl)triphenylamine (72). To a solution of tris(dibenzylideneacetone)dipalladium (Pd$_2$(dba)$_3$) (0.66 g, 0.72 mmol) and bis(diphenylphospino)ferrocene (DPPF) (0.47 g, 0.85 mmol) in 150 ml of dry toluene was added 1-bromo-4-n-butyl benzene (15 g, 70.4 mmol) at room temperature under nitrogen; the resultant mixture was stirred for 10 minutes, and sodium tert-butoxide (10.54 g) and aniline (3.2 g, 34.4 mmol) were then added to this solution which was then stirred for 20 h at 90° C. The mixture was allowed to cool, poured into 150 ml of water and extracted three times (3×200 ml) with ether. The combined organic layer was dried over anhydrous magnesium sulfate. After removal of solvent under reduced pressure, the product was purified by flash column chromatography using 10% of ethyl acetate in hexanes as eluant and was isolated in 93.1% (11.6 g) yield.

Example 69

Preparation of 4,4'-dibutyl-4"-formyl triphenylamine (73). To a solution of 4,4'-di-n-butyldiphenlylamine (72) (11.6 g, 32.3 mmol) in 120 ml of DMF at 0° C. was added POCl$_3$ (6.93 g, 45.2 mmol) dropwise. The resulting mixture was stirred at 95-100° C. under nitrogen for 20 hour. The mixture was cooled, poured into 300 ml of ice-water slowly, neutralized with 4 M aqueous NaOH and extracted three times (3×200 ml) with ether. The combined organic layer was washed with saturated brine and dried over magnesium sulfate. After removal of solvent, the product was purified by flash chromatography using 10% of ethyl acetate in hexanes as eluant and was isolated in 72.3% (8.66 g) yield. $^1$H NMR (CDCl$_3$, 500 MHz) δppm: 9.79 (s, 1H, CHO), 7.64 (d, J=9.0 Hz, 2H), 7.15 (d, J=8.5 Hz, 4H), 7.09 (d, J=8.5 Hz, 4H), 6.95 (d, J=9.0 Hz, 2H), 2.61 (d, J=7.7 Hz, 4H, CH$_2$), 1.62 (m, 4H, CH$_2$), 1.38 (m, 4H, CH$_2$), 0.95 (t, J=7.2 Hz, 6H, CH$_3$).

Example 70

Preparation of 2,5-dibromo-E,E-1,4-bis[N,N,N',N'-tetra-(4-n-butyl phenyl)aminostyryl]benzene (76). To a solution of 4,4'-dibutyl-4"-formyl triphenylamine (73) (3.1 g, 8.36 mmol) and tetraethyl 2,5-dibromo-α,α'-p-xylenebisphosphonate (69) (2.17 g, 4.05 mmol) in dry THF (50 ml) at 0° C. was added 9 ml of a 1 M solution of KO$^t$Bu in THF. After 2 hours the reaction was quenched by addition of 10 ml of water; THF was removed under reduced pressure. 50 ml of water was added to the residue, the mixture was extracted three times by methylene chloride/ether (1:4) (3×120 ml). The combined organic layer was dried over magnesium sulfate. After removal of solvent, the product was purified by flash chromatography using toluene/hexanes (1/4) as eluant and was isolated in 83.2% (3.37 g) yield. $^1$H NMR (CDCl$_3$, 500 MHz) δppm: 7.82 (s, 2H), 7.37 (d, J=8.5 Hz, 4H), 7.20 (d, J=16.0 Hz, 2H, =CH), 7.08 (d, J=8.0 Hz, 8H), 7.03 (d, J 8.0 Hz, 8H), 7.0 (d, J=8.5 Hz, 4H), 6.97(d, J=16.0 Hz, 2H, =CH), 2.57 (t, J=7.7 Hz, 8H, CH$_2$), 1.60 (m, 8H, CH$_2$), 1.37 (m, 8H, CH2), 0.94 (t, J=7.5 Hz, 12H, CH$_3$) $^{13}$C NMR (CDCl$_3$, 125.7 MHz) δppm: 148.5, 144.9, 138.1, 137.1, 131.5, 129.8, 129.5, 129.2, 127.7, 124.9, 123.3, 122.9, 121.8, 35.1, 33.7, 22.4. 14.0.

Example 71

Preparation of 2-bromo-E,E-1,4-bis[N,N,N'N'-tetra-(4-n-butyl phenyl)aminostyryl]benzene (77). To a solution of 4,4'-dibutyl-4"-formyl triphenylamine (73) (4.0 g, 10.8 mmol) and tetraethyl 2-bromo-α,α'-p-xylenebisphosphonate (70) (2.46 g, 5.37 mmol) in dry THF (65 ml) at 0° C. was added 11 ml of 1 M solution of KO$^t$Bu in THF. After 2 hours the reaction was quenched by addition of 10 ml of water and THF was removed under reduced pressure. 50 ml of water was then added to the residue and the mixture was extracted three times with methylene chloride/ether (1:4) (3×120 ml). The combined organic layer was dried over magnesium sulfate. After removal of solvent, the product was purified by flash chromatography using methylene chloride/ethyl acetate/hexanes (1/1/4) as eluant and was isolated in 86.2% (4.27 g) yield. $^1$H NMR (CDCl$_3$, 500 MHz) δppm: 7.68 (s, 1H), 7.62 (d, J=8.5 Hz, 1H), 7.28-7.42 (m, 6H), 6.96-7.12 (m, 22H), 6.85 (d, J=16.0 Hz, 1H, =CH), 2.57 (d, J=7.7, 8H, CH$_2$), 1.58 (m, 8H, CH$_2$), 1.37 (m, 8H, CH$_2$), 0.94 (t, J=7.2 Hz, 12H, CH$_3$) $^{13}$C NMR (CDCl$_3$, 125.7 MHz) δppm: 148.2, 148.1, 145.0, 138.1, 137.9, 135.7, 130.5, 130.4, 130.1, 129.9, 129.2, 127.5, 127.3, 126.1, 125.2, 124.7, 124.4, 124.2 122.2, 122.1, 35.1, 33.7, 22.4, 14.0.

Example 72

Preparation of 2,5-dimethythio-E,E-1,4-bis[N,N,N',N'-tetra-(4-n-butyl phenyl)aminostyryl]benzene (80). 1.7 M tert-butyl lithium (3.7 ml, 6.29 mmol) was added dropwise to a stirred solution of 2,5-dibromo-E,E-1,4-bis[N,N,N',N'-tetra-(4-n-butyl phenyl)aminostyryl]benzene (76) (1.5 g, 1.50 mmol) in 20 ml of THF under nitrogen at −78° C. After 30 min the mixture was allowed to rise to ambient temperature and sulfur (0.10 g, 3.12 mmol) was added while a brisk stream of nitrogen was passed through the open system to exclude air. After sulfur was consumed, methyl iodide (0.44 g, 3.12 mmol) in 1 ml of THF was then added and the mixture was stirred for 1 hour. The solvent was removed under reduced pressure and 30 ml of water was added to the residue. The mixture was extracted three times with ether (3×100 ml) and the combined organic layer was dried over magnesium sulfate. After removal of solvent, the residue was washed three times with methanol to remove a side product. The product was purified three times by flash column chromatography using toluene/hexanes in ratios varying from 1:4 to 3:7 as eluent to afford a poor yield of the product. $^1$H NMR (CDCl$_3$, 500 MHz) δppm: 7.53 (s, 2H), 7.42 (d, J=16.0 Hz, 2H, =CH), 7.39 (d, J=8.0 Hz, 4H), 7.07 (d, J=8.5 Hz, 8H), 7.03 (d, J=8.0 Hz, 8H), 6.96-7.02 (m, 5H, 4 Ar—H, 1 =CH), 2.57 (t, J=7.7 Hz, 8H, CH2), 2.48 (s, 6H, SCH$_3$), 1.60 (m, 8H, CH$_2$), 1.37 (m, 8H, CH$_2$), 0.94 (t, J=7.2 Hz, 12H, CH$_3$) $^{13}$C NMR (CDCl$_3$, 125.7 MHz) δppm: 148.0, 145.0, 137.8, 136.7, 134.2, 130.4, 130.0, 129.2, 127.5, 125.3, 124.7, 123.1, 122.2, 35.0, 33.7, 22.4. 17.3, 14.0.

Example 73

Preparation of 2-methylthio-E,E-1,4-bis[N,N,N',N'-tetra-(4-n-butyl phenyl)aminostyryl]benzene (81). 1.7 M tert-butyl lithium (5.1 ml, 8.67 mmol) was added dropwise to a stirred solution of 2-bromo-E,E-1,4-bis[N,N,N',N'-tetra-(4-n-butyl phenyl)aminostyryl]benzene (77) (2.0 g, 2.17 mmol) in 50 ml of THF under nitrogen at '78° C. After 30 min the mixture was allowed to rise to ambient temperature and sulfur (0.076 g, 2.38 mmol) was added while a brisk stream of nitrogen was passed through the open system to exclude air. After sulfur was consumed, methyl iodide (0.34 g, 2.39 mmol) in 1 ml of THF was added and the mixture was stirred for 1 hour. The solvent was removed under reduced pressure and 50 ml of water was added to the residue. The mixture was extracted three times with ether (3×100 ml) and the combined organic layer was dried over magnesium sulfate. After removal of solvent, the residue was washed three times with methanol to remove a side product. The yellow product was purified by flash column chromatography using toluene/hexanes in ratios varying from 1:4 to 3:7 as eluent and isolated in 0.62 g (32.1%) yield. $^1$H NMR (CDCl$_3$, 500 MHz) δppm: 7.57 (d, J=8.0 Hz, 1H), 7.44 (d, J=16.0 Hz, 1H, =CH), 7.39 (d, J=8.5 Hz, 2H), 7.38 (s, 1H), 7.35 (d, J=8.5 Hz, 2H), 7.32 (d, J=8.5 Hz, 1H), 6.7-7.1 (m, 22H), 6.93 (d, J=16.0 Hz, 1H, =CH), 2.57 (d, J=7.7, 8H, CH$_2$), 2.50 (s, 3H, CH$_3$), 1.60 (m, 8H, CH$_2$), 1.37 (m, 8H, CH$_2$), 0.94 (t, J=7.2 Hz, 12H, CH$_3$) $^{13}$C NMR (CDCl$_3$, 125.7 MHz) δ ppm: 147.9, 145.1, 137.82, 137.76, 137.1, 136.8, 135.9, 130.7, 130.3, 129.7, 129.1, 128.4, 127.4, 127.2, 125.6, 124.65, 124.60, 123.6, 123.3, 122.4, 122.3, 35.0, 33.7, 22.4, 16.8, 14.0 Anal. Calcd. for C$_{63}$H$_{70}$N$_2$S: C, 85.28; H, 7.95;. N, 3.16. Found: C, 85.46; H, 8.04; N, 3.23.

Example 74

Preparation of E,E{2,5-bis[2-(4-butoxyphenyl)vinyl]phenyl}(dimethyl)sulfonium triflate (82). 2-Methylthio-E,E-1,4-bis[N,N,N',N'-tetra-(4-n-butylphenyl)aminostyryl]benzene (0.39 g, 0.75 mmols) was dissolved in dry methylene chloride (14 ml). The solution was cooled to −78° C. and placed under a nitrogen atmosphere. Methyl trifluoromethanesulfonate (0.21 ml, 1.88 mmol) was added via syringe to the cooled solution in the dark. After mixing for 30 minutes at −78° C. the solution was stirred at room temperature for two days. 50 ml of ether was added to the mixture and the resulting solid was collected by filtration and washed three times with ether to give the light yellow product in 0.56 g (85%) yield. $^1$H NMR (CDCl$_3$, 500 Mz) δ ppm: 7.54 (d, J=8.5 Hz, 2H), 7.42 (d, J=16, 2H), 7.18 (d, J=16.0 Hz, 2H), 7.00 (t, J=9.0 Hz, 8H), 4.00 (m, 4H, CH$_2$), 3.32 (s, 12H, CH$_3$), 1.70 (m, 4H, CH$_2$), 1.43 (m, 4H, CH$_2$), 0.94 (m, 6H, CH$_3$).

Example 75

Preparation of 10-(4-butylphenyl)-10H-phenothiazine (83). To a solution of tris(dibenzylideneacetone)dipalladium (Pd$_2$(dba)$_3$) (0.30 g, 0.33 mmol) and bis(diphenylphosphino) ferrocene (DPPF) (0.22 g, 0.40 mmol) in dry toluene (60 ml) under nitrogen atmosphere was added 4-(butyl)phenylbromide (3.21 g, 15.1 mmol) at room temperature, and the resultant mixture was stirred for 10 min., sodium tert-butoxide (4.0 g) and phenothiazine (3.0 g, 15.1 mmol) were added to this solution and stirred at 90° C. overnight under nitrogen. The reaction mixture was poured into water (80 ml), extracted three times with ether (100 ml×3) and dried over anhydrous magnesium sulfate. The product was purified by flash column chromatography using 5% ethyl acetate in hexane as eluant and was isolated in 81% (4.03 g) yield as a pale yellow solid. $^1$H NMR (CDCl$_3$, 500 MHz) δppm: 7.41 (d, J=7.0 Hz, 2H), 7.29 (d, J=8.0 Hz, 2H), 7.0 (dd, J=7.5 Hz, J=1.5 Hz, 2H), 6.7-6.9 (m, 4H), 6.20 (d, J=7.5 Hz, 2H), 2.72 (t, J=7.5 Hz, 2H, CH$_2$), 1.7 (m, 2H, CH$_2$), 1.44 (m, 2H, CH$_2$), 0.99 (t, J=7.0 Hz, 3H, CH$_3$).

Example 76

Preparation of 10-(4-butylphenyl)-5-phenyl-10H-phenothiazin-5-ium hexa-fluorophosphate (84). A mixture of 10-(4-butylphenyl)-10H-phenothiazine (83) (1.44 g, 4.34 mmol), diphenyliodonium hexafluorophosphate (1.85 g, 4.34 mmol) and copper (I) benzoate (0.10 g) was heated at 120° C. for 3 hours under nitrogen. Upon cooling to ambient temperature, the mixture was transferred to a mortar-and-pestle and 50 ml of ether was added. The solid was finely powdered, washed with ether, collected by filtration and washed three times with ether. Without further purification, it was isolated in 98.2% (2.36 g) yield as a pale yellow solid.

$^1$H NMR (DMSO, 500 MHz) δppm: 8.37 (d, J=8.0 Hz, 2H1), 7.6-7.8 (m, 5H), 7.4-7.5 (m, 4H), 7.20 (d, J=7.5 Hz, 2H), 6.74 (d, J=8.5 Hz, 2H), 2.73 (t, J=8.0 Hz, 2H, CH$_2$), 1.65 (m, 2H, CH$_2$), 1.38 (m, 2H, CH$_2$), 0.94 (t, J=7.0 Hz, 3H, CH$_3$).

Example 77

Preparation of N,N-bis(4butylphenyl)-N-(4-{2[4-(10H-phenothiazin-10-yl)phenyl]vinyl}phenyl)amine (86). To a solution of tris(dibenzylideneacetone) dipalladium (Pd$_2$(dba)$_3$) (0.13 g, 0.14 mmol) and bis(diphenylphosphino)ferrocene (DPPF) (0.10 g, 0.17 mmol) in dry toluene (20 ml) under nitrogen atmosphere was added 4-[2-(4-bromophenyl) vinyl]-N, N-bis(4-butylphenyl)aniline (2.60 g, 4.83 mmol) at room temperature, and the resultant mixture was stirred for 10 min. Sodium tert-butoxide (1.3 g) and phenothiazine (0.96 g, 4.83 mmol) were then added to this solution, which was then stirred at 90° C. overnight under nitrogen. The reaction mixture was poured into water (60 ml), extracted three times with ether (100 ml×3) and dried over anhydrous magnesium sulfate. The product was purified by flash column chromatography using 2% ethyl acetate in hexane as eluant and was isolated in 60% (1.91 g) yield as a yellow solid.

$^1$H NMR (CDCl$_3$, 500 MHz) δppm: 7.70 (d, J=8.5 Hz, 2H), 7.39 (d, J=7.0 Hz, 2H), 7.35 (d, J=8.5 Hz, 2H), 7.13 (d, J=16.0 Hz, 1H, =CH), 7.09 (d. J=8.5 Hz, 4H), 7.0-7.03 (m, 9H), 6.87 (td, J=7.5 Hz, J=1.5 Hz, 2H), 6.82 (td, J=7.5 Hz, J=1.5 Hz, 2H), 6.29 (dd, J=8.5 Hz, J=1.5 Hz, 2H), 2.59 (t, J=7.5 Hz, 4H, CH$_2$), 1.63 (m, 4H, CH$_2$), 1.40 (m, 4H, CH$_2$), 0.96 (t, J=7.0 Hz, 6H, CH$_3$). $^{13}$C NMR (CDCl$_3$, 125 MHz) δppm: 148, 145, 144, 140, 137.9, 137.6, 131, 130, 129.5, 129.2, 128, 127, 126.8, 126.7, 125, 124.7, 122.5, 122.2, 120, 116, 35, 34, 22, 14. HR-FAB: calcd. for C$_{46}$H$_{44}$N$_2$S: M$^+$, 656.32; found M$^+$, 656.3233.

Example 78

Preparation of 10-(2-{4-[bis(4-butylphenyl)amino] phenyl}vinyl)-5-phenyl-10H-phenothiazin-5-ium hexafluorophosphate (87). A mixture of N,N-bis(4-butylphenyl)-N-(4-{2-[4-(10H-phenothiazin-10-yl)phenyl]vinyl}phenyl) amine (0.5 g, 0.76 mmol), diphenyliodonium hexafluorophosphate (0.32 g, 0.76 mmol) and copper (I) benzoate (0.02 g) in 10 ml of chlorobenzene was heated at 120° C. for 3 hours under nitrogen. Upon cooling to ambient temperature, the mixture was poured into 50 ml of hexanes. The yellow precipitate was collected by filtration and washed three times with ether. The product was purified by flash column using methylene chloride as eluant to give 0.13 g of lightly yellow product.

$^1$H NMR (d$_6$-DMSO, 500 MHz) δppm: 8.12 (d, J=8.0 Hz, 2H), 7.82 (d, J=8.0 Hz, 2H), 7.54-7.74 (m, 5H), 7.40-7.52 (m, 4H), 7.34 (d, J=8.0 Hz, 2H), 7.28 (d, J=16 Hz, 4H), 7.1-7.23 (m, 8H), 6.80-7.04 (m, 8H), 2.58 (t, J=7.5 Hz, 4H, CH$_2$), 1.63 (m, 4H, CH$_2$), 1.40 (m, 4H, CH$_2$), 0.96 (t, J=7.0 Hz, 6H, CH$_3$).

Example 79

Preparation of 3-bromophenyldiazonium hexafluorophosphate (88). To a solution of hydrochloric acid (36.5%, 24 ml) in 180 ml of water was added m-bromoaniline in one portion (15 g, 0.087 mol). Then a solution of sodium nitrite (7.5 g) in 18 ml of water was added slowly while the mixture was maintained between −5° C. and 10° C. The mixture was stirred for an additional 30 min and the precipitate was collected by filtration. The solid was dissolved in 20 ml of methanol and then poured into 300 ml of ether; the white solid was collected by filtration to afford 6.1 g (63%) of 3-bromophenyldiazonium hexafluorophosphonate.

Example 80

Preparation of 3-bromo diphenylsulfide (89). To a solution of 3-bromophenyldiazonium hexafluorophosphonate (88) (2.5 g, 7.59 mmol) in 15 ml of anhydrous DMSO was added a solution of benzenethiolate 91.0 g, 7.57 mmol) in 30 ml of DMSO at 0° C. The mixture was stirred at room temperature for 24 hours, poured into 100 ml of water and then extracted three times with ether. The combined organic layer was dried over anhydrous magnesium sulfate. After removal of solvent, the product was purified by flash chromatography using hexane as eluant.

$^1$H NMR (CDCl$_3$, 500 MHz) δ ppm: 7.38-7.43 (m, 3H), 7.28-7.38 (m, 4H), 7.20 (dt, J=8.0 Hz, J=1.5 Hz, 1H), 7.14 (t, J=7.5 Hz, 1H).

$^{13}$C NMR (CDCl$_3$, 125 MH) δ ppm: 139.0, 133.8, 132.3, 132.2, 130.3, 129.6, 129.4, 128.3, 127.9, 122.9.

Example 81

Preparation of 3-phenylthio triphenylamine (90). To a solution of tris(dibenzylideneacetone)dipalladium (Pd$_2$(dba)$_3$) (0.05 g, 0.05 mmol) and bis(diphenylphosphino)ferrocene (DPPF) (0.04 g, 0.07 mmol) in dry toluene (10 ml) under nitrogen atmosphere was added 3-bromodiphenylsulfide (89) (0.75 g, 2.83 mmol) at room temperature, and the resultant mixture was stirred for 10 min. Sodium tert-butoxide (0.75 g) and diphenylamine (0.48 g, 2.83 mmol) were added to this solution and stirred at 90° C. overnight under nitrogen. The reaction mixture was poured into water (60 ml), extracted three times with ether (60 ml×3) and dried over anhydrous magnesium sulfate. The product was purified by flash column chromatography using hexane as eluant and was isolated in 60% (0.6 g) of yellow solid.

Example 82

Preparation of [3-(diphenylamino)phenyl](diphenyl)sulfonium (91). The mixture of 3-phenylthio triphenylamine (90) (0.6 g, 1.70 mmol) and diphenyliodonium hexafluorophosphate (0.73 g, 1.70 mmol) and copper (I) benzoate (0.02 g) in 10 ml of chlorobenzene was heated at 120° C. for 3 hours under nitrogen. Upon cooling to ambient temperature, the mixture was poured into 50 ml of hexanes. The yellow precipitate was collected by filtration and washed three times with ether. The product was purified by flash column using methylene chloride as eluant to give 0.26 g of a light yellow product.

$^1$H NMR (CDCl$_3$, 500 MHz) δppm: 7.74 (t, J=7.0 Hz, 2H), 7.67 (t, J=7.0 Hz, 4H), 7.61 (d, br, J=8.0 Hz, 4H), 7.40 (t, J=8.0 Hz, 1H), 7.26-7.34 (m, 5H), 7.14 (t, J=7.0 Hz, 1H), 7.08 (d, br, J=7.5 Hz, 4H), 7.03 (dd, J=8.0 Hz, J=2.0 Hz, 1H), 6.84 (t, J=2.0 Hz, 1H).

Example 83

Preparation of 4-N,N-dibutylaminobenzaldehyde (92). A solution of dibutylaniline (20 g, 0.0975 mol) in 12 ml of dichloroethane was added to a solution of DMF (25 ml) and POCl$_3$ (10 ml) in 12 ml of dichloroethane at 0° C. The mixture was heated to reflux for 3 hours with vigorous evolution of HCl and was allowed to cool to ambient temperature. 300 ml of methylene chloride was added, washed with a 2M solution of sodium hydroxide and three times with water, and dried over anhydrous sodium sulfate. After removal of solvent, the product was purified by flash chromatography using ethyl acetate and hexanes (1:10) as eluant and was isolated in 18.15 g (79.9%).

$^1$H NMR (CDCl$_3$, 500 MHz) δppm: 9.72 (s, 1H, CHO), 7.70 (d, J=8.5 Hz, 2H), 6.65 (d, J=8.5 Hz, 2H), 3.35 (t, J=7.5 Hz, 4H, CH$_2$), 1.61 (m, 4H, CH$_2$), 1.38 (m, 4H, CH$_2$), 0.98 (t, J=7.5 Hz, 6H, CH$_3$)

$^{13}$C NMR (CDCl$_3$, 125.7 MHz) δ ppm: 189.9, 152.5, 132.2, 124.4, 112.7, 110.6, 50.8, 29.2, 20.2, 13.9.

Example 84

Preparation of 4-N,N-dimethylaminobenzylalcohol (93). NaBH$_4$ (0.976 g, 0.025 mol) was added to a solution of 4-N,N-dibutylaminobenzaldehyde (92) (2 g, 0.012 mol) in 100 ml of methanol at room temperature. The resultant mixture was stirred for 30 min and poured into 100 ml of water. The mixture was extracted three times with ether and combined organic layer was washed with brine and dried over magnesium sulfate. Removal of solvent was isolated in 2.71 g (89.4%) yield as an NMR-pure compound.

$^1$H NMR (CDCl$_3$, 500 MHz) δ ppm: 7.21 (d, J=8.0 Hz, 2H), 6.63 (d, J=8.5 Hz, 2H), 4.55 (d, J=5.5 Hz, 2H, CH$_2$O), 3.27 (t, J=7.7 Hz, 4H, CH$_2$), 1.57 (m, 4H, CH$_2$), 1.36 (m, 4H, CH$_2$), 0.96 (t, J=7.5 Hz, 6H, CH$_3$)

$^{13}$C NMR (CDCl$_3$, 125.7 MHz) δppm: 147.9, 128.9, 127,2, 111.5, 65.5, 50.8, 29.3, 20.3, 14.0.

Example 85

Preparation of 4-N,N-dibutylaminobenzyl chloride hydrochloride (94). 4-(dibutylamino)benzylalcohol (93) (4.32 g) and concentrated hydrochloric acid (40 ml) were heated at 110° C. for 15 h. The volatile material was removed on a rotary evaporator to give the product in 96.1% (5.14 g) yield.$^1$H NMR (CDCl$_3$, 500 MHz) dppm: 7.76 (d, J=8.0 Hz, 2H), 7.55 (d, J=8.0 Hz, 2H), 4.60 (s, 2H, CH$_2$), 3.20 (d, br, 4H, CH$_2$, 1.90 (d, br, 4H, CH$_2$), 1.36 (d, br, 4H, CH$_2$), 0.85 (t, J=6.2 Hz, 6H, CH$_3$).

Example 86

Preparation of diethyl 4-dibutylaminobenzyl phosphonate (95). A solution of 4-N,N-dibutylaminobenzyl chloride hydrochloride (94) (6.34 g, 21.8 mmol) and triethyl phosphite (100 ml) was heated to reflux for 24 hours. Excess triethyl phosphite was removed under reduced pressure, the reminder was neutralized with saturated NaHCO$_3$ solution and extracted three times with ether. The combined organic layer was dried over magnesium sulfate. Removal of solvent was isolated in 6.97 g (90.1%) yield as NMR-pure compound. $^1$H NMR (CDCl$_3$, 500 MHz) δ ppm: 7.10 (dd, $^3$J=9.0 Hz, $^4$J=2.5 Hz, 2H), 6.57 (d, J=8.5 Hz, 2H), 4.01 (m, 4H, PCH$_2$), 3.23 (t, J=7.5 Hz, 4H, NCH$_2$), 3.05 (d, J=21 Hz, 2H, CH$_2$), 1.54 (m, 4H, CH$_2$), 1.36 (m, 4H, CH$_2$), 1.25 (t, J=7.5 Hz, 6H, CH$_3$), 0.95 (t, J=7.0 Hz, 6H, CH$_3$).

Example 87

Preparation of 4-N-tert-butoxycarbonyl-N'-(p-formylphenyl)piperazine (piperazinobenzaldehyde (97). To a mixture of piperazine (10.41 g, 0.121 mol) and K$_2$CO$_3$ (5.67 g, 0.041 mol) in 15 ml of DMSO was added dropwise 4-fluorobenzaldehyde (5 g, 0.0403 mol) in 5 ml of DMSO at 100° C. The resultant mixture was stirred at 100° C. overnight. The mixture was allowed to cool to ambient temperature and poured into 500 ml of water to remove excess piperazine. The yellow solid was collected by filtration and washed three times by water. The product was used in the next step without further purification.

To a solution of 4-piperazinobenzaldehyde (4.83 g, 0.0254 mol) and di-tert-butyl dicarbonate (5.55 g, 0.0254 mol) in 60 ml of methylene chloride was added triethylamine (2.52 g, 0.0254 mol) at 0° C. The mixture was stirred at 0° C. for 2 hours, washed three times with water and dried over anhydrous sodium sulfate. The product was purified by flash chromatography using ethyl acetate/hexanes varying in ratio from 1/4 to 3/7 and was isolated in a yield (over two steps) of 47.5% (5.56 g)$^1$H NMR (500 MHz, CDCl$_3$) δ ppm: 9.80 (s, 1H, CHO), 7.77 (d, J=8.5 Hz, 2H), 6.91 (d, J=8.5 Hz, 2H), 3.59 (m, 4H, CH$_2$), 3.39 (m, 4H, CH$_2$), 1.49 (s, 9H, CH$_3$)$^{13}$C NMR (125.7 MHz, CDCl$_3$) δppm: 190.4, 154.8, 154.6, 131.8, 127.4, 113.7, 80.2, 47.0, 28.4.

Example 88

Preparation of 4-N,N-di-n-butylamino-4'-N'-t-butoxycarbonylpiperazino stilbene (98). To a solution of diethyl 4-N,N-di-n-butylaminobenzylphosphonate (95) (2.0 g, 5.63 mmol) and 4-N-tert-butoxycarbonylpiperazinobenzaldehyde (97) (1.63 g, 5.63 mmol) in 30 ml of THF was added 1M potassium tert-butoxide (6 ml) in THF at 0° C. The mixture was stirred for 2 h at 0° C. and allowed to rise to ambient temperature. The reaction was quenched by addition of 40 ml of water. The mixture was extracted three times with 70 ml of ether and the combined organic layer was dried over anhydrous magnesium sulfate. After removal of solvent, the product was purified by recrystallization from methanol to give a yield of 2.05 g (74.2%). $^1$H NMR (CDCl$_3$, 500 MHz) δppm: 7.39 (d, J=8.5 Hz, 2H), 7.34 (d, J=9.0 Hz, 2H), 6.85-6.95 (m, overlap, 3H), 6.81 (d, J=16.5 Hz, 1H, =CH), 6.61 (d, J=9.0 Hz, 2H), 3.59 (t, J=4.7 Hz, 4H, CH$_2$), 3.28 (t, J=7.2 Hz, 4H, CH$_2$), 3.15 (s, br, 4H, CH$_2$), 1.58 (m, 4H, CH$_2$), 1.49 (s, 9H, CH$_3$), 1.37 (m, 4H, CH$_2$), 0.96 (t, J=7.2 Hz, 6H, CH$_3$). $^{13}$C NMR (CDCl$_3$, 125.7 MHz) δppm: 154.7, 149.9, 147.4, 138.6, 127.4, 126.8, 126.6, 124.8, 123.2, 116.6, 111.6, 79.9, 50.8, 49.3, 29.4, 28.4, 20.3, 14.0 (one carbon was not observed).

HRMS (FAB): calcd for C$_{31}$H$_{45}$N$_3$O$_2$: M$^+$491.35. Found 491.3519.

Anal. Calcd. for C$_{31}$H$_{45}$N$_3$O$_2$: C, 75.72; H, 9.22;. N, 8.55. Found: C, 75.76; H, 9.31; N, 8.65.

Example 89

Preparation of 4-N,N-di-n-butylamino-4'-piperazino stilbene (99). To a solution of 4-N,N-di-n-butylamino-4'-N'-tert-butoxycarbonylpiperazino stilbene (98) (0.5 g, 1.02 mmol) in 20 ml of THF was added 2 ml of 2M hydrochloric acid. The mixture was heated to reflux for 4 h and allowed to cool to room temperature. The solution was neutralized with a solution of sodium hydroxide and extracted three times with ether (30 ml). The combined organic layer was dried over anhydrous magnesium sulfate. After removal of solvent, the product was purified by recrystallization from methanol to give a yield of 0.36 g (89.7%). $^1$H NMR (CDCl$_3$, 500 MHz) δppm: 7.39 (d, J=9.0 Hz, 2H), 7.34 (d, J=9.0 Hz, 2H), 6.85-6.95 (m, overlap, 3H), 6.82 (d, J=16.0 Hz, 1H, =CH), 6.61 (d, J=8.5 Hz, 2H), 3.28 (t, J=7.7 Hz, 4H, CH$_2$), 3.16 (t, J=4.7 Hz, 4H, CH$_2$), 3.04 (t, J=4.7 Hz, 4H, CH$_2$), 1.58 (m, 4H, CH$_2$), 1.36 (m, 4H, CH$_2$), 0.96 (t, J=7.2 Hz, 6H, CH$_3$). $^{13}$C NMR (CDCl$_3$, 125.7 MHz) δppm: 150.5, 147.4, 130.0, 127.3, 126.7, 126.2, 125.0, 123.4, 116.1, 111.6, 50.8, 50.3, 46.1, 29.4, 20.3, 14.0

HRMS (FAB): calcd for C$_{26}$H$_{37}$N$_3$: M$^+$391.30. Found 491.2992.

Anal. Calcd. for C$_{26}$H$_{37}$N$_3$: C, 79.75; H, 9.52;. N, 10.73. Found: C, 78.92; H, 9.31; N, 10.72.

Example 90

Preparation of 4-N,N-di-n-butylamino-4'-(1-piperazino) stilbene N'-triphenyl sulfonium hexafluorophosphate (100). The mixture of 4-N,N-di-n-butylamino-4'-(1-piperazino)stilbene (99) (0.80 g, 2.04 mmol) and 4-fluorotriphenylsulfonium hexafluorophosphate (TPSP) in 10 ml of N,N-dimethyl sulfoxide was heated to 100° C. for 6 hours. Upon cooling to ambient temperature, the mixture was poured into a 5% aqueous solution of potassium hexafluorophosphate. The yellow solid was collected by filtration and washed three times with the above solution. The product was purified by flash chromatography using neutral alumina and methylene chloride/methanol as eluant.

$^1$H NMR (CDCl$_3$, 500 MHz) δ ppm: 7.69 (t, br, J=7.5 Hz, 2H), 7.62 (t, J=7.5 Hz, 4H), 7.54 (d, J=7.5 Hz, 4H), 7.52 (d, J=9.5 Hz, 2H), 7.35 (d, J=8.5 Hz, 2H), 7.33 (d, J=9.0 Hz, 2H), 7.07 (d, J=9.0 Hz, 2H), 6.87 (d, J=16.0 Hz, 1H, =CH), 6.85 (d, J=8.5 Hz, 2H), 6.78 (d, J=16.0 Hz, 1H, =CH), 6.61 (d, J=8.5 Hz, 2H), 3.28 (t, J=7.7 Hz, 4H, CH$_2$), 3.30 (t, br, 4H, CH$_2$), 3.04-3.3 (m, 8H), 1.56 (m, 4H, CH$_2$), 1.34 (m, 4H, CH$_2$), 0.96 (t, J=7.0 Hz, 6H, CH$_3$). $^{13}$C NMR (CDCl$_3$, 125.7 MHz) δppm: 154.6, 149.1, 147.5, 134.1, 133.3, 131.5, 130.6, 130.1, 127.4, 126.8, 126.6, 126.0, 124.8, 123.2, 116.2, 115.7, 111.6, 105.7, 50.8, 48.6, 46.4, 29.4, 20.4, 14.0

HRMS (FAB): calcd. for C$_{44}$H$_{50}$N$_3$S: M$^+$652.37. Found 652.3721.

Anal. Calcd. for C$_{44}$H$_{50}$N$_3$F$_6$PS: C, 67.23; H, 6.32;. N, 5.27. Found: C, 67.47; H, 6.61; N, 5.22.

Example 91

Preparation of 2,5-bis-(chloromethyl)-1,4-dimethoxybenzene (101). To a stirred solution of the dimethyl ether of hydroquinone (10.3 g, 74.5 mmol), 60 ml of dioxane and 10 ml concentrated hydrochloric acid was added two portions of 37% formalin (11 ml) at thirty-minute intervals. During the period of addition, hydrogen chloride gas was passed through. Stirring and the introduction of hydrogen chloride gas were continued for three hours longer and then 50 ml of concentrated hydrochloric acid was added. After cooling, white solids were collected and washed three times by water. Recrystallization from acetone gave 9.8 g of product (56.2%). $^1$H NMR (CDCl$_3$, 500 MHz) δppm: 6.98 (s, 2H), 4.61 (s, 4H), 3.94 (s, 6H).

Example 92

Preparation of tetraethyl 2,5-bismethoxyl-p-xylene phosphonate (102). 2,5-Bis-(chloromethyl)-1,4-dimethoxybenzene (101) (7.15 g, 30.2 mmol) and triethyl phosphite (60 ml) were heated to reflux for 24 hours. After removal of unreacted triethyl phosphite under reduced pressure, 100 ml of hexanes were added to the mixture. The white solid was collected by filtration, washed three times with hexanes, dried in vacuo and isolated in 94.3% (12.48 g) yield. $^1$H NMR (CDCl$_3$, 500 MHz) δppm: 6.91 (s, 2H, ArH), 4.02 (m, 8H, CH$_2$), 3.93 (t, J=6.0 Hz, 4H, CH$_2$), 3.22 (d, J=20.0 Hz, 4H, CH$_2$), 1.75 (m, 4H, CH$_2$), 1.48 (m, 4H, CH$_2$), 1.24 (t, J=7.0 Hz, 12H, CH$_3$), 0.97 (t, J=7.2 Hz, 6H, CH$_3$)

Example 93

Preparation of diethyl 4-{(E)-2-[4-(dibutylamino) phenyl}ethenyl}-2,5-dimethoxybenzylphosphonate (103). To a solution of diethyl 4-N,N-di-n-butylaminobenzaldehyde (1.80 g, 7.725 mmol) and tetraethyl 2,5-bismethoxy-p-xylene phosphonate (102) (5.18 g, 11.8 mmol) in 100 ml of THF was added 1M of potassium tert-butoxide (7.8 ml) in THF at 0° C. The mixture was stirred for 5 h at 0° C. and allowed to rise to ambient temperature. The reaction was quenched by addition of 40 ml of water and the solvent was removed under reduced pressure. The product was purified by flash chromatography using ethyl acetate and ethyl acetate/methanol (8:2) as eluant and was isolated in 57.8% (2.31 g) yield.

$^1$H NMR (CDCl$_3$, 500 MHz) δppm: 7.40 (d, J=9.0 Hz, 2H), 7.21 (d, J=16.0 Hz, 1H, =CH), 7.08 (s, 1H), 6.91 (d, J=3.0 Hz, 1H), 6.62 (d, J=9.0 Hz, 2H), 4.05 (m, 4H, OCH$_2$), 3.87 (s, 3H, CH$_3$), 3.84 (s, 3H, CH$_3$), 3.23-3.32 (m, overlap, 6H, CH$_2$N, CH$_2$PO), 1.59 (m, 4H, CH$_2$), 1.37 (m, 4H, CH$_2$), 1.27 (t, J=7.0 Hz, 6H), 0.97 (t, J=7.0 Hz, 6H) $^{13}$C NMR (CDCl$_3$, 125.7 MHz) δppm: 151.4, 150.5, 147.7, 129.0, 127.8, 126.8, 126.7, 124.9, 119.1, 119.0, 118.0, 114.7, 114.6, 111.5, 61.9, 56.2, 50.7, 29.4, 27.2, 26.1, 20.3, 16.4, 14.0.

Example 94

Preparation of N-(4-{(E)-2-{4-[4-(1-tert-butoxycarbonyl)piperazin-1-yl]phenyl}ethenyl)-2,5-dimethoxyphenyl]ethenyl}phenyl)N,N-dibutylamine (104). To a solution of diethyl 4-{(E)-2-[4-(dibutylamino)phenyl]ethenyl}-2,5-dimethoxybenzyl phosphonate (103) (2.25 g, 4.35 mmol) and 4-N-tert-butoxycarbonyl-piperazinobenzaldehyde (1.26 g, 4.35 mmol) in 50 ml of THF was added 1M potassium tert-butoxide (4.5 ml) in THF at 0° C. The mixture was stirred for 5 h at 0° C. and allowed to rise to ambient temperature. The reaction was quenched by addition of 40 ml of water. After removal of solvent under reduced pressure, the product was purified by flash chromatography using ethyl acetate/hexanes (3:7) as eluant and isolated in 71.4% (2.03 g) yield.

$^1$H NMR (CDCl$_3$, 500 MHz) δppm: 7.47 (d, J=9.0 Hz, 2H), 7.42 (d, J=8.5 Hz), 7.34 (d, J=16.5 Hz, 1H), 7.25 (d, J=16.0 Hz, 1H, =CH, overlap with solvent peak), 7.12 (s, 1H), 7.11 (s, 1H),7.04 (d, J=16.5 Hz, 1H, =CH), 7.03 (d, J=16.5 Hz, 1H, =CH), 6.91 (d, J=9.0 Hz, 2H), 6.63 (d, J=8.5 Hz, 2H), 3.92 (s, 3H, CH$_3$), 3.91 (s, 3H, CH$_3$), 3.60 (t, J=4.5 Hz, 4H, CH$_2$), 3.30 (t, J=7.5 Hz, 4H, CH$_2$), 3.18 (s, br, 4H, CH$_2$), 1.59 (m, 4H, CH$_2$), 1.38 (m, 4H, CH$_2$), 0.97 (t, J=7.5 Hz, 6H) $^{13}$C NMR (CDCl$_3$, 125.7 MHz) δppm: 154.7, 151.3, 151.1, 150.3, 147.7, 130.0, 128.9, 127.8, 127.5, 127.2, 125.7, 125.0, 120.7, 118.0, 116.3, 111.5, 108.9, 108.4, 79.9, 56.5, 56.4, 50.8, 49.1, 29.5, 28.4, 20.3, 14.0 (2 carbons was not observed)

HRMS (FAB) Calcd. For C$_{41}$H$_{55}$N$_3$O$_4$: M$^+$653.42. Found 653.4193.

Anal. Calcd. For C$_{41}$H$_{55}$N$_3$O$_4$: C, 75.31; H, 8.48;. N, 6.43. Found: C, 75.08; H, 8.78; N, 6.44.

Example 95

Preparation of 4-N,N-{2,5-dimethoxy-4-[(E)-2-(4-piperazin-1-ylphenyl)ethenyl]phenyl}ethenyl)aniline (105). To a solution of N-(4-{(E)-2-{4-[4-(1-tert-butoxycarbonyl)piperazin-1-yl]phenyl}ethenyl)-2,5-dimethoxyphenyl]ethenyl}phenyl)N,N-dibutylamine (104) (1.53 g, 2.34 mmol) in 50 ml of THF was added 15 ml of 2M hydrochloric acid. The mixture was heated to reflux for 6 h and allowed to cool to room temperature. The solution was neutralized with a solution of sodium hydroxide and extracted three times with ether/methylene chloride (4:1). The combined organic layer was dried over anhydrous magnesium sulfate. After removal of solvent, the product was purified by recrystallization from toluene/hexanes to give a yield of 85.7% (1.11 g). $^1$H NMR (CDCl$_3$, 500 MHz) δppm: 7.47 (d, J=8.5 Hz, 2H), 7.41 (d, J=9.0 Hz), 7.34 (d, J=16.5 Hz, 1H), 7.25 (d, J=16.0 Hz, 1H, =CH, overlap with solvent peak), 7.11 (s, 1H), 7.10 (s, 1H), 7.04 (d, J=16.5 Hz, 1H, =CH), 7.02 (d, J=16.5 Hz, 1H, =CH), 6.91 (d, J=9.0 Hz, 2H), 6.63 (d, J=8.5 Hz, 2H), 3.92 (s, 3H, CH$_3$), 3.91 (s, 3H, CH$_3$), 3.30 (t, J=7.5 Hz, 4H, CH$_2$), 3.20 (t, br, 4H, CH$_2$), 3.05 (t, br, 4H, CH$_2$), 1.59 (m, 4H, CH$_2$), 1.37 (m, 4H, CH$_2$), 0.97 (t, J=7.5 Hz, 6H)$^{13}$C NMR (CDCl$_3$, 125.7 MHz) δppm: 151.3, 151.1, 151.0, 129.4, 128.9, 128.0, 127.8, 127.4, 127.1, 125.9, 125.0, 120.4, 118.0, 115.8, 111.5, 108.8, 108.5, 56.5, 56.4, 50.8, 50.1, 46.1, 29.5, 20.3, 14.0

HRMS (FAB): calcd C$_{36}$H$_{47}$N$_3$O$_2$. For M$^+$553.37, found for [M+H]$^+$554.3748.

Anal. Calcd. C$_{36}$H$_{47}$N$_3$O$_2$ For: C, 78.08; H, 8.55;. N, 7.59. Found: C, 78.40; H, 8.65; N, 7.70.

Example 96

Preparation of [4-(4-{4-[(E)-2-(4-{(E)-2-[4-(dibutylamino)phenyl]ethenyl}-2,5-dimethoxyphenyl)ethenyl]phenyl}piperazin-1-yl)phenyl](diphenyl)sulfonium hexafluorophosphate (106). A mixture of 4-N,N-{2,5-dimethoxy-4-[(E)-2-(4-piperazin-1-ylphenyl)ethenyl]phenyl}ethenyl)aniline (105) and 4-fluorotriphenylsulfonium hexafluorophosphate (0.46 g, 1.08 mmol) in 5 ml of N,N-dimethyl sulfoxide was heated to 100° C. for 6 hours. Upon cooling to ambient temperature, the mixture was poured into a 5% aqueous solution of potassium hexafluorophosphate. The yellow solid was collected by filtration and washed three times with the above solution. The product was purified by flash chromatography using neutral alumina and methylene chloride/methanol as eluant.

$^1$H NMR (CDCl$_3$, 500 MHz) δ ppm: 7.69 (t, br, J=7.2 Hz, 2H), 7.65 (t, J=8.0 Hz, 4H), 7.56 (d, J=8.0 Hz, 4H), 7.53 (d, J=9.0 Hz, 2H), 7.46 (d, J=9.0 Hz, 2H), 7.41 (d, J=8.5 Hz, 2H), 7.33 (d, J=16.5 Hz, 1H, =CH), 7.25 (d, J=16.5 Hz, 1H, =CH), 7.0-7.15 (m, 6H), 6.87 (d, J=9.0 Hz, 2H), 6.62 (d, J=8.5 Hz, 2H), 3.91 (s, 3H, CH$_3$), 3.89 (s, 3H, CH$_3$), 3.56 (t, br, 4H, CH$_2$), 3.34 (t, br, 4H, CH$_2$), 3.92 (t, J=7.5 Hz, 4H), 1.58 (m, 4H, CH$_2$), 1.36 (m, 4H, CH$_2$), 0.96 (t, J=7.2 Hz, 6H, CH$_3$).$^{13}$C NMR (CDCl$_3$, 125.7 MHz) δppm: 154.5, 151.3, 151.1, 149.6, 147.7, 134.1, 133.3, 131.4, 130.1, 129.9, 129.0, 127.8, 127.5, 126.1, 125.7, 125.0, 120.7, 117.9, 115.8, 115.7, 111.5, 108.9, 108.4, 105.7, 56.5, 56.4, 50.7, 48.2, 46.4, 29.5, 20.3, 14.0

HRMS (FAB) Calcd. For C$_{54}$H$_{60}$N$_3$O$_2$S: M$^+$814.44. Found 814.4418.

Anal. Calcd. C$_{54}$H$_{60}$N$_3$O$_2$SPF$_6$ For: C, 67.55; H, 6.30;. N, 4.38. Found: C, 67.47; H, 6.22; N, 4.44.

Example 97

Preparation of E,E-1,4-bis[4'-piperazino-(N-tert-butoxycarbonyl)styryl]benzene (107). To a solution of N-tert-butoxycarbonyl-N'-(p-formylphenyl)piperazine (2.0 g, 6.89 mmol) and tetraethyl 2,5-bis(butoxyl)-p-xylene phosphonate (1.79 g, 3.43 mmol) in 50 ml of THF was added 1M KO$^t$Bu (7 ml, 7 mmol) at 0° C. The mixture was stirred at 0° C. for 2 hours. The reaction was quenched by addition of 50 ml of water. The yellow solid was collected by filtration and washed three times with methanol; the yield was 91.7% (2.50 g). $^1$H NMR (500 MHz, CDCl$_3$) δppm: 7.45 (d, J=8.5 Hz, 4H), 7.34 (d, J=16.0 Hz, 2H, =CH), 7.10 (s, 2H), 7.05 (d, J=16.0 Hz, 2H, =CH), 6.92 (d, J=8.5 Hz, 4H), 4.05 (t, J=6.5 Hz, 4H), 3.60 (m, 8H, NCH$_2$), 3.20 (m, 8H, NCH$_2$), 1.85 (m, 4H, CH$_2$), 1.57 (m, 4H, CH$_2$), 1.49 (s, 18H, CH$_3$), 1.02 (t, 6H, CH$_3$).

Example 98

Preparation of E,E-1,4-bis[4'-piperazinostyryl]benzene (108). 2M HCl (2.5 ml) was added to a solution of E,E-1,4-bis[4'-piperazino-(N-tert-butoxycarbonyl)styryl]benzene (0.68 g, 0.86 mmol) in 30 ml of THF at 0° C. The mixture was refluxed for 2 hours. The reaction mixture was allowed to cool to ambient temperature and the pH adjusted to 13-14 with an aqueous solution of sodium hydroxide. The aqueous layer was extracted three times with 20 ml of ether, and the combined organic layer was washed three times with 20 ml of saturated brine and dried over anhydrous sodium sulfate. After removal of solvent, the residue was recrystallized from toluene and was isolated in 0.21 g (41.3%) yield. $^1$H NMR (500 MHz, CDCl$_3$) δppm: 7.45 (d, J=8.5 Hz, 4H), 7.34 (d, J=16.5 Hz, 2H, =CH), 7.10 (s, 2H), 7.06 (d, J=16.0 Hz, 2H, =CH), 6.92 (d, J=9.0 Hz, 4H), 4.05 (t, J=6.5 Hz, 4H), 3.20 (m, 8H, NCH$_2$), 3.05 (m, 8H, NCH$_2$), 1.86 (m, 4H, CH$_2$), 1.59 (m, 4H, CH$_2$), 1.03 (t, J=7.5 Hz, 6H, CH$_3$) $^{13}$C NMR (125.7 MHz, CDCl$_3$) δppm: 151.0, 150.8, 129.5, 128.2, 127.4, 126.8, 120.6, 115.8, 110.3, 69.2, 50.0, 46.1, 31.6, 19.4, 14.0.

Example 99

Preparation of Compound 109. To a solution of julolidinecarboxaldehyde (201 mg, 1 mmol) and (julolidinylmethyl)triphenylphosphonium iodide (691 mg, 1.2 mmol) in anhydrous CH$_2$Cl$_2$ (50 mL) was added potassium tert-butoxide (168 mg, 1.5 mmol). The suspension was stirred overnight at room temperature while protected from light and moisture. Water was added and the mixture was extracted with methylene chloride. The solvent was removed and the precipitate was recrystallized from ethanol to give the product in 64% yield.

$^1$H NMR (500 MHz, d$_6$-Acetone) δ ppm: 6.87 (s, 4H), 6.69 (s, 2H), 3.14 (t, $^3$J(H,H)=5.6 Hz, 8H), 2.72 (t, $^3$J(H,H)=6.4 Hz, 8H), 1.94 (quint, $^3$J(H,H)=5.9 Hz, 8H) HRMS (FAB) calcd for C$_{26}$H$_{30}$N$_2$: 370.2409 (M$^+$), found: 370.2390.

Example 100

Preparation of Compound 110. To a solution of julolidinecarboxaldehyde (402 mg, 2 mmol) and tetraethyl 2,5-dicyano-p-xylene phosphonate (428 mg, 1 mmol) in anhydrous THF (50 mL) was added potassium tert-butoxide (500 mg, 2.2 mmol). The suspension was stirred at room temperature for 20 hours while protected from light and moisture. The suspension was filtered through a bed of Celite which was rinsed with methylene chloride. The solvent was removed and the precipitate was recrystallized from ethanol to give the product in 60% yield.

$^1$H NMR (250 MHz, CDCl$_3$) δppm: 7.94 (s, 2H), 7.15 (d, $^3$J(H,H)=16.0 Hz, 2H), 7.08 (d, $^3$J(H,H)=15.9 Hz, 2H), 7.07 (s, 4H), 3.26 (t, $^3$J(H,H)=5.7 Hz, 8H), 2.82 (t, $^3$J(H,H)=6.3 Hz, 8H), 2.02 (quint, $^3$J(H,H)=5.7 Hz, 8H). HRMS (FAB) calcd for C$_{36}$H$_{34}$N$_4$: 522.2783 (M$^+$), found: 522.2773.

Example 101

Preparation of Compound 111. To a solution of terephthaldicarboxaldehyde (134 mg, 1 mmol) (julolidinylmethyl)triphenylphosphonium iodide (1.4 g, 2.5 mmol) in anhydrous CH$_2$Cl$_2$ (50 mL) was added potassium tert-butoxide (500 mg, 4 mmol). The suspension was stirred at room temperature for 20 hours while protected from light and moisture. Toluene and water were added to the suspension. The solution was extracted with toluene. The solution was dried under sodium sulfate and the solvent was removed. The crude product was obtained in 52% yield after purification by silica gel column chromatography, eluting with methylene chloride.

$^1$H NMR (500 MHz, CDCl$_3$) δ ppm: 7.40 (s, 4H), 6.98 (s, 4H), 6.94 (d, $^3$J(H,H)=16.1 Hz, 2H), 6.83 (d, $^3$J(H,H)=16.1 Hz, 2H), 3.17 (t, $^3$J(H,H)=5.1 Hz, 8H), 2.78 (t, $^3$J(H,H)=6.4 Hz, 8H), 1.99 (quint, $^3$J(H,H)=5.6 Hz, 8H). Anal. calcd C$_{34}$H$_{36}$N$_2$+0.14 CH$_2$Cl$_2$: C, 84.38, H, 7.53, N, 5.76, found: C, 84.38, H, 7.61, N, 5.65. HRMS (FAB) calcd for C$_{34}$H$_{36}$N$_2$: 472.2878 (M$^+$), found: 472.2878.

Example 102

Photopolymerizations initiated by one-photon excitation. Aliquots (1.25 ml) of a 10 ml of solution containing 0.0791 mmol of sulfonium salt, such as 7, 8, 9, 23, 41, 52, or 61 and 8 ml of cyclohexene oxide (7.76 g, 0.0791 mol) in methylene chloride were sealed in 4-ml Pyrex vials with caps and irradiated with a 419 nm photochemical lamp in a merry-go-round holder. After various intervals the sample tubes were withdrawn from the irradiation chamber and any ionic reactions were immediately quenched by the addition of 2M ammonia solution in methanol (1 ml). The polymers were precipitated by addition to methanol, collected by filtration and dried in vacuo for 40 hours. The plots of time versus conversion is shown in FIGS. 3 and 4 (above) demonstrate that each of the salts described in this example of efficient initiators for cationic polymerization.

Example 103

Photochemical generation of acid in solution by one-photon excitation and determination of the photochemical quantum yield for compounds 23, 41, and 52. The quantum yield for photochemical generation of acid, $\phi_{H^+}$, was obtained from measurements of the acid generated when a 4.0×10$^{-4}$ M solution of a PAG in acetonitrile was one-photon excited by irradiation at 400 nm using either the monochromated output of a xenon lamp or a frequency-doubled mode-locked Ti:sapphire laser. At this concentration more than 99% of the incident photons were absorbed. The photogenerated acid was titrated by the addition of excess rhodamine B base in acetonitrile (6.0×10$^{-5}$ M after addition) and quantified spectrophotometrically from the absorbance of protonated rhodamine B base. The acid-generation quantum yields were $\phi_{H^+}$=0.55±0.05, 0.44±0.04, and 0.013±0.002 for 23, 41, and 52, respectively.

Example 104

Photochemical generation of acid in solution by two-photon excitation of compound 41. Samples of 41 in acetonitrile (4.0×10$^{-4}$ M) were excited in 1-cm path-length fluorescence cells using focused (f=75 mm) 80-fs pulses from a CW mode-locked Ti:sapphire laser (82-MHz, 8.5-mm diameter spot-size at lens). The two-photon-excitation (TPE) spectrum was recorded using the two-photon-fluorescence method with fluorescein in water (1.54×10$^{-5}$ M, pH=11) as a reference. The up-converted fluorescence was detected at 520 nm and its intensity was proportional to the square of the excitation power, as expected for two-photon absorption (TPA). The concentration of the photogenerated acid, [H$^+$], was determined spectrophotometrically following a 30-minute exposure. The relative acid-yield efficiency at each wavelength was calculated by dividing [H$^+$] by the ratio of the emission counts and the TPE action cross-section of the fluorescein reference (<F(t)>/$\phi_f\delta$)$_{ref}$(to account for the temporal and spatial dependence of the excitation intensity as a function of wavelength) and normalizing to δ of 41 at 705 nm. The TPE and the acid-yield efficiency spectra are shown in FIG. 7. The inset is a plot of the acid-yield versus two-photon-excitation power at 745 nm. 41 exhibits strong TPA from 705-850 nm (δ>100 GM) that appears to peak near 710 nm (δ=690 GM), consistent with measurements obtained for similar bis[(diarylamino)styryl]benzenes. The TPE and acid-yield efficiency spectra exhibit similar features, and the acid-yield at 745 nm increases quadratically with excitation power, as expected for a photochemical process activated by TPA.

Example 105

Comparison of compounds 23 and 41 with conventional PAGs for sensitivity toward two-photon-initiated polymerization of the liquid epoxide resins Araldite CY179MA and 4-vinyl-1-cyclohexene diepoxide. The epoxide polymerization sensitivity of 23 and 41 under near-infrared excitation was compared with that of four widely-used conventional PAGs (FIG. 8): CD1012, CD1012/ITX (1:1.6 molar ratio), TPS, and DPI-DMAS. Test resins of each initiator (10 mM) in Araldite CY179MA (Ciba, 7-oxabicyclo[4.1.0]heptane-3-carboxylic acid, 7-oxabicyclo[4.1.0]hept-3-ylmethyl ester) and 4-vinyl-1-cyclohexene diepoxide were irradiated with focused (f=75 mm) 80-fs pulses from a Ti:sapphire laser (82-MHz repetition rate, 0.94-mm diameter spot-size at lens). The threshold power for the onset of polymerization within a 10-second exposure was established at 710 and 760 nm by the advent of a circular diffraction pattern in the far-field of the transmitted beam. Exposure at higher powers and for longer times produced clearly visible solid features of cross-linked polymer. In Araldite using 710-nm excitation, the threshold powers were 2.4 mW (41), 44 mW (CD1012/ITX), and 212 mW (CD1012). The available power (317 mW) was insufficient to initiate polymerization of the TPS and DPI-DMAS resins. In Araldite using 760-nm excitation, the threshold powers were 5.6 mW (41), 50 mW (CD1012/ITX), 468 mW (DPI-DMAS), and 560 mW (CD1012). The available power (655 mW) was not adequate to initiate polymerization of the TPS resin. In 4-vinyl-1-cyclohexene diepoxide using 710-nm excitation, the threshold powers were 1.7 mW (41), 4.4 mW (23), 33 mW (CD1012/ITX), and 185 mW (CD1012). The available power (317 mW) was insufficient to initiate polymerization of the TPS and DPI-DMAS resins. In 4-vinyl-1-cyclohexene diepoxide using 760-nm excitation, the threshold powers were 4.7 mW (41), 6.4 mW (23), and 45 mW (CD1012/ITX). The available power (655 mW) was not adequate to initiate polymerization of the CD1012, DPI-DMAS, and TPS resins. The threshold measurements show that the two-photon sensitivity of 23 and 41 is nearly one order of magnitude greater than that of the best-performing conventional initiator, (CD1012/ITX), and more than two orders of magnitude greater than that of TPS.

Example 106

Fabrication of three-dimensional microstructures in a solid epoxide resin containing compound 41 using femtosecond laser pulses. In the dark, 393 mg of EPON SU-8 (Shell), 262 mg of γ-butyrolactone, and 10.2 mg of 41 (2.5 wt.-% in resin) were stirred until the solids had dissolved. The resin mixture was blade-casted onto a substrate treated with a trimethoxy[2-(7-oxabicyclo[4.1.0]hept-3-yl)ethyl]silane adhesion promoter at a thickness of 510 μm, dried in air at room temperature for 10 days, then heated on a hot-plate at 100° C. for 15 minutes. The resulting solid film had a thickness of 330±100 μm. The film was exposed in a target three-dimensional pattern by tightly focusing 80-fs pulses from a Ti:sapphire laser at a wavelength of 745 nm into the resin while translating the focal point at a speed of 50 μm/s (60×/1.4 N.A. oil-immersion objective, 82-MHz pulse repetition rate). The average optical power at the film was varied between 1-5 mW. Following irradiation, the film was immersed in γ-butyrolactone for 60 minutes to remove the unexposed resin, and then rinsed with methanol, leaving the microstructures shown in FIG. 9 standing freely on the substrate.

Example 107

Two-photon polymerization of a solid epoxide resin containing PAG 41 using femtosecond laser pulses and measurement of the polymerization threshold power. In the dark, 200 mg of EPON SU-8, 133 mg of γ-butyrolactone, and 2 mg of 41 (1 wt.-% in resin) were stirred until the solids had dissolved. The resin mixture was blade-casted onto a substrate treated with a trimethoxy[2-(7-oxabicyclo[4.1.0]hept-3-yl) ethyl]silane adhesion promoter at a thickness of 510 μm, dried in air at room temperature for 10 days, then heated on a hot-plate at 100° C. for 15 min. The resulting solid film had a thickness of 330±100 μm. The film was exposed in a target three-dimensional test-pattern by tightly focusing 70-fs pulses from a Ti:sapphire laser at a wavelength of 730 mn into the resin while translating the focal point at a speed of 50 μm/s (60×/1.4 N.A. oil-immersion objective, 82-MHz pulse repetition rate). Following irradiation, the film was immersed in γ-butyrolactone for 60 minutes to remove the unexposed resin, and then rinsed with methanol, leaving free-standing microstructures where the average exposure power was suitably high. Inspection of the sample before and after developing with γ-butyrolactone revealed that the resin was damaged for average optical powers exceeding 17±2 mW, and the threshold power for polymerization was 0.3±0.1 mW.

Example 108

Two-photon polymerization of a solid epoxide resin containing compound 52 using femtosecond laser pulses and measurement of the polymerization threshold power. In the dark, 200 mg of EPON SU-8, 142 mg of γ-butyrolactone, and 5 mg of 52 (2.5 wt.-% in resin) were stirred until the solids had dissolved. The resin mixture was blade-casted onto a substrate treated with a trimethoxy[2-(7-oxabicyclo[4.1.0]hept-3-yl)ethyl]silane adhesion promoter at a thickness of 510 μm, dried in air at room temperature for 10 days, then heated on a hot-plate at 100° C. for 15 min. The resulting solid film had a thickness of 330±100 μm. The film was exposed in a target three-dimensional test-patent by tightly focusing 70-fs pulses from a Ti:sapphire laser at a wavelength of 730 nm into the resin while translating the focal point at a speed of 50 μm/s (60×/1.4 N.A. oil-immersion objective, 82-MHz pulse repetition rate). Following irradiation, the film was immersed in γ-butyrolactone for 60 minutes to remove the unexposed resin, and then rinsed with methanol, leaving free-standing microstructures where the average exposure power had been suitably high. Inspection of the sample before and after developing with γ-butyrolactone revealed that the resin was damaged for average optical powers exceeding 17±2 mW, and the threshold power for polymerization was 1.3±0.3 mW.

Example 109

Two-photon polymerization of a solid epoxide resin containing compound 23 using femtosecond laser pulses and measurement of the polymerization threshold power. In the dark, 200 mg of EPON SU-8, 140 mg of γ-butyrolactone, and 4.7 mg of 52 (2.4 wt.-% in resin) were stirred until the solids had dissolved. The resin mixture was blade-casted onto a substrate treated with a trimethoxy[2-(7-oxabicyclo[4.1.0] hept-3-yl)ethyl]silane adhesion promoter at a thickness of 510 μm, dried in air at room temperature for 10 days, then heated on a hot-plate at 100° C. for 15 min. The resulting solid film had a thickness of 230±100 μm. The film was exposed in a target three-dimensional test-pattern by tightly focusing 70-fs pulses from a Ti:sapphire laser at a wavelength of 720 nm into the resin while translating the focal point at a speed of 50 μm/s (60×/1.4 N.A. oil-immersion objective, 82-MHz pulse repetition rate). Following irradiation, the film was immersed in γ-butyrolactone for 60 minutes to remove the unexposed resin, and then rinsed with methanol, leaving free-standing microstructures where the average exposure power was suitably high. Inspection of the sample before and after developing with γ-butyrolactone revealed that the resin was damaged for average optical powers exceeding 17±2 mW, and the threshold power for polymerization was ~7 mW.

Example 110

Fabrication of sub-millimeter columnar structures by two-photon polymerization of a liquid epoxide resin containing PAG 41 using nanosecond laser pulses. A cell was fashioned by sandwiching a 2-mm thick o-ring between two glass substrates, one of which was treated with a trimethoxy[2-(7-oxabicyclo[4.1.0]hept-3-yl)ethyl]silane adhesion promoter. The cell was filled with 10.3 mM 41 in 20%/80% EPON SU-8/4-vinyl-1-cyclohexene diepoxide (1.26 wt.-% PAG). Several regions of the cell were then irradiated for 5 s using focused 4.0-mJ 5-ns laser pulses at a wavelength of 745 nm (10-Hz repetition rate; 500-mm focal length lens; 6-mm beam diameter at the lens). Columns of cross-linked polymer that spanned the length of the cell formed in the irradiated region. Following exposure, the cell was disassembled and rinsed with propylene glycol methylether acetate. Free-standing columns of two-photon cross-linked polymer remained on the adhesion-promoted substrate. The width of the columns was typically 200 μm.

Example 111

Fabrication of columnar structures by two-photon-induced polymerization of a liquid epoxide resin containing compound 41 using nanosecond laser pulses and measurement of the polymerization threshold energy. A cell was fashioned by sandwiching a 2-mm thick o-ring between two glass substrates, one of which was treated with a trimethoxy[2-(7-oxabicyclo[4.1.0]hept-3-yl)ethyl]silane adhesion promoter. The cell was filled with 10 mM 41 in 20%/80% EPON SU-8/4-vinyl-1-cyclohexene diepoxide (1.3 wt.-% PAG). Several regions of the film were then irradiated with focused 5-ns laser pulses at a wavelength of 745 mn (10-Hz repetition rate; 500-mm focal length lens; 5-mm beam diameter at the lens). The onset of two-photon-induced polymerization was marked by the appearance of a ringed diffraction pattern in the far-field transmitted beam. Extensive cross-linking ultimately resulted in disruption of the far-field pattern and formation of a column of cross-linked polymer that spanned the length of the cell in the irradiated region. The onset of polymerization occurred at pulse energies of 2.1 ml, 1.4 mJ, 0.9 mn, and 0.9 ml for exposure times of 1 s, 2 s, 3 s, and 5 s, respectively. Following exposure, the cell was disassembled and rinsed with propylene glycol methylether acetate. Free-standing columns of two-photon cross-linked polymer remained on the adhesion-promoted substrate. FIG. 10 shows a scanning electron micrograph of the columns. The width of the smallest feature was 60 μm.

Example 112

Fabrication of columnar structures by two-photon-induced polymerization of a solid epoxide resin containing compound 41 using nanosecond laser pulses and measurement of the polymerization threshold energy. In the dark, 1 g of EPON SU-8, 660 mg of γ-butyrolactone, and 10.2 mg of 41 (1 wt.-% in resin) were stirred until the solids had dissolved. The resin mixture was blade-casted onto a substrate treated with a trimethoxy[2-(7-oxabicyclo[4.1.0]hept-3-yl)ethyl]silane adhesion promoter at a thickness of 510 μm and heated on a hot-plate at 80° C. for 60 min. The resulting solid film had a thickness of 330±100 μm. Several regions of the film were then irradiated with focused 5-ns laser pulses at a wavelength of 745 nm (10-Hz repetition rate; 500-mm focal length lens; 5-mm beam diameter at the lens). The onset of two-photon-induced polymerization was marked by the appearance of a ringed diffraction pattern in the far-field transmitted beam. Extensive cross-linking ultimately resulted in disruption of the far-field pattern and formation of a visible feature in the film. The onset of polymerization occurred at pulse energies of 0.8 mJ, 0.6 mJ, 0.4 mJ, and 0.2 mJ for exposure times of 1 s, 2 s, 3 s, and 5 s, respectively. Following exposure, the unpolymerized resin was removed by soaking the film in propylene glycol methylether acetate for 30 minutes. Free-standing columns of cross-linked polymer were present on the substrate in the irradiated regions.

The entire contents of each of the above-identified references, patents, applications and published applications are hereby incorporated by reference, the same as if set forth at length.

Obviously, numerous modifications and variations of the present invention are possible in light of the above teachings. It is therefore to be understood that within the scope of the appended claims, the invention may be practiced otherwise than as specifically described herein.

The invention claimed is:

1. A compound or composition, comprising:
    at least one chromophore having a simultaneous two-photon or multi-photon absorptivity; and
    at least one photoacid or radical generator in close proximity to said chromophore;
    wherein said chomophore has a two-photon absorption cross-section of $>50 \times 10^{-50}$ cm$^4$ s/photon.
    (1) wherein the generator is a sulfonium group has of formula $-(CH_2)_\gamma-(C_6H_4)_\delta-SR_{a5}R_{a6}$,
        wherein $R_{a5}$ and $R_{a6}$ are each independently alkyl, aryl, or monomer groups, and
        wherein $\gamma=0$ to 25, and $\delta=0$ to 5;
    (2) wherein the generator is a selenonium group of the formula $-(CH_2)_\gamma-(C_6H_4)_\delta-SeR_{a5}R_{a6}$,
        wherein $R_{a5}$ and $R_{a6}$ are each independently alkyl, aryl, or monomer groups, and
        wherein $\gamma=0$ to 25, and $\delta=0$ to 5; or
    (3) wherein the generator is an iodonium group of the formula $-(CH_2)_\gamma-(C_6H_4)_\delta-IR_{a7}$,
        wherein $R_{a7}$ is alkyl, aryl, or monomer group, and
        wherein $\gamma=0$ to 25, and $\delta=0$ to 5.

2. A method for making an article, comprising:
    contacting the compound or composition of claim 1 with at least one polymerizable or cross-linkable monomer, oligomer, or prepolymer, or acid-modifiable medium;
    irradiating said compound or composition to cause a simultaneous two-photon or multi-photon absorption in said chomophore; and
    polymerizing said monomer, oligomer, or prepolymer or cleaving a group from said acid-modifiable medium.

3. An article, produced by the method of claim 2.

4. The compound or composition of claim 1, wherein upon simultaneous absorption of two or more photons, said chromophore adopts an electronically excited state, and therefrom activates said generator to generate a Brønsted or Lewis acid and/or radical.

5. The compound or composition of claim 1,
wherein the sulfonium group has the formula —$(CH_2)_\gamma$—$(C_6H_4)_\delta$—$SR_{a5}R_{a6}$,
wherein $R_{a5}$ and $R_{a6}$ are each independently alkyl, aryl, or monomer groups, and
wherein $\gamma=0$ to 25, and $\delta=0$ to 5.

6. The compound or composition of claim 1,
wherein the selenonium group has the formula —$(CH_2)_\gamma$—$(C_6H_4)_\delta$—$SeR_{a5}R_{a6}$,
wherein $R_{a5}$ and $R_{a6}$ are each independently alkyl, aryl, or monomer groups, and
wherein $\gamma=0$ to 25, and $\delta=0$ to 5.

7. The compound or composition of claim 1,
wherein the iodonium group has the formula —$(CH_2)_\gamma$—$(C_6H_4)_\delta$—$IR_{a7}$,
wherein $R_{a7}$ is alkyl, aryl, or monomer group, and
wherein $\gamma=0$ to 25, and $\delta=0$ to 5.

8. The compound or composition of claim 1, wherein said chromophore and said generator are each present in concentrations of 0.001 M to 2 M.

9. The compound or composition of claim 1, wherein said chromophore is an anion.

10. The compound or composition of claim 1, further comprising at least one polymerizable or cross-linkable monomer, oligomer, or prepolymer, or acid-modifiable medium.

11. A method for generating a Brønsted or Lewis acid and/or radical, comprising irradiating said compound or composition of claim 1 to cause a simultaneous two-photon or multi-photon absorption in said chomophore.

12. A composition which has the structure:

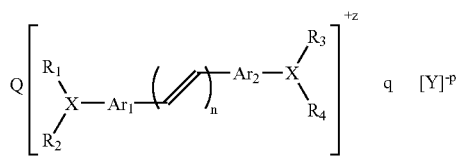

wherein X=S, Se, I, O, N and n=0, 1, 2, 3, 4, or 5,
wherein $Ar_1$ and $Ar_2$ are each independently a 5-membered heteroaromatic ring; a 6-membered aromatic ring; or a 6-membered heteroaromatic ring,
wherein each of $Ar_1$ and $Ar_2$ are optionally independently substituted with one or more H, alkyl group, alkoxy group, or aryl group, which groups may be optionally independently substituted with one or more sulfonium, selenonium, or iodonium groups; other acid- or radical-generating species; or monomer or pre-polymer groups,
wherein $R_1$, $R_2$, $R_3$, and $R_4$ are each independently alkyl or aryl groups, which groups may be optionally independently substituted one or more sulfonium, selenoniumn, or iodonium groups; other acid- or radical-generating species; or monomer or pre-polymer groups,
wherein Y is an anion selected from the group consisting of $F^-$, $Cl^-$, $Br^-$, $I^-$, $CN^-$, $SO_4^{2-}$, $PO_4^{3-}$, $CH_3CO_2^-$, $CF_3SO_3^-$, $NO_2^-$, $NO_3^-$, $BF_4^-$, $PF_6^-$, $SbF_6^-$, $AsF_6^-$, $SbCl_4^-$, $ClO_3^{3-}$, $ClO_4^-$, and $B(aryl)_4^-$, where aryl is an aryl group containing 25 or fewer carbon atoms that may be optionally substituted with one or more alkyl groups, aryl groups or halogens,
wherein z is an integer equal to the charge of the chromophore portion of the compound,
wherein p is an integer equal to the charge on the anion, and
wherein q and Q are integers such that the relationship zQ=pq is satisfied.

13. The composition of claim 12,
wherein X=I.

14. The composition of claim 12,
wherein X is O.

15. A composition which has the structure:

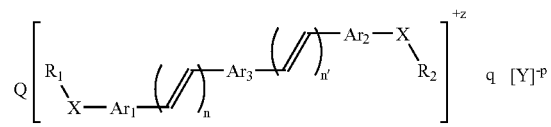

wherein X is I, S, Se or O, n=0, 1, 2, 3, 4, or 5, and n'=0, 1, 2, 3, 4 or 5,
wherein $Ar_1$ and $Ar_2$ are each independently a 5-membered heteroaromatic ring; a 6-membered aromatic ring; or a 6-membered heteroaromatic ring,
wherein $Ar_3$ is a 5-membered heteroaromatic ring; a 6-membered aromatic ring; or a 6-membered heteroaromatic ring,
wherein each of $Ar_1$ and $Ar_2$ are optionally independently substituted with one or more H, alkyl group, alkoxy group, or aryl group, which groups may be optionally independently substituted with one or more sulfonium, selenonium, or iodonium groups; other acid- or radical-generating species; or monomer or pre-polymer groups,
wherein $Ar_3$ is optionally substituted with one or more H, acceptor group, alkyl group, alkoxy group, aryl group, which groups may be optionally independently substituted with one or more sulfonium, selenonium, or iodonium groups; other acid- or radical-generating species; or monomer or pre-polymer groups,
wherein $R_1$ and $R_2$ are each independently alkyl group, or aryl group, which groups may be optionally independently substituted with one or more sulfonium, selenonium, or iodonium groups; other acid- or radical-generating species; or monomer or pre-polymer groups,
wherein Y is an anion selected from the group consisting of $F^-$, $Cl^-$, $Br^-$, $I^-$, $CN^-$, $SO_4^{2-}$, $PO_4^{3-}$, $CH_3CO_2^-$, $CF_3SO_3^-$, $NO_2^-$, $NO_3^-$, $BF_4^-$, $PF_6^-$, $SbF_6^-$, $AsF_6^-$, $SbCl_4^-$, $ClO_3^-$, $ClO_4^-$; and $B(aryl)_4^-$; where aryl is an aryl group containing 25 or fewer carbon atoms that may be optionally substituted with one or more alkyl groups, aryl groups or halogens,
wherein z is an integer equal to the charge of the chromophore portion of the compound,
wherein p is an integer equal to the charge on the anion, and
wherein q and Q are integers such that the relationship zQ=pq is satisfied.

16. The composition of claim 15,
wherein X is S or Se.

17. The composition of claim 15,
wherein X is O.

18. A composition which has the structure:

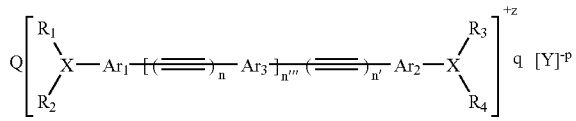

wherein X is N, n=0, 1, 2, 3, 4, or 5, n'=0, 1, 2, 3, 4 or 5 and n'''=0, 1, 2, 3, 4, or 5,
wherein $Ar_1$ and $Ar_2$ are each independently a 5-membered heteroaromatic ring; a 6-membered aromatic ring; or a 6-membered heteroaromatic ring,
wherein $Ar_3$ is a 5-membered heteroaromatic ring; a 6-membered aromatic ring; or a 6-membered heteroaromatic ring, wherein each of $Ar_1$ and $Ar_2$ are optionally independently substituted with one or more H, alkyl group, alkoxy group, aryl group, which groups may be optionally independently substituted with one or more sulfonium, selenonium, or iodonium groups; other acid- or radical-generating species; or monomer or pre-polymer groups, wherein $Ar_3$ is optionally substituted with one or more H, acceptor group, alkyl group, alkoxy group, aryl group, which groups may be optionally independently substituted with one or more sulfonium, selenonium, or iodonium groups; other acid- or radical-generating species; or monomer or pre-polymer groups, wherein $R_1$, $R_2$, $R_3$, and $R_4$ are each independently H, alkyl group, aryl group, which groups may be optionally independently substituted with one or more sulfonium, selenonium, or iodonium groups; other acid- or radical-generating species; or monomer or pre-polymer groups, wherein at least one of $Ar_1$, $Ar_2$, $Ar_3$, $R_1$, $R_2$, $R_3$, or $R_4$ is substituted with one or more sulfonium, selenonium, or iodonium groups, or other acid- or radical generating groups, wherein Y is an anion selected from the group consisting of $F^-$, $Cl^-$, $Br^-$, $I^-$, $CN^-$, $SO_4^{2-}$, $PO_4^{3-}$, $CH_3CO_2^-$, $CF_3SO_3^-$, $NO_2^-$, $NO_3^-$, $BF_4^-$, $PF_6^-$, $SbF_6^-$, $AsF_6^-$, $SbCl_4^-$, $ClO_3^-$, $ClO_4^-$, and $B(aryl)_4^-$, where aryl is an aryl group containing 25 or fewer carbon atoms that may be optionally substituted with one or more alkyl groups, aryl groups or halogens, wherein z is an integer equal to the charge of the chromophore portion of the compound, wherein p is an integer equal to the charge on the anion, and wherein q and Q are integers such that the relationship zQ=pq is satisfied.

19. A compound or composition, which has the structure:

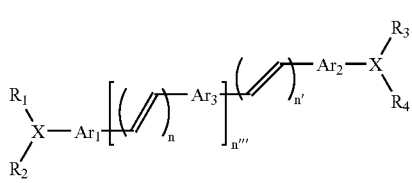

wherein X is N, n=0, 1, 2, 3, 4 or 5, n'=0, 1, 2, 3, 4, or 5 and n'''=0, 1, 2, 3, 4, or 5, wherein $Ar_1$ and $Ar_2$ are each independently a 5-membered heteroaromatic ring; a 6-membered aromatic ring; or a 6-membered heteroaromatic ring, wherein $Ar_3$ is a 5-membered heteroaromatic ring; a 6-membered aromatic ring; or a 6-membered heteroaromatic ring, wherein each of $Ar_1$ and $Ar_2$ are optionally independently substituted with one or more H, alkyl, alkoxy, aryl, thioalkoxy, thioaryloxy, selenoalkoxy, or selenoaryloxy groups, which groups may be optionally independently substituted with monomer or pre-polymer groups, wherein $Ar_3$ is optionally independently substituted with one or more H, acceptor, alkyl, alkoxy, aryl, thioalkoxy, thioaryloxy selenoalkoxy, or selenoaryloxy groups, which groups may be optionally independently substituted with monomer or pre-polymer groups, wherein $R_1$, $R_2$, $R_3$, and $R_4$ are each independently H, alkyl, or aryl groups, which groups may be optionally independently substituted with one or more thioalkoxy, thioaryloxy selenoalkoxy, selenoaryloxy or groups, and wherein at least one of $Ar_1$, $Ar_2$, $Ar_3$, $R_1$, $R_2$, $R_3$, or $R_4$ is substituted with one or more thioalkoxy, thioaryloxy selenoalkoxy, selenoaryloxy groups.

20. The compound or composition of claim 19, wherein the thioether fragment has the formula $-(CH_2)_\gamma-(CH_4H_4)_\delta-SR_{a5}$, wherein $R_{a5}$ is an alkyl group, and wherein $\gamma=0$ to 25, and $\delta=0$ to 5.

21. The compound or composition of claim 19, wherein the thioether fragment has the formula $-(CH_2)_\gamma-(C_6H_4)_\delta-SR_{a5}$, wherein $R_{a5}$ is an aryl group, and wherein $\gamma=0$ to 25, and $\delta=0$ to 5.

22. The compound or composition of claim 19, wherein the selenoether fragment has the formula $-(CH_2)_\gamma-(C_6H_4)_\delta-SeR_{a5}$, wherein $R_{a5}$ is an alkyl group, and wherein $\gamma=0$ to 25, and $\delta=0$ to 5.

23. The compound or composition of claim 19, wherein the selenoether fragment has the formula $-(CH_2)_\gamma(C_6H_4)_\delta-SeR_{a5}$, wherein $R_{a5}$ is an aryl group, and wherein $\gamma=$to 25, and $\delta=0$ to 5.

24. A composition of a form selected from the group consisting of:

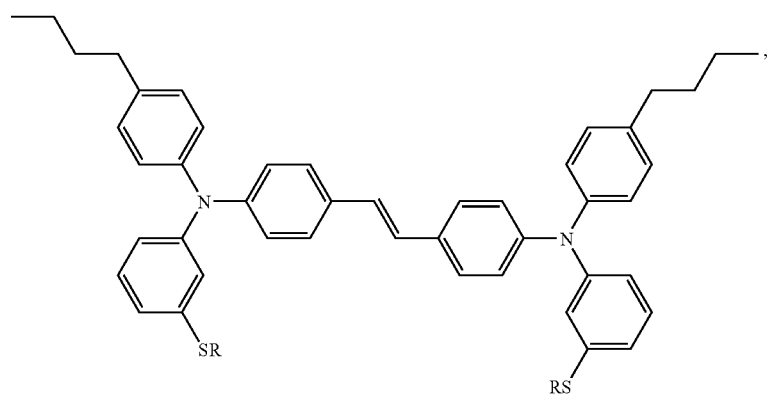

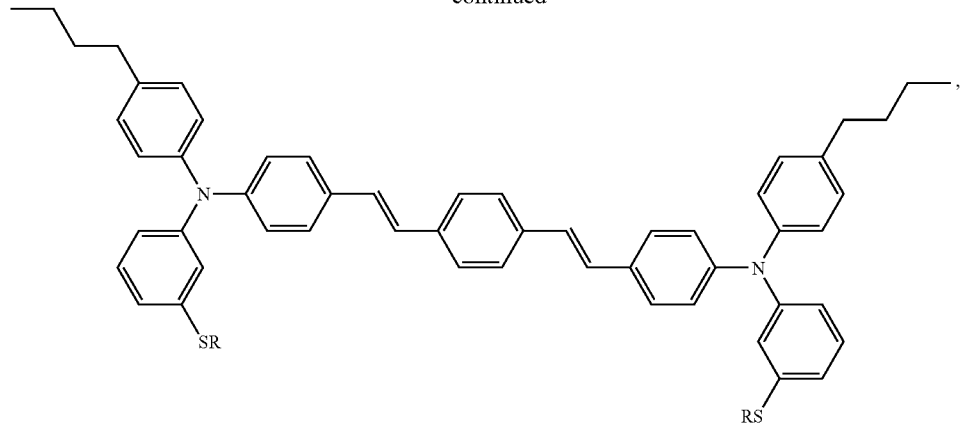
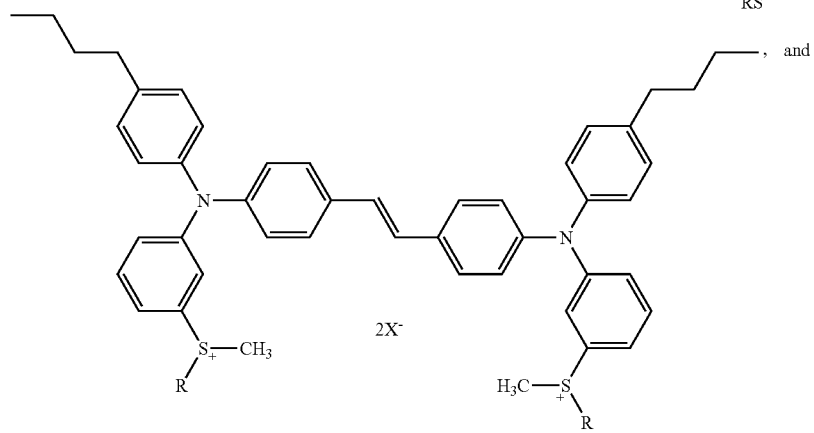, and
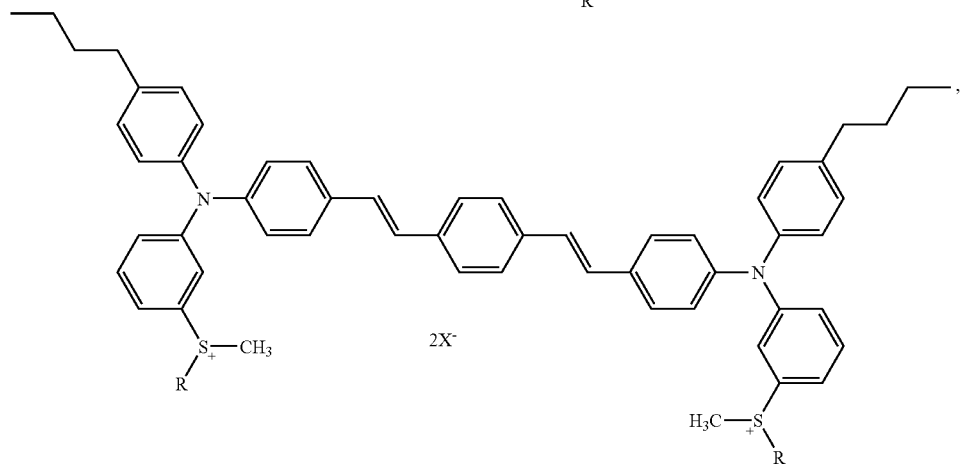
wherein R is methyl or benzyl, and
wherein X is $F^-$, $Cl^-$, $Br^-$, $I^-$, $CN^-$, $SO_4^{2-}$, $PO_4^{3-}$, $CH_3CO_2^-$, $CF_3SO_3^-$, $NO_2^-$, $NO_3^-$, $BF_4^-$, $PF_6^-$, $SbF_6^-$, $AsF_6^-$, $SbCl_4^-$, $ClO_3^-$, $ClO_4^-$, or $B(aryl)_4^-$, where aryl is an aryl group containing 25 or fewer carbon atoms that may be optionally substituted with one or more alkyl groups, aryl groups or halogens.
* * * * *